(12) United States Patent
Zierke et al.

(10) Patent No.: US 10,519,122 B2
(45) Date of Patent: Dec. 31, 2019

(54) PROCESS FOR THE PREPARATION OF SUBSTITUTED OXIRANES AND TRIAZOLES

(71) Applicant: BASF Agro B.V., Arnheim (NL)

(72) Inventors: Thomas Zierke, Boehl-Iggelheim (DE); Joachim Gebhardt, Ludwigshafen (DE); Peter Schaefer, Ottersheim (DE); Uwe Josef Vogelbacher, Trier (DE); Michael Rack, Eppelheim (DE); Jan Klaas Lohmann, Lambsheim (DE)

(73) Assignee: BASF Agro B.V., Arnhem (NL)

( * ) Notice: Subject to any disclaimer, the term of this patent is extended or adjusted under 35 U.S.C. 154(b) by 0 days.

(21) Appl. No.: 15/805,679

(22) Filed: Nov. 7, 2017

(65) Prior Publication Data

US 2018/0118701 A1    May 3, 2018

Related U.S. Application Data

(63) Continuation of application No. 14/759,779, filed as application No. PCT/EP2013/077083 on Dec. 18, 2013, now Pat. No. 9,981,931.

(30) Foreign Application Priority Data

Jan. 9, 2013 (EP) ..................... 13150663
Dec. 2, 2013 (EP) ..................... 13195331
Dec. 12, 2013 (EP) ..................... 13196978

(51) Int. Cl.
C07D 301/02 (2006.01)
A01N 43/653 (2006.01)
C07D 249/08 (2006.01)

(52) U.S. Cl.
CPC ......... *C07D 301/02* (2013.01); *A01N 43/653* (2013.01); *C07D 249/08* (2013.01); *C07B 2200/13* (2013.01)

(58) Field of Classification Search
CPC .. C07D 301/02; C07D 249/08; A01N 43/653; C07B 2200/13
See application file for complete search history.

(56) References Cited

U.S. PATENT DOCUMENTS

| | | | |
|---|---|---|---|
| 4,242,121 A | 12/1980 | Hawkins et al. | |
| 4,599,362 A | 7/1986 | Nakatani et al. | |
| 4,940,720 A | 7/1990 | Nevill et al. | |
| 4,940,721 A | 7/1990 | Nevill et al. | |
| 4,945,100 A | 7/1990 | Nyefeler et al. | |
| 4,992,458 A | 2/1991 | Riebli et al. | |
| 5,143,932 A | 9/1992 | Jautelat et al. | |
| 5,162,358 A | 11/1992 | Jautelat et al. | |
| 8,492,312 B2 | 7/2013 | Thomas | |
| 8,546,577 B2 | 10/2013 | Jeschke et al. | |
| 2008/0108686 A1 | 5/2008 | Gewehr et al. | |
| 2009/0036509 A1 | 2/2009 | Gewehr et al. | |
| 2009/0286768 A1 | 11/2009 | Crew et al. | |
| 2010/0240619 A1 | 9/2010 | Gregory et al. | |
| 2014/0012855 A1 | 1/2014 | Firat et al. | |
| 2014/0127322 A1 | 5/2014 | Oberholzer et al. | |
| 2014/0128255 A1 | 5/2014 | Dietz et al. | |
| 2014/0155262 A1 | 6/2014 | Dietz et al. | |
| 2015/0250173 A1 | 9/2015 | Körber et al. | |

FOREIGN PATENT DOCUMENTS

| | | |
|---|---|---|
| AU | 611315 B2 | 6/1991 |
| CA | 1100976 A | 5/1981 |
| CA | 1187084 A | 5/1985 |
| CA | 1209152 A | 8/1986 |
| CA | 1210404 A | 8/1986 |
| CN | 101225074 A | 7/2008 |
| CS | 247200 B2 | 12/1986 |
| DE | 2325878 A1 | 12/1974 |
| DE | 3801233 A1 | 8/1988 |
| DE | 37 33 755 | 4/1989 |
| DE | 4003180 A1 | 8/1991 |
| EP | 0000017 B1 | 9/1981 |
| EP | 0077479 A2 | 4/1983 |
| EP | 0 113 640 | 4/1984 |
| EP | 0 126 430 | 11/1984 |
| EP | 0114567 B1 | 9/1988 |
| EP | 0275955 B1 | 7/1990 |
| EP | 0470466 A2 | 2/1992 |
| EP | 354183 B1 | 1/1993 |
| EP | 0354183 B1 | 1/1993 |

(Continued)

OTHER PUBLICATIONS

International Preliminary Report on Patentability dated 047/14/2015, prepared in International Application No. PCT/EP2013/077083.

International Search Report dated Apr. 4, 2014, prepared in International Application No. PCT/EP2013/077083.

European Search Report dated Jul. 12, 2013, prepared in EP 13150663.

Afon'Kin, A.A. et al. "Synthesis of Some Electron-Rich Aryl(hetaryl)oxarines under Phase-Transfer and Homogenous Conditions", Russian Journal of Organic Chemistry, 2008, p. 1776-1779, vol. 44, No. 12.

Brandes, Bridget D., et al., "Synthesis of enantiopure 3-chlorostyrene oxide via an asymmetric epoxidation-hydrolytic kinetic resolution sequence", Tetrahedron; Asymmetry, 1997, p. 3927-3933, vol. 8, No. 23.

(Continued)

*Primary Examiner* — John M Mauro
(74) *Attorney, Agent, or Firm* — Brinks Gilson & Lione

(57) ABSTRACT

The present invention relates to a process for the preparation of the compounds II

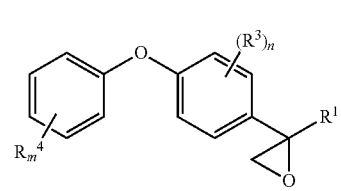

from the respective oxo compounds. Furthermore, he invention relates to a process for the preparation of triazole compounds from oxiranes II.

3 Claims, 2 Drawing Sheets

(56) References Cited

FOREIGN PATENT DOCUMENTS

| | | |
|---|---|---|
| EP | 0440950 B1 | 11/1993 |
| EP | 0 735 142 | 2/1996 |
| EP | 1431275 B1 | 4/2010 |
| EP | 2559688 A1 | 2/2013 |
| EP | 2835052 A1 | 2/2015 |
| FR | 2491924 A1 | 4/1982 |
| GB | 2064520 A1 | 6/1981 |
| GB | 2132195 A1 | 7/1984 |
| GB | 2143815 A1 | 2/1985 |
| JP | 59222434 A | 12/1984 |
| JP | 283304 A | 3/1990 |
| NZ | 230176 A | 1/1992 |
| WO | 96041804 A1 | 12/1996 |
| WO | WO 02/085891 | 10/2002 |
| WO | 03064572 A1 | 8/2003 |
| WO | 05123689 A1 | 12/2005 |
| WO | 05123690 A1 | 12/2005 |
| WO | 06015866 A1 | 2/2006 |
| WO | 06087373 A1 | 8/2006 |
| WO | 06109933 A1 | 10/2006 |
| WO | 06119876 A1 | 11/2006 |
| WO | 07031308 A2 | 3/2007 |
| WO | 07115644 A1 | 10/2007 |
| WO | 08082198 A1 | 7/2008 |
| WO | 10034737 A1 | 4/2010 |
| WO | 10146114 A1 | 12/2010 |
| WO | 11099804 A2 | 8/2011 |
| WO | 12035050 A2 | 3/2012 |
| WO | 12037782 A1 | 3/2012 |
| WO | 12084670 A1 | 6/2012 |
| WO | 12090515 A1 | 7/2012 |
| WO | 12092115 A1 | 7/2012 |
| WO | 12143317 A1 | 10/2012 |
| WO | 13010885 A1 | 1/2013 |
| WO | 13010894 A1 | 1/2013 |
| WO | WO 2013/010862 | 1/2013 |
| WO | WO 2013007767 | 1/2013 |
| WO | 13024075 A1 | 2/2013 |
| WO | 13024076 A1 | 2/2013 |
| WO | 13024077 A1 | 2/2013 |
| WO | 13024080 A1 | 2/2013 |
| WO | 13024081 A1 | 2/2013 |
| WO | 13024082 A1 | 2/2013 |
| WO | 13024083 A1 | 2/2013 |
| WO | 13189801 A1 | 12/2013 |
| WO | 14079719 A1 | 5/2014 |
| WO | 14079724 A1 | 5/2014 |
| WO | 14079728 A1 | 5/2014 |
| WO | 14079730 A1 | 5/2014 |
| WO | 14079752 A1 | 5/2014 |
| WO | 14079754 A1 | 5/2014 |
| WO | 14079764 A1 | 5/2014 |
| WO | 14079766 A1 | 5/2014 |
| WO | 14079769 A1 | 5/2014 |
| WO | 14079770 A1 | 5/2014 |
| WO | 14079771 A1 | 5/2014 |
| WO | 14079772 A1 | 5/2014 |
| WO | 14079773 A1 | 5/2014 |
| WO | 14079774 A1 | 5/2014 |
| WO | 14079804 A1 | 5/2014 |
| WO | 14079813 A1 | 5/2014 |
| WO | 14079814 A1 | 5/2014 |
| WO | 14079841 A1 | 5/2014 |
| WO | 14095932 A1 | 6/2014 |
| WO | 14095994 A1 | 6/2014 |
| WO | 15003908 A1 | 1/2015 |
| WO | 15055497 A1 | 4/2015 |
| WO | 15113860 A1 | 8/2015 |
| WO | 15135701 A1 | 9/2015 |
| WO | 15169711 A1 | 11/2015 |
| WO | 15189080 A1 | 12/2015 |
| WO | 15197393 A1 | 12/2015 |
| WO | 1614224 A1 | 1/2016 |
| WO | 16008740 A1 | 1/2016 |
| WO | 16078995 A1 | 5/2016 |
| WO | 16079043 A1 | 5/2016 |
| WO | 16128239 A1 | 8/2016 |
| WO | 16128240 A1 | 8/2016 |
| WO | 16128261 A2 | 8/2016 |
| WO | 16142456 A1 | 9/2016 |
| WO | 17001252 A1 | 1/2017 |

OTHER PUBLICATIONS

Forrester, Julie, et al. "Generation of trimethylsulfonium cation from dimethyl sulfoxide and dimethyl sulfate: implication s for the synthesis of epoxides from aldehydes and ketones", J. Chem. Soc. Perkin Trans. 1, 1995, pp. 2289-2291, vol. 1995.

Kuzenkov, A.V., "Synthesis of substituted 2-azoloyl-1-pyridylethan-1-ols", Chemistry of hererocyclic compounds, 2003, p. 1492-1495 vol. 39, No. 11.

Mosset, Paul et al. "Trimethylsulfonium Methylsulfate, a simple and efficient epoxidizing agent", Synthetic Communications, 1985, p. 749-757, vol. 15, No. 8.

Yu, Guan-Ping, et al. "Synthesis and fungicidal evaluation of 2-arylphenyl ether-3-(1H-1,2,4-triazol-1-yl)propan-2-ol Derivatives", J. Agric. Food Chem., 2009. p. 4854-4860, vol. 57.

Extended European Search Report prepared a corresponding European Application No. 17155867.9, dated Sep. 27, 2017.

Akama, Tsutomu, et al. "Discovery and structure-activity study of a novel benzoxaborole anti-inflammatory agent (AN2728) for the potential topical treatment of psoriasis and atopic dermatitis", Bioorganic & Medicinal Chemistry Letters, 2009, p. 2129-2132, vol. 19.

Database CA [Online], Chemical Abstracts Service, Columbus, Ohio, US, Crew, et al., "Substituted midazopyrazines and imidazotriazines as ACK1 inhibitors and their preparation" retrieved from STN Database accession No. 2009-1436665.

Database CA [Online], Chemical Abstracts Service, Columbus, Ohio, US, Schlafke, et al., "Phenoxy derivatives of trifluoromethylbenzene", retrieved from STN, Database accession No. 1975-170346.

Database CA [Online], Chemical Abstracts Service, Columbus, Ohio, US, Wan, et al., "Preparation of tricyclic compounds as Lp-PLA2 inhibitors", retrieved from STN, Database accession No. 2012-459740.

Final Office Action, issued in co-pending U.S. Appl. No. 14/653,578, dated Jul. 3, 2018.

Final Office Action, issued in co-pending U.S. Appl. No. 14/653,578, dated Apr. 28, 2017.

Final Office Action, issued in co-pending U.S. Appl. No. 14/902,877, dated Aug. 6, 2018.

Lima, Lidia Moreira et al., "Bioisosterism: A useful strategy for molecular Modification and drug design", Current Medicinal Chemistry, 2005, p. 23-49, vol. 12.

Office Action, issued in co-pending U.S. Appl. No. 14/653,578, dated Aug. 24, 2016.

Office Action, issued in co-pending U.S. Appl. No. 14/653,578, dated Oct. 24, 2017.

Office Action, issued in co-pending U.S. Appl. No. 14/653,578, dated Feb. 5, 2019.

Office Action, issued in co-pending U.S. Appl. No. 14/902,877, dated Mar. 8, 2018.

Office Action, issued in co-pending U.S. Appl. No. 15/739,876, dated Oct. 15, 2018.

PROCESS FOR THE PREPARATION OF SUBSTITUTED OXIRANES AND TRIAZOLES

CROSS-REFERENCE TO RELATED APPLICATIONS

This application is a continuation of U.S. application Ser. No. 14/759,779, filed Jul. 8, 2015, the entire contents of which is hereby incorporated herein by reference. U.S. application Ser. No. 14/759,779, is a National Stage application of International Application No. PCT/EP2013/077083, filed Dec. 18, 2013 the entire contents of which is hereby incorporated herein by reference. U.S. application Ser. No. 14/759,779 also claims priority under 35 U.S.C. § 119 to European Patent Application No. 13150663.6, filed Jan. 9, 2013; European Patent Application No. 13195331.7, filed Dec. 2, 2013; and European Patent Application No. 13196978.4, filed Dec. 12, 2013, the entire contents of which are hereby incorporated herein by reference.

DESCRIPTION

The present invention relates to a process for providing oxiranes using an aqueous solution of trimethylsulfonium methylsulfate in the presence of a base, and optionally further converting the resulting oxiranes into triazole compounds by reacting the substituted oxiranes with 1H-1,2,4-triazole under basic conditions. Further, the invention relates to a process for providing certain substituted triazoles. Furthermore, the invention relates to an aqueous reagent of trimethylsulfonium methylsulfate and its use for the conversion of oxo-groups into oxiranes.

The substituted oxiranes provided by the process according to the present invention are valuable intermediate compounds for the synthesis of triazole compounds having pesticidal, in particular fungicidal activity. Triazole compounds that are accessible via an oxirane intermediate are, for example described in WO 2013/010862 (PCT/EP2012/063526), WO 2013/010894 (PCT/EP2012/063635), WO 2013/010885 (PCT/EP2012/063620), WO 2013/024076 (PCT/EP2012/065835), WO 2013/024075 (PCT/EP2012/065834), WO 2013/024082 (PCT/EP2012/065850), WO 2013/024077 (PCT/EP2012/065836), WO 2013/024081 (PCT/EP2012/065848), WO 2013/024080 (PCT/EP2012/065847), WO 2013/024083 (PCT/EP2012/065852) and EP 2559688 (EP 11177556.5), that are directed to specific fungicidal substituted 2-[2-halogen-4-phenoxy-phenyl]-1-[1,2,4]triazol-1-yl-ethanol compounds. WO 2013/007767 (PCT/EP2012/063626) is directed to fungicidal substituted 2-[2-halogenalkyl-4-phenoxy-phenyl]-1-[1,2,4]triazol-1-yl-ethanol compounds, that can also be synthesized via a respective oxirane intermediate compound. A common process for the synthesis of oxiranes from carbonyl compounds such as aldehydes and ketones is the reaction with trimethylsulfonium iodide in the presence of a base (JACS 1965, 87, p 1353ff). This reagent is very expensive and not suitable for industrial scales. An alternative reagent is trimethylsulfonium methylsulfate that can be obtained from dimethylsulfide and dimethylsulfate (Heterocycles 8, 1977, p. 397 ff). However, this reagent (melting point 100 to 104° C.) is very hygroscopic and difficult to handle in solid form (Synth. Communications, 15, 1985, p 753). For example an exact dosage of said reagent is only possible under the exclusion of atmospheric humidity. In J. Agric. Food Chem. 2009, 57, 4854-4860 certain 2-arylphenyl-ether-3-(1H-1,2,4-triazol-1-yl)propan-2-ol derivatives are synthesized via an oxirane.

Synthetic Communications 15, 1985, p. 749ff. generally describes the reaction of trimethylsulfonium methyl sulfate with aldehydes and ketones using 50% NaOH solution. However, not with every ketone or aldehyde, satisfying yields can be achieved, in particular, aldehydes that are more reactive are reacted. According to this document, NaOH is used as base for the reaction and high amounts of water are used because the base is added as 50% aqueous solution. Furthermore, high excess of base and preferably methylenechloride are used in the process, which is not suitable for an industrial process also because of environmental issues.

A. A. Afonkin et al. In the Russian Journal of Organic Chemistry, vol. 44, no. 12, 2008, pp 1776 to 1779, is directed to the synthesis of some electron-rich aryl (heteroaryl) oxiranes under phase-transfer and homogenous conditions using trimethylsulfonium methyl sulfate as reagent. In this reference, the reaction of aldehydes is described that are generally more reactive than ketones. NaOH is used as 50% aqueous solution, i.e. high amounts of water are present.

DE3733755 is directed to a process for the preparation of 2-(4-chlorophenyl-ethyl)-2-tert-butyl-oxirane from the respective ketone using trimethylsulfonium methylfulfate in the presence of potassium hydroxide, dimethylsulfide and water. According to this document, the amount of water present in the reaction must be between 1.0 and 1.5 mole per mole of ketone, otherwise the yields are not high enough. Such restricted amounts of water are, however, not favorable for an industrial process.

Consequently, the methods known from the literature are sometimes not suitable for the efficient synthesis of substituted oxiranes because the yield is not sufficient and/or the reaction conditions and parameters such as water content and/or the proportion of the reactants and ingredients to each other are not suitable for an upscale to industrially relevant amounts. Inter alia because some oxiranes are valuable intermediates for the synthesis of triazole compounds with promising fungicidally activity, there is an ongoing need for improved processes that easily make such intermediates and compounds available.

An object of the present invention was to provide an improved process for the synthesis of oxiranes that are valuable intermediates for the preparation of fungicidal active triazole compounds starting from the respective oxo-group containing compounds. Furthermore, the object underlying the present invention was to optimize the synthesis of triazole active compounds using said oxiranes.

It has now surprisingly been found a highly efficient synthesis for the conversion of specific oxo-group containing compounds into oxiranes that are useful as intermediates in the synthesis of certain pesticidal triazole compounds.

Accordingly, one aspect of the present invention is a process for the preparation of compounds IIa

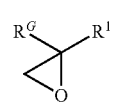

IIa wherein $R^G$ is optionally substituted aryl or heteroaryl and $R^1$ is as defined below;

comprising the following step:
(i) reacting an oxo compound of the formula IIIa

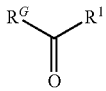                                    IIIa with trimethylsulfonium methylsulfate of the formula IV

                                    IV in aqueous solution in the presence of a base.

In particular, in the inventive process, compound IIa is oxirane compound II and compound IIIa is oxo-compound III. Consequently, the present invention particularly relates to a process for the preparation of the compounds II

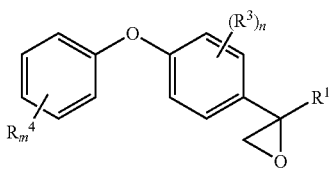                                    II comprising the following step:
(i) reacting an oxo compound of the formula III

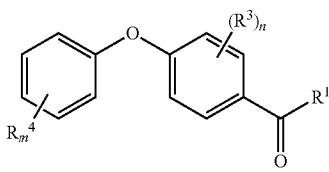                                    III with trimethylsulfonium methylsulfate of the formula IV

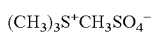                                    IV in aqueous solution in the presence of KOH, wherein 1 to 4, preferably more than 1.5 equivalents to 4 equivalents of water in relation to one equivalent of compound III are used, wherein the variables $R^1$, $R^3$, $R^4$, n and m are defined as follows:

$R^1$ is selected from $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkyl-$C_1$-$C_6$-alkyl, phenyl, phenyl-$C_1$-$C_4$-alkyl, phenyl-$C_2$-$C_4$-alkenyl or phenyl-$C_2$-$C_4$-alkynyl;

wherein the aliphatic moieties of $R^1$ are not further substituted or do carry one, two, three or up to the maximum possible number of identical or different groups $R^{12a}$ which independently are selected from:

$R^{12a}$ halogen, OH, CN, nitro, $C_1$-$C_4$-alkoxy, $C_3$-$C_8$-cycloalkyl, $C_3$-$C_8$-halocycloalkyl and $C_1$-$C_4$-halogenalkoxy;

wherein the cycloalkyl and/or phenyl moieties of $R^1$ are not further substituted or do carry one, two, three, four, five or up to the maximum number of identical or different groups $R^{12b}$ which independently are selected from:

$R^{12b}$ halogen, OH, CN, nitro, $C_1$-$C_4$-alkyl, $C_1$-$C_4$-alkoxy, $C_1$-$C_4$-halogenalkyl, $C_3$-$C_8$-cycloalkyl, $C_3$-$C_8$-halocycloalkyl and $C_1$-$C_4$-halogenalkoxy $R^3$ is independently selected from halogen, CN, $NO_2$, OH, SH, $C_1$-$C_6$-alkyl, $C_1$-$C_6$-alkoxy, $C_2$-$C_6$-alkenyl, $C_2$-$C_6$-alkynyl, $C_3$-$C_8$-cycloalkyl, $C_3$-$C_8$-cycloalkyloxy, $NH_2$, $NH(C_1$-$C_4$-alkyl), $N(C_1$-$C_4$-alkyl$)_2$, $NH(C_3$-$C_6$-cycloalkyl), $N(C_3$-$C_6$-cycloalkyl$)_2$, $S(O)_p(C_1$-$C_4$-alkyl), $C(=O)(C_1$-$C_4$-alkyl), $C(=O)(OH)$, $C(=O)(O-C_1$-$C_4$-alkyl), $C(=O)(NH(C_1$-$C_4$-alkyl))$, $C(=O)(N(C_1$-$C_4$-alkyl$)_2)$, $C(=O)(NH(C_3$-$C_6$-cycloalkyl))$ and $C(=O)-(N(C_3$-$C_6$-cycloalkyl$)_2)$; wherein each of $R^3$ is unsubstituted or further substituted by one, two, three or four $R^{3a}$; wherein p is 0, 1 or 2, and wherein $R^{3a}$ is independently selected from halogen, CN, $NO_2$, OH, $C_1$-$C_4$-alkyl, $C_1$-$C_4$-haloalkyl, $C_3$-$C_8$-cycloalkyl, $C_3$-$C_8$-halocycloalkyl, $C_1$-$C_4$-alkoxy and $C_1$-$C_4$-haloalkoxy;

$R^4$ is independently selected from the substituents as defined for $R^3$, wherein said $R^4$ are unsubstituted or further substituted by one, two, three or four $R^{4a}$, wherein each $R^{4a}$ is independently selected from the substituents as defined for $R^{3a}$;

n is 0, 1, 2, 3 or 4; and
m is 0, 1, 2, 3, 4 or 5.

More specifically, compounds II and III are the following:

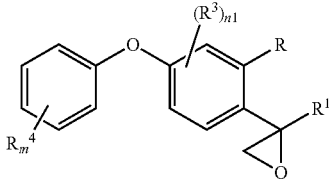                                    II-A

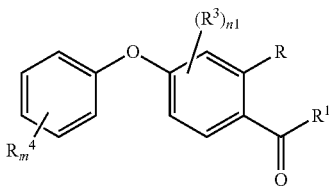                                    III-A wherein R is selected from halogen and $(C_1$-$C_2)$-haloalkyl, in particular Cl, Br, F or $CF_3$, more specifically Cl or $CF_3$, and $R^1$, $R^3$, $R^4$ and m are as defined and preferably defined herein, and n1 is 0, 1, 2 or 3.

In one embodiment, the compounds of formula III are of sub formula IIIA

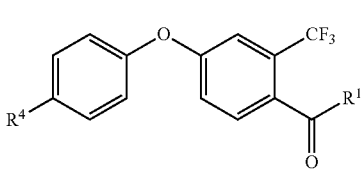                                    IIIA wherein $R^1$ is $C_1$-$C_6$-alkyl or $C_3$-$C_8$-cycloalkyl and $R^4$ is F or Cl.

According to one embodiment, $R^1$ is $C_1$-$C_6$-alkyl, more specifically $C_1$-$C_4$-alkyl, in particular selected from $CH_3$, $C_2H_5$, n-$C_3H_7$, $CH(CH_3)_2$, n-butyl, iso-butyl and tert-butyl, more particularly selected from $CH_3$, $C_2H_5$, $CH(CH_3)_2$ and $C(CH_3)_3$. According to a further embodiment, $R^1$ is $C_3$-$C_8$-cycloalkyl, in particular $C_3$-$C_6$-cycloalkyl, such as $C_3H_5$ (cyclopropyl), $C_4H_7$ (cyclobutyl), cyclopentyl or cyclohexyl. A further embodiment relates to compounds, wherein $R^1$ is $C_3H_5$ (cyclopropyl) or $C_4H_7$ (cyclobutyl).

$R^4$ is F or Cl, in particular Cl.

In particular, $R^1$ is selected from $CH_3$, $CH(CH_3)_2$ and cyclopropyl and $R^4$ is Cl.

This embodiment applies to formula II and I accordingly:

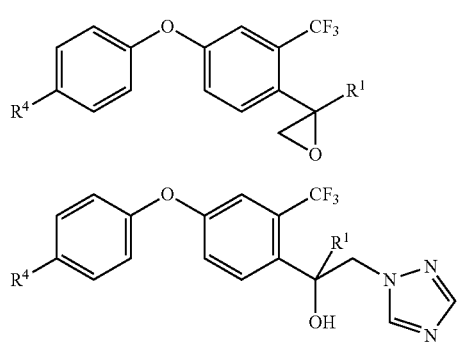

with the above meanings of $R^1$ and $R^4$.

In the process step (i) according to the present invention, an oxo compound of the formula III is reacted with trimethylsulfonium methylsulfate of the formula IV

$$(CH_3)_3S^+CH_3SO_4^- \qquad IV$$

in aqueous solution in the presence of a base.

Preferably, in the inventive process, 1 to 4 equivalents, in particular 1.2 to 3.5 eq, more specifically 1.5 to 3.3 eq, of water in relation to one equivalent of compound III are used. It may be favorable, if more than 1.5 eq of water, in particular more than 1.5 eq of water to 4 eq of water, more specifically more than 1.5 eq to 3.5 eq of water, even more particularly more than 1.5 eq water to 2.5 eq water per mole of compound III. In particular the ratios of 1.6 to 3.8, more specifically 1.7 to 3.3 eq, more specifically 1.8 to 2.8 eq or 1.9 to 2.5 of water per mole of compound III may be favorable according to the present invention.

The reagent IV is preferably used in an amount of 1.1 to 2.5, in particular 1.2 to 2, more specifically 1.3 to 1.6 equivalents of IV per 1 equivalent (mole) of compound III.

In general, the reagent of formula IV can be prepared from dimethylsulfide and dimethylsulfate. According to one embodiment of the invention, reagent IV is prepared in-situ by adding dimethylsulfate to the reaction mixture containing dimethylsulfide. The dimethylsulfide is usually used in excess.

It is preferred according to the present invention to use as reagent IV an aqueous solution of trimethylsulfonium methylsulfate III containing 33 to 37 wt %, preferably 34 to 36 wt %, more specifically 34 to 35.3 wt %, also more specifically 34.3 to 35.9 wt %, of trimethylsulfonium kation.

Such stable aqueous solutions of the reagents are novel. Thus, according to a further aspect, the present invention relates to an aqueous solution of trimethylsulfonium methylsulfate III containing 33 to 37 wt %, preferably 34 to 36 wt %, more specifically 34 to 35.3 wt %, also more specifically 34.3 to 35.9 wt %, of trimethylsulfonium kation.

In particular, the inventive reagent IV solution contains 33 to 37 wt %, preferably 34 to 36 wt %, more specifically 34 to 35.3 wt %, also more specifically 34.3 to 35.9 wt %, of trimethylsulfonium kation. Accordingly, the amount of trimethylsulfonium-methylsulfate in the reagent, measured as summation of trimethsulfonium-cation and methylsulfate-anion, is about 80 to 90 wt %, preferably about 83 to 88 wt-%, more specifically about 83 to 86 wt-%. The quantification can be, for example, accomplished by means of quantitative NMR-spectroscopie.

The viscosity of the aqueous reagent IV solution of the invention is comparatively low. The inventive solutions are stable at room temperature, in particular at 25° C., and can be stored over a longer time. In particular, the inventive reagent solution does not crystallize out during storage over a longer time, such as several weeks, e.g. up to 12 weeks, at temperatures of 10 to 25° C.

The reagent can be prepared by adding dimethylsulfate to water and dimethylsulfide. Dimethylsulfide is normally used in excess, generally 2 to 8, more preferably 4 to 6, more specifically 4.5 to 5.5, equivalents.

In the preparation of the aqueous solution of reagent IV according to the invention, preferably 1.3 to 2.2 eq, more preferably 1.45 to 2.0 eq, water in relation to the dimethylsulfate are used.

Preferably, the temperature of the reaction mixture when adding the dimethylsulfate is room temperature, in particular 25° C. to 40° C.

The aqueous reagent separates as the lower phase and can be further used as such.

Following the state of the art, it was not possible to provide stable aqueous solutions of reagent IV that can be used in process for the synthesis of oxiranes from oxo-group containing compounds. It has now surprisingly been found within the framework of the present invention that stable aqueous solution of reagent IV can be provided if specific ranges of water as defined above in relation to the dimethylsulfate are kept.

Thus, another aspect of the invention is the general use of the inventive aqueous solution of trimethylsulfonium methylsulfate IV for the synthesis of an oxirane from the respective oxo compound, in particular a compound IIa from a compounds IIIa, more specifically a compound II from a compound III as defined herein.

The use of the inventive aqueous solution of the reagent IV has been proven very efficient also for upscaled reaction conditions, since it is stable and since it contains a defined amount of reagent, so that reagent IV can be easily and precisely dosed to the reaction mixture.

Thus it is a preferred embodiment, if in step (i) of the inventive process, the reagent IV is added as an aqueous solution of trimethylsulfonium methylsulfate III containing 33 to 37 wt %, preferably 34 to 36 wt %, more specifically 34 to 35.3 wt %, also more specifically 34.3 to 35.9 wt % of trimethylsulfonium kation or any preferred embodiment thereof defined herein.

The base used in step (i) according to the invention is preferably selected from KOH and NaOH In a preferred embodiment, KOH is used and specifically, it is used in solid form, preferably as solid pellets, flakes, microprills and/or powder. It is preferred if at least 3 equivalents of base, preferably at least 3.2 eq, more specifically at least 3.4 eq per 1 equivalent of compound III are used. It may be preferred if the amount of base is 3 to 6 eq, more specifically 3 to 5 eq per mole of compound III.

The base, in particular solid KOH, is used such that the inventive range of water present in the reaction is kept. Then, some of the base is dissolved in the reaction solution and some is still present in solid form during the reaction.

According to one embodiment of the inventive process, dimethylsulfide is also used as solvent in step (i). According to a further embodiment, an additional solvent is used. In particular, an aprotic organic solvent is suitable, such as for example diethylether, methyl-tert-butylether, chlorobenzene, xylene or toluene.

The reaction temperature in step (i) is preferably held at a maximum of 50° C., in particular at a maximum of 45, more preferably at a maximum of 40° C. Generally, it is also preferred to have a reaction temperature of at least 20° C., in particular at least room temperature, in particular at least 25° C. In a further embodiment, the temperature is at least 30° C. It may be preferred if the temperature is at least 35° C.

By means of the inventive process, the oxiranes of formula II can be prepared in high yields. Preferably, the yields are at least 60%, more preferably 70%, even more preferred at least 75%, even more preferred at least 80%.

The order of adding the reactants to the reaction mixture is variable. In one embodiment, the base is added to the solution of compound III and solvent first and then reagent IV is added. According to another embodiment, the reagent IV is added first to the solution of compound III and then the base is added. According to a further embodiment, a solution of compound III and the reagent IV are added simultaneously to the base. In the latter embodiment, the base is preferably suspended in sufficient solvent and is stirred during the addition of the reagents.

The oxirane obtained according to the inventive process (step (i)) can be further converted into a triazole of formula I. Consequently, according to a further embodiment of the invention, the process further comprises the following step:
(ii) reacting the oxirane of the formula II resulting from step (i) with 1H-1,2,4-triazole and an inorganic base, resulting in compounds of formula I,

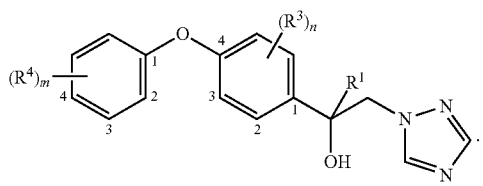

In step (ii), the oxirane is reacted with 1H-1,2,4-triazole and an inorganic base.

The inorganic base used in step (ii) is preferably selected from NaOH, KOH, $Na_2CO_3$ and $K_2CO_3$, more specifically from NaOH and KOH. According to one embodiment, NaOH is used. According to a further embodiment, KOH is used.

According to a specific embodiment, the sodium salt of 1H-1,2,4-triazole as a base is used, wherein said sodium salt is prepared using triazole and a base preferably selected from NaOH, NaH and Na-alcoholates. See also DE 3042302.

The amount of base used in step (ii) is preferably equal to or less than 1 eq, in particular less than 1 eq, more preferably equal to or less than 0.8 eq, even more preferably equal to or less than 0.6 equivalents per 1 equivalent of compound II. Also preferred are amounts of base being equal to or less than 0.4 equivalents, in particular equal to or less than 0.2 equivalents, specifically equal to or less than 0.1 eq per 1 equivalent of compound II. Preferably, at least 0.1 eq, more preferably at least 0.2 equivalents, in particular at least 0.3, more specifically at least 0.4 eq base per 1 equivalent of compound II are used.

It has surprisingly been found according to the invention, that higher yields of compounds I can be achieved, if less than 1 eq of base is used in relation to the compound II. In specific embodiments thereof, NaOH is used in as base, preferably in an amount as given above, in particular in an amount of 0.1 to 0.55 eq in relation to the oxirane of formula II.

In order to have preferably low reaction times, temperatures of at least 100° C., more preferably at least 110° C., in particular at least 120° C. are favorable. It is also an embodiment to reflux the reaction mixture. Preferably, the reaction temperature is not higher than 150° C., in particular not higher than 140° C. Specifically, a reaction temperature of 120° C. to 140° C. is used.

The amount of 1H-1,2,4-triazole used in step (ii) generally is at least 1 eq per mole of oxirane II. According to one embodiment, the 1H-1,2,4-triazole is used in excess in relation to the oxirane II. Preferred are more than 1 eq to 2 eq, more preferably more than 1 eq to 1.8 eq, even more preferred more than 1 eq to 1.6 eq. Mostly for economic reason, it can be preferred to use at least 1.1 eq, specifically 1.15 eq, to 1.5 eq of triazole in relation to oxirane II.

The solvent used in step (ii) is preferably selected from dimethylformamide, dimethylacetamide, N-metylpyrrolidone. Most preferred is dimethylformamide.

One side product that may occur, if $R^1$ is iso-propyl is the following compound II", more specifically IIa":

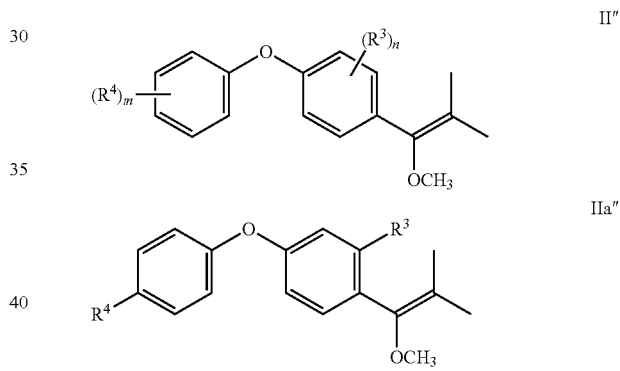

wherein $R^3$, $R^4$, n and m are defined above. In particular, in formula IIa", $R^3$ is $CF_3$ or Cl and $R^4$ is Cl.

According to the inventive process conditions, the side product can be repressed or avoided and higher yields can be obtained.

Generally, one further undesired side product in the synthesis of compounds I that may occur in undesired amounts is the symmetric triazole I" that is formed together with the desired triazole of formula I, sometimes in high excess compared to the desired compound I, leading, consequently, to lower yields of the desired product of formula I.

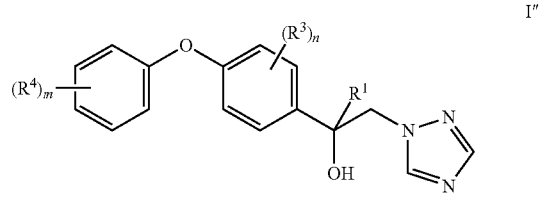

wherein $R^1$, $R^3$, $R^4$, n and m are defined above. In particular Ia″ may occur, wherein $R^3$ is $R^3$ is $CF_3$ or Cl and $R^4$ is Cl and $R^1$ is as defined and preferably defined herein:

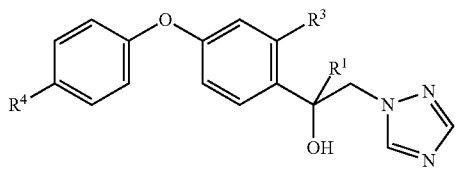

Ia″

Particular side products Ia″ that may occur during the inventive process depending on the substituents in the reagents are compiled in Table S1. Each line of lines S1-1 to S1-320 of Table S1 corresponds to a side product Ia″ having the substituents specified in the respective line:

TABLE S1

| I″ No. | $R^4$ | $R^3$ | $R^1$ |
|---|---|---|---|
| S1-1 | Cl | $CF_3$ | H |
| S1-2 | Cl | $CF_3$ | $CH_3$ |
| S1-3 | Cl | $CF_3$ | $CH_2CH_3$ |
| S1-4 | Cl | $CF_3$ | $CH_2CH_2CH_3$ |
| S1-5 | Cl | $CF_3$ | $CH(CH_3)_2$ |
| S1-6 | Cl | $CF_3$ | $C(CH_3)_3$ |
| S1-7 | Cl | $CF_3$ | $CH(CH_3)CH_2CH_3$ |
| S1-8 | Cl | $CF_3$ | $CH_2CH(CH_3)_2$ |
| S1-9 | Cl | $CF_3$ | $CH_2CH_2CH_2CH_3$ |
| S1-10 | Cl | $CF_3$ | $CF_3$ |
| S1-11 | Cl | $CF_3$ | $CHF_2$ |
| S1-12 | Cl | $CF_3$ | $CH_2F$ |
| S1-13 | Cl | $CF_3$ | $CHCl_2$ |
| S1-14 | Cl | $CF_3$ | $CH_2Cl$ |
| S1-15 | Cl | $CF_3$ | $CH_2OH$ |
| S1-16 | Cl | $CF_3$ | $CH_2CH_2OH$ |
| S1-17 | Cl | $CF_3$ | $CH_2CH_2CH_2OH$ |
| S1-18 | Cl | $CF_3$ | $CH(CH_3)CH_2OH$ |
| S1-19 | Cl | $CF_3$ | $CH_2CH(CH_3)OH$ |
| S1-20 | Cl | $CF_3$ | $CH_2CH_2CH_2CH_2OH$ |
| S1-21 | Cl | $CF_3$ | $CH(CH_3)CN$ |
| S1-22 | Cl | $CF_3$ | $CH_2CH_2CN$ |
| S1-23 | Cl | $CF_3$ | $CH_2CN$ |
| S1-24 | Cl | $CF_3$ | $CH_2CH_2CN$ |
| S1-25 | Cl | $CF_3$ | $CH_2CH_2CH_2CN$, |
| S1-26 | Cl | $CF_3$ | $CH(CH_3)CH_2CN$ |
| S1-27 | Cl | $CF_3$ | $CH_2CH(CH_3)CN$ |
| S1-28 | Cl | $CF_3$ | $CH_2CH_2CH_2CH_2CN$ |
| S1-29 | Cl | $CF_3$ | $CH_2OCH_3$ |
| S1-30 | Cl | $CF_3$ | $CH_2OCH_2CH_3$ |
| S1-31 | Cl | $CF_3$ | $CH(CH_3)OCH_3$ |
| S1-32 | Cl | $CF_3$ | $CH(CH_3)OCH_2CH_3$ |
| S1-33 | Cl | $CF_3$ | $CH_2CH_2OCH_2CH_3$ |
| S1-34 | Cl | $CF_3$ | $CH_2OCF_3$ |
| S1-35 | Cl | $CF_3$ | $CH_2CH_2OCF_3$ |
| S1-36 | Cl | $CF_3$ | $CH_2OCCl_3$ |
| S1-37 | Cl | $CF_3$ | $CH_2CH_2OCCl_3$ |
| S1-38 | Cl | $CF_3$ | $CH=CH_2$ |
| S1-39 | Cl | $CF_3$ | $CH_2CH=CH_2$ |
| S1-40 | Cl | $CF_3$ | $CH_2CH=CHCH_3$ |
| S1-41 | Cl | $CF_3$ | $CH_2C(CH_3)=CH_2$ |
| S1-42 | Cl | $CF_3$ | $CH_2C(CH_3)=CHCH_3$ |
| S1-43 | Cl | $CF_3$ | $CH_2C(CH_3)=C(CH_3)_2$ |
| S1-44 | Cl | $CF_3$ | $CH=CHCH_3$ |
| S1-45 | Cl | $CF_3$ | $C(CH_3)=CH_2$ |
| S1-46 | Cl | $CF_3$ | $CH=C(CH_3)_2$ |
| S1-47 | Cl | $CF_3$ | $C(CH_3)=C(CH_3)_2$ |
| S1-48 | Cl | $CF_3$ | $C(CH_3)=CH(CH_3)$ |
| S1-49 | Cl | $CF_3$ | $C(Cl)=CH_2$ |
| S1-50 | Cl | $CF_3$ | $C(H)=CHCl$ |
| S1-51 | Cl | $CF_3$ | $C(Cl)=CHCl$ |
| S1-52 | Cl | $CF_3$ | $CH=CCl_2$ |
| S1-53 | Cl | $CF_3$ | $C(Cl)=CCl_2$ |
| S1-54 | Cl | $CF_3$ | $C(H)=CH(F)$ |
| S1-55 | Cl | $CF_3$ | $C(H)=CF_2$ |
| S1-56 | Cl | $CF_3$ | $C(F)=CF_2$ |
| S1-57 | Cl | $CF_3$ | $C(F)=CHF$ |
| S1-58 | Cl | $CF_3$ | $CH=CHCH_2OH$ |
| S1-59 | Cl | $CF_3$ | $CH=CHOCH_3$ |
| S1-60 | Cl | $CF_3$ | $CH=CHCH_2OCH_3$ |
| S1-61 | Cl | $CF_3$ | $CH=CHCH_2OCF_3$ |
| S1-62 | Cl | $CF_3$ | $CH=CHCH_2OCCl_3$ |
| S1-63 | Cl | $CF_3$ | $CH=CH(C_3H_5)$ |
| S1-64 | Cl | $CF_3$ | $CH=CH(C_4H_7)$ |
| S1-65 | Cl | $CF_3$ | $CH=CH(1-Cl—C_3H_4)$ |
| S1-66 | Cl | $CF_3$ | $CH=CH(1-F-C_3H_4)$ |
| S1-67 | Cl | $CF_3$ | $CH=CH(1-Cl—C_4H_6)$ |
| S1-68 | Cl | $CF_3$ | $CH=CH(1-F-C_4H_6)$ |
| S1-69 | Cl | $CF_3$ | $C\equiv CH$ |
| S1-70 | Cl | $CF_3$ | $C\equiv CCH_3$ |
| S1-71 | Cl | $CF_3$ | $CH_2C\equiv CCH_3$ |
| S1-72 | Cl | $CF_3$ | $CH_2C\equiv CH$ |
| S1-73 | Cl | $CF_3$ | $CH_2C\equiv CCH_2CH_3$ |
| S1-74 | Cl | $CF_3$ | $C\equiv CCH(CH_3)_2$ |
| S1-75 | Cl | $CF_3$ | $C\equiv CC(CH_3)_3$ |
| S1-76 | Cl | $CF_3$ | $C\equiv C(C_3H_5)$ |
| S1-77 | Cl | $CF_3$ | $C\equiv C(C_4H_7)$ |
| S1-78 | Cl | $CF_3$ | $C\equiv C(1-Cl—C_3H_4)$ |
| S1-79 | Cl | $CF_3$ | $C\equiv C(1-Cl—C_4H_6)$ |
| S1-80 | Cl | $CF_3$ | $C\equiv CCl$ |
| S1-81 | Cl | $CF_3$ | $C\equiv CBr$ |
| S1-82 | Cl | $CF_3$ | $C\equiv C—I$ |
| S1-83 | Cl | $CF_3$ | $CH_2C\equiv CCl$ |
| S1-84 | Cl | $CF_3$ | $CH_2C\equiv CBr$ |
| S1-85 | Cl | $CF_3$ | $CH_2C\equiv C—I$ |
| S1-86 | Cl | $CF_3$ | $C\equiv CCH_2OCH_3$ |
| S1-87 | Cl | $CF_3$ | $C\equiv CCH(OH)CH_3$ |
| S1-88 | Cl | $CF_3$ | $C\equiv CCH(OCH_3)CH_3$ |
| S1-89 | Cl | $CF_3$ | $C\equiv COCH_3$ |
| S1-90 | Cl | $CF_3$ | $CH_2C\equiv COCH_3$ |
| S1-91 | Cl | $CF_3$ | $C\equiv CCH_2OCCl_3$ |
| S1-92 | Cl | $CF_3$ | $C\equiv CCH_2OCF_3$ |
| S1-93 | Cl | $CF_3$ | $C\equiv CCH_2(C_3H_5)$ |
| S1-94 | Cl | $CF_3$ | $C\equiv CCH_2(C_4H_7)$ |
| S1-95 | Cl | $CF_3$ | $C\equiv C(1-Cl—C_3H_4)$ |
| S1-96 | Cl | $CF_3$ | $C\equiv C(1-F—C_3H_4)$ |
| S1-97 | Cl | $CF_3$ | $C\equiv C(1-Cl—C_4H_6)$ |
| S1-98 | Cl | $CF_3$ | $C\equiv C(1-F—C_4H_6)$ |
| S1-99 | Cl | $CF_3$ | $C_3H_5$ (cyclopropyl) |
| S1-100 | Cl | $CF_3$ | $C_4H_7$ (cyclobutyl) |
| S1-101 | Cl | $CF_3$ | $C_5H_9$ (cyclopentyl) |
| S1-102 | Cl | $CF_3$ | cyclohexyl |
| S1-103 | Cl | $CF_3$ | $CH(CH_3)$—$C_3H_5$ ($CH(CH_3)$-cyclopropyl) |
| S1-104 | Cl | $CF_3$ | $CH_2$—$C_3H_5$ ($CH_2$-cyclopropyl) |
| S1-105 | Cl | $CF_3$ | 1-(Cl)-cyclopropyl |
| S1-106 | Cl | $CF_3$ | 1-(F)-cyclopropyl |
| S1-107 | Cl | $CF_3$ | 1-($CH_3$)-cyclopropyl |
| S1-108 | Cl | $CF_3$ | 1-(CN)-cyclopropyl |
| S1-109 | Cl | $CF_3$ | 2-(Cl)-cyclopropyl |
| S1-110 | Cl | $CF_3$ | 2-(F)-cyclopropyl |
| S1-111 | Cl | $CF_3$ | 1-(Cl)-cyclobutyl |
| S1-112 | Cl | $CF_3$ | 1-(F)-cyclobutyl |
| S1-113 | Cl | $CF_3$ | 2-(Cl)-cyclobutyl |
| S1-114 | Cl | $CF_3$ | 3-(Cl)-cyclobutyl |
| S1-115 | Cl | $CF_3$ | 2-(F)-cyclobutyl |
| S1-116 | Cl | $CF_3$ | 3-(F)-cyclobutyl |
| S1-117 | Cl | $CF_3$ | 3,3-$Cl_2$-cyclobutyl |
| S1-118 | Cl | $CF_3$ | 3,3-$F_2$-cyclobutyl |
| S1-119 | Cl | $CF_3$ | 2-($CH_3$)-cyclopropyl |
| S1-120 | Cl | $CF_3$ | 1-($CH_3$)-cyclobutyl |
| S1-121 | Cl | Cl | 2-($CH_3$)-cyclobutyl |
| S1-122 | Cl | Cl | 3-($CH_3$)-cyclobutyl |
| S1-123 | Cl | Cl | 3,3-($CH_3$)$_2$-cyclobutyl |
| S1-124 | Cl | Cl | 2-(CN)-cyclopropyl |
| S1-125 | Cl | Cl | 1-cyclopropyl-cyclopropyl |
| S1-126 | Cl | Cl | 2-cyclopropyl-cyclopropyl |
| S1-127 | Cl | Cl | $CH(CH_3)$(cyclobutyl) |
| S1-128 | Cl | Cl | $CH_2$-(cyclobutyl) |
| S1-129 | Cl | Cl | $CH_2CH_2$-(cyclopropyl) |
| S1-130 | Cl | Cl | $CH_2CH_2$-(cyclobutyl) |
| S1-131 | Cl | Cl | $CH_2$-(1-Cl-cyclopropyl) |
| S1-132 | Cl | Cl | $CH_2$-(1-F-cyclopropyl) |

TABLE S1-continued

| I'' No. | R⁴ | R³ | R¹ |
|---|---|---|---|
| S1-133 | Cl | Cl | CH₂-(1-Cl-cyclobutyl) |
| S1-134 | Cl | Cl | CH₂-(1-F-cyclobutyl) |
| S1-135 | Cl | Cl | CHCH₃-(1-Cl-cyclopropyl) |
| S1-136 | Cl | Cl | C(CH₃)₂-(1-F-cyclopropyl) |
| S1-137 | Cl | Cl | C₆H₅ |
| S1-138 | Cl | Cl | 4-Cl—C₆H₄ |
| S1-139 | Cl | Cl | 4-OCH₃—C₆H₄ |
| S1-140 | Cl | Cl | 4-CH₃—C₆H₄ |
| S1-141 | Cl | Cl | 4-F—C₆H₄ |
| S1-142 | Cl | Cl | 2,4-F₂—C₆H₃ |
| S1-143 | Cl | Cl | 2,4-Cl₂—C₆H₃ |
| S1-144 | Cl | Cl | 2-CH₃—C₆H₄ |
| S1-145 | Cl | Cl | 2-CF₃—C₆H₄ |
| S1-146 | Cl | Cl | 4-CH₃—C₆H₄ |
| S1-147 | Cl | Cl | 4-CF₃—C₆H₄ |
| S1-148 | Cl | Cl | 2-OCH₃—C₆H₄ |
| S1-149 | Cl | Cl | 2-OCF₃—C₆H₄ |
| S1-150 | Cl | Cl | 4-OCH₃—C₆H₄ |
| S1-151 | Cl | Cl | 4-OCF₃—C₆H₄ |
| S1-152 | Cl | Cl | 2,4,6-F₃—C₆H₂ |
| S1-153 | Cl | Cl | 2,4,6-Cl₃—C₆H₂ |
| S1-154 | Cl | Cl | CH₂C₆H₅ |
| S1-155 | Cl | Cl | CH₂—(4-Cl)—C₆H₄ |
| S1-156 | Cl | Cl | CH₂—(4-CH₃)—C₆H₄ |
| S1-157 | Cl | Cl | CH₂—(4-OCH₃)—C₆H₄ |
| S1-158 | Cl | Cl | CH₂—(4-F)—C₆H₄ |
| S1-159 | Cl | Cl | CH₂—(2,4-Cl₂)—C₆H₃ |
| S1-160 | Cl | Cl | CH₂—(2,4-F₂)—C₆H₃ |
| S1-161 | Cl | Cl | H |
| S1-162 | Cl | Cl | CH₃ |
| S1-163 | Cl | Cl | CH₂CH₃ |
| S1-164 | Cl | Cl | CH₂CH₂CH₃ |
| S1-165 | Cl | Cl | CH(CH₃)₂ |
| S1-166 | Cl | Cl | C(CH₃)₃ |
| S1-167 | Cl | Cl | CH(CH₃)CH₂CH₃ |
| S1-168 | Cl | Cl | CH₂CH(CH₃)₂ |
| S1-169 | Cl | Cl | CH₂CH₂CH₂CH₃ |
| S1-170 | Cl | Cl | CF₃ |
| S1-171 | Cl | Cl | CHF₂ |
| S1-172 | Cl | Cl | CH₂F |
| S1-173 | Cl | Cl | CHCl₂ |
| S1-174 | Cl | Cl | CH₂Cl |
| S1-175 | Cl | Cl | CH₂OH |
| S1-176 | Cl | Cl | CH₂CH₂OH |
| S1-177 | Cl | Cl | CH₂CH₂CH₂OH |
| S1-178 | Cl | Cl | CH(CH₃)CH₂OH |
| S1-179 | Cl | Cl | CH₂CH(CH₃)OH |
| S1-180 | Cl | Cl | CH₂CH₂CH₂CH₂OH |
| S1-181 | Cl | Cl | CH(CH₃)CN |
| S1-182 | Cl | Cl | CH₂CH₂CN |
| S1-183 | Cl | Cl | CH₂CN |
| S1-184 | Cl | Cl | CH₂CH₂CN |
| S1-185 | Cl | Cl | CH₂CH₂CH₂CN, |
| S1-186 | Cl | Cl | CH(CH₃)CH₂CN |
| S1-187 | Cl | Cl | CH₂CH(CH₃)CN |
| S1-188 | Cl | Cl | CH₂CH₂CH₂CH₂CN |
| S1-189 | Cl | Cl | CH₂OCH₃ |
| S1-190 | Cl | Cl | CH₂OCH₂CH₃ |
| S1-191 | Cl | Cl | CH(CH₃)OCH₃ |
| S1-192 | Cl | Cl | CH(CH₃)OCH₂CH₃ |
| S1-193 | Cl | Cl | CH₂CH₂OCH₂CH₃ |
| S1-194 | Cl | Cl | CH₂OCF₃ |
| S1-195 | Cl | Cl | CH₂CH₂OCF₃ |
| S1-196 | Cl | Cl | CH₂OCCl₃ |
| S1-197 | Cl | Cl | CH₂CH₂OCCl₃ |
| S1-198 | Cl | Cl | CH=CH₂ |
| S1-199 | Cl | Cl | CH₂CH=CH₂ |
| S1-200 | Cl | Cl | CH₂CH=CHCH₃ |
| S1-201 | Cl | Cl | CH₂C(CH₃)=CH₂ |
| S1-202 | Cl | Cl | CH₂C(CH₃)=CHCH₃ |
| S1-203 | Cl | Cl | CH₂C(CH₃)=C(CH₃)₂ |
| S1-204 | Cl | Cl | CH=CHCH₃ |
| S1-205 | Cl | Cl | C(CH₃)=CH₂ |
| S1-206 | Cl | Cl | CH=C(CH₃)₂ |
| S1-207 | Cl | Cl | C(CH₃)=C(CH₃)₂ |
| S1-208 | Cl | Cl | C(CH₃)=CH(CH₃) |
| S1-209 | Cl | Cl | C(Cl)=CH₂ |
| S1-210 | Cl | Cl | C(H)=CHCl |
| S1-211 | Cl | Cl | C(Cl)=CHCl |
| S1-212 | Cl | Cl | CH=CCl₂ |
| S1-213 | Cl | Cl | C(Cl)=CCl₂ |
| S1-214 | Cl | Cl | C(H)=CH(F) |
| S1-215 | Cl | Cl | C(H)=CF₂ |
| S1-216 | Cl | Cl | C(F)=CF₂ |
| S1-217 | Cl | Cl | C(F)=CHF |
| S1-218 | Cl | Cl | CH=CHCH₂OH |
| S1-219 | Cl | Cl | CH=CHOCH₃ |
| S1-220 | Cl | Cl | CH=CHCH₂OCH₃ |
| S1-221 | Cl | Cl | CH=CHCH₂OCF₃ |
| S1-222 | Cl | Cl | CH=CHCH₂OCCl₃ |
| S1-223 | Cl | Cl | CH=CH(C₃H₅) |
| S1-224 | Cl | Cl | CH=CH(C₄H₇) |
| S1-225 | Cl | Cl | CH=CH(1-Cl—C₃H₄) |
| S1-226 | Cl | Cl | CH=CH(1-F—C₃H₄) |
| S1-227 | Cl | Cl | CH=CH(1-Cl—C₄H₆) |
| S1-228 | Cl | Cl | CH=CH(1-F—C₄H₆) |
| S1-229 | Cl | Cl | C≡CH |
| S1-230 | Cl | Cl | C≡CCH₃ |
| S1-231 | Cl | Cl | CH₂C≡CCH₃ |
| S1-232 | Cl | Cl | CH₂C≡CH |
| S1-233 | Cl | Cl | CH₂C≡CCH₂CH₃ |
| S1-234 | Cl | Cl | C≡CCH(CH₃)₂ |
| S1-235 | Cl | Cl | C≡CC(CH₃)₃ |
| S1-236 | Cl | Cl | C≡C(C₃H₅) |
| S1-237 | Cl | Cl | C≡C(C₄H₇) |
| S1-238 | Cl | Cl | C≡C(1-Cl—C₃H₄) |
| S1-239 | Cl | Cl | C≡C(1-Cl—C₄H₆) |
| S1-240 | Cl | Cl | C≡CCl |
| S1-241 | Cl | Cl | C≡CBr |
| S1-242 | Cl | Cl | C≡C—I |
| S1-243 | Cl | Cl | CH₂C≡CCl |
| S1-244 | Cl | Cl | CH₂C≡CBr |
| S1-245 | Cl | Cl | CH₂C≡C—I |
| S1-246 | Cl | Cl | C≡CCH₂OCH₃ |
| S1-247 | Cl | Cl | C≡CCH(OH)CH₃ |
| S1-248 | Cl | Cl | C≡CCH(OCH₃)CH₃ |
| S1-249 | Cl | Cl | C≡COCH₃ |
| S1-250 | Cl | Cl | CH₂C≡COCH₃ |
| S1-251 | Cl | Cl | C≡CCH₂OCCl₃ |
| S1-252 | Cl | Cl | C≡CCH₂OCF₃ |
| S1-253 | Cl | Cl | C≡CCH₂(C₃H₅) |
| S1-254 | Cl | Cl | C≡CCH₂(C₄H₇) |
| S1-255 | Cl | Cl | C≡C(1-Cl—C₃H₄) |
| S1-256 | Cl | Cl | C≡C(1-F—C₃H₄) |
| S1-257 | Cl | Cl | C≡C(1-Cl—C₄H₆) |
| S1-258 | Cl | Cl | C≡C(1-F—C₄H₆) |
| S1-259 | Cl | Cl | C₃H₅ (cyclopropyl) |
| S1-260 | Cl | Cl | C₄H₇ (cyclobutyl) |
| S1-261 | Cl | Cl | C₅H₉ (cyclopentyl) |
| S1-262 | Cl | Cl | cyclohexyl |
| S1-263 | Cl | Cl | CH(CH₃)—C₃H₅ (CH(CH₃)-cyclopropyl) |
| S1-264 | Cl | Cl | CH₂—C₃H₅ (CH₂-cyclopropyl) |
| S1-265 | Cl | Cl | 1-(Cl)-cyclopropyl |
| S1-266 | Cl | Cl | 1-(F)-cyclopropyl |
| S1-267 | Cl | Cl | 1-(CH₃)-cyclopropyl |
| S1-268 | Cl | Cl | 1-(CN)-cyclopropyl |
| S1-269 | Cl | Cl | 2-(Cl)-cyclopropyl |
| S1-270 | Cl | Cl | 2-(F)-cyclopropyl |
| S1-271 | Cl | Cl | 1-(Cl)-cyclobutyl |
| S1-272 | Cl | Cl | 1-(F)-cyclobutyl |
| S1-273 | Cl | Cl | 2-(Cl)-cyclobutyl |
| S1-274 | Cl | Cl | 3-(Cl)-cyclobutyl |
| S1-275 | Cl | Cl | 2-(F)-cyclobutyl |
| S1-276 | Cl | Cl | 3-(F)-cyclobutyl |
| S1-277 | Cl | Cl | 3,3-Cl₂-cyclobutyl |
| S1-278 | Cl | Cl | 3,3-F₂-cyclobutyl |
| S1-279 | Cl | Cl | 2-(CH₃)-cyclopropyl |
| S1-280 | Cl | Cl | 1-(CH₃)-cyclobutyl |
| S1-281 | Cl | Cl | 2-(CH₃)-cyclobutyl |
| S1-282 | Cl | Cl | 3-(CH₃)-cyclobutyl |
| S1-283 | Cl | Cl | 3,3-(CH₃)₂-cyclobutyl |
| S1-284 | Cl | Cl | 2-(CN)-cyclopropyl |
| S1-285 | Cl | Cl | 1-cyclopropyl-cyclopropyl |
| S1-286 | Cl | Cl | 2-cyclopropyl-cyclopropyl |
| S1-287 | Cl | Cl | CH(CH₃)(cyclobutyl) |
| S1-288 | Cl | Cl | CH₂-(cyclobutyl) |

TABLE S1-continued

| I″ No. | R⁴ | R³ | R¹ |
| --- | --- | --- | --- |
| S1-289 | Cl | Cl | $CH_2CH_2$-(cyclopropyl) |
| S1-290 | Cl | Cl | $CH_2CH_2$-(cyclobutyl) |
| S1-291 | Cl | Cl | $CH_2$-(1-Cl-cyclopropyl) |
| S1-292 | Cl | Cl | $CH_2$-(1-F-cyclopropyl) |
| S1-293 | Cl | Cl | $CH_2$-(1-Cl-cyclobutyl) |
| S1-294 | Cl | Cl | $CH_2$-(1-F-cyclobutyl) |
| S1-295 | Cl | Cl | $CHCH_3$-(1-Cl-cyclopropyl) |
| S1-296 | Cl | Cl | $C(CH_3)_2$-(1-F-cyclopropyl) |
| S1-297 | Cl | Cl | $C_6H_5$ |
| S1-298 | Cl | Cl | 4-Cl—$C_6H_4$ |
| S1-299 | Cl | Cl | 4-$OCH_3$—$C_6H_4$ |
| S1-300 | Cl | Cl | 4-$CH_3$—$C_6H_4$ |
| S1-301 | Cl | Cl | 4-F—$C_6H_4$ |
| S1-302 | Cl | Cl | 2,4-$F_2$—$C_6H_3$ |
| S1-303 | Cl | Cl | 2,4-$Cl_2$—$C_6H_3$ |
| S1-304 | Cl | Cl | 2-$CH_3$—$C_6H_4$ |
| S1-305 | Cl | Cl | 2-$CF_3$—$C_6H_4$ |
| S1-306 | Cl | Cl | 4-$CH_3$—$C_6H_4$ |
| S1-307 | Cl | Cl | 4-$CF_3$—$C_6H_4$ |
| S1-308 | Cl | Cl | 2-$OCH_3$—$C_6H_4$ |
| S1-309 | Cl | Cl | 2-$OCF_3$—$C_6H_4$ |
| S1-310 | Cl | Cl | 4-$OCH_3$—$C_6H_4$ |
| S1-311 | Cl | Cl | 4-$OCF_3$—$C_6H_4$ |
| S1-312 | Cl | Cl | 2,4,6-$F_3$—$C_6H_2$ |
| S1-313 | Cl | Cl | 2,4,6-$Cl_3$—$C_6H_2$ |
| S1-314 | Cl | Cl | $CH_2C_6H_5$ |
| S1-315 | Cl | Cl | $CH_2$—(4-Cl)—$C_6H_4$ |
| S1-316 | Cl | Cl | $CH_2$—(4-$CH_3$)—$C_6H_4$ |
| S1-317 | Cl | Cl | $CH_2$—(4-$OCH_3$)—$C_6H_4$ |
| S1-318 | Cl | Cl | $CH_2$—(4-F)—$C_6H_4$ |
| S1-319 | Cl | Cl | $CH_2$—(2,4-$Cl_2$)—$C_6H_3$ |
| S1-320 | Cl | Cl | $CH_2$—(2,4-$F_2$)—$C_6H_3$ |

According the reaction conditions of the invention, it is possible to reduce the amount of I″ in favor of the desired product I. Consequently, according to the inventive process, it is possible to highly improve the yield of the triazole I compared to common prior art processes.

Furthermore, it has been found that if the reaction product I resulting from step (ii) is crystallized as described according to the invention, the product can be obtained in high yields and purity.

Consequently, according to one preferred embodiment of the invention, the compounds I resulting from step (ii) are crystallized from a suitable solvent such as, for example toluene, an aliphatic alcohol, acetonitrile, ethyl acetate and/or cyclohexane, in particular toluene and/or an aliphatic alcohol.

In particular, the aliphatic alcohol is selected from methanol, ethanol, n-propanol, iso-propanol, n-butanol, isobutanol or any mixture thereof. In particular, the aliphatic alcohol is selected from methanol and ethanol.

Generally, for the crystallizing step, the solvent, in particular dimethylformide as described above, is firstly evaporated in large part, preferably under reduced pressure. Preferably, at least 55% of the solvent, more preferably at least 60% of the solvent, more specifically at least 70% of the solvent are removed. Specifically, it may be preferred, if at least 80%, more specifically at least 90% of the solvent, such as DMF, are removed The solvent can then be recycled to be used again in the process step (ii), if necessary after it has been further rectificated before.

Then, water and the respective suitable solvent such as an ether, for example diethylether, diisopropylether, methyl-tert-butylether (MTBE), methylenechlorid and/or toluene, in particular toluene, are added. Also ethyl acetate can be appropriate as solvent. The product I is then preferably obtained by crystallization directly from the concentrated, e.g. toluene-reaction mixture. Also preferred and suitable according to the invention is the change of solvent to e.g. methanol or ethanol (see above) for the crystallization of the products.

According to one embodiment, seed crystals are added for the crystallization step.

By using the inventive crystallizing step according to the inventive process, in particular when carrying out the process steps (ii) the formation of the undesired symmetric triazole I″ can be reduced to equal or less than 10%, more preferably equal or less than 8%, even more preferably equal or less than 5%, even more preferably equal or less than 2%.

Preferably, the ratio of isolated compound I to I″ is at least 20:1, more preferably at least 30:1, even more preferably 50:1, more specifically 70:1. In particular, the ratio of compound I to I″ is at least 30:1.

Following the inventive process comprising step (i), also common methods of further reacting the oxiranes II to end products I can be carried out.

For example, the epoxide ring of compounds II may be cleaved by reaction with alcohols $R^2OH$ preferably under acidic conditions to result in compounds V:

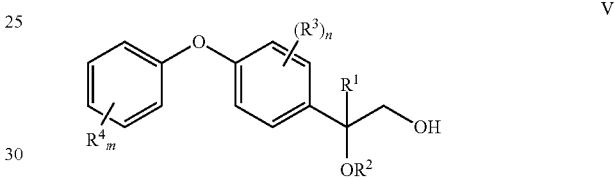

V

Thereafter, the resulting compounds V are reacted with halogenating agents or sulfonating agents such as $PBr_3$, $PCl_3$ mesyl chloride, tosyl chloride or thionyl chloride, to obtain compounds VI wherein LG' is a nucleophilically replaceable leaving group such as halogen, alkylsulfonyl, alkylsulfonyloxy and arylsulfonyloxy, preferably chloro, bromo or iodo, particularly preferably bromo or alkylsulfonyl. Then compounds VI are reacted with 1H-1,2,4-triazole to obtain compounds I as known in the art and/or described above:

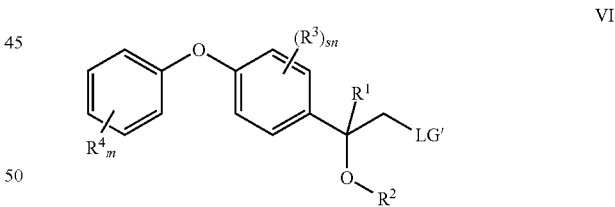

VI

For obtaining compounds of formula I, wherein the alcohol group is derivatized into an ether group to result in compounds of formula I-1,

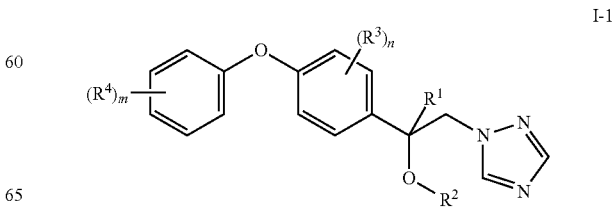

I-1 wherein the variables $R^1$, $R^3$, $R^4$, n and m are defined and preferably defined herein, and wherein
$R^2$ is hydrogen, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkyl-$C_1$-$C_6$-alkyl, phenyl, phenyl-$C_1$-$C_4$-alkyl, phenyl-$C_2$-$C_4$-alkenyl or phenyl-$C_2$-$C_4$-alkynyl;
wherein the aliphatic moieties of $R^2$ are not further substituted or do carry one, two, three or up to the maximum possible number of identical or different groups $R^{12a}$ which independently are selected from:
$R^{12a}$ halogen, OH, CN, nitro, $C_1$-$C_4$-alkoxy, $C_3$-$C_8$-cycloalkyl, $C_3$-$C_8$-halocycloalkyl and $C_1$-$C_4$-halogenalkoxy;
wherein the cycloalkyl and/or phenyl moieties of $R^2$ are not further substituted or do carry one, two, three, four, five or up to the maximum number of identical or different groups $R^{12b}$ which independently are selected from:
$R^{12b}$ halogen, OH, CN, nitro, $C_1$-$C_4$-alkyl, $C_1$-$C_4$-alkoxy, $C_1$-$C_4$-halogenalkyl, $C_3$-$C_8$-cycloalkyl, $C_3$-$C_8$-halocycloalkyl and $C_1$-$C_4$-halogenalkoxy;
the following step can be carried out:
(iii) derivatizing the compound of formula I from step (i) under basic conditions with $R^2$-LG, wherein LG is a nucleophilically replaceable leaving group;
LG represents a nucleophilically replaceable leaving group such as halogen, alkylsulfonyl, alkylsulfonyloxy and arylsulfonyloxy, preferably chloro, bromo or iodo, particularly preferably bromo. Preferably a base is ues in step (iii) such as for example, NaH.

Suitable solvents are for example ethers, in particular cyclic ethers. Possible solvents are for example tetrahydrofuran (THF), 2-methyl-tetrahydrofuran (2-Me-THF), diethyl ether, TBME (tert-butyl methyl ether), CPME (cyclopentyl methyl ether), DME (1,2-dimethoxyethane) and 1,4-di-oxane. Further solvents that may be suitable are, for example, diisopropyl ether, di-n-butyl ether and/or diglyme. Often, the use of THF or 2-methyl-THF is particularly suitable. Furthermore, it may also be suitable to use combinations of two or more different solvents, such as for example any combination of the solvents listed above or any one of the listed ethers with aliphatic hydrocarbons like n-hexane, heptane or aromatic hydrocarbons like toluene or xylenes.

The skilled person is familiar with the reaction in step (iii) and may vary the reaction conditions analogously to known syntheses.

According to a further aspect the invention relates to a process for the preparation of a triazole compound of the formula I

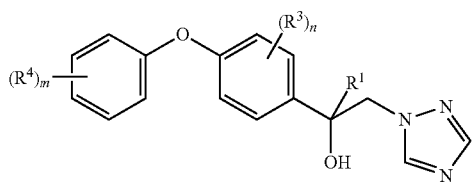

comprising the following step:
(iia) reacting an oxirane of the formula II as defined herein; with 1H-1,2,4-triazole and an inorganic base, wherein less than 1 equivalent of said base is used per 1 equivalent of compound II, resulting in compounds of formula I.
For obtaining compounds of formula I, wherein the alcohol group is derivatized (resulting in "$OR^2$", compounds I-1, see above), the following step can be subsequently carried out:

(iiia) derivatizing the compound of formula I from step (iia) under basic conditions with $R^2$-LG, wherein LG is a nucleophilically replaceable leaving group;
wherein the variables $R^1$, $R^3$, $R^4$, n and m are defined and preferably defined herein.

The reaction steps (ii) and (iii) are described in detail above and also apply accordingly to this aspect of the invention, namely to the corresponding steps (iia) and (iiia), with the proviso, that it is characteristic here that the inorganic base is used in an amount of less than 1 equivalent of per 1 equivalent of compound II.

The oxirane II used in this inventive process can be prepared according to the inventive process described above or may be also provided in analogy to known processes, e.g. by reaction of the respective oxo-group-containing compound III with trimethylsulf(ox)onium halides (($CH_3)_3S^+$ $OHal^-$), preferably trimethylsulfoniumiodide, preferably in the presence of a base such as sodium hydroxide (see also JACS 1965 87 p. 1353).

The starting oxo-group containing compounds III for the inventive processes can be synthesized as described in the above mentioned literature and patent applications. Generally, the skilled person may obtained by various routes in analogy to prior art processes known (cf. J. Agric. Food Chem. (2009) 57, 4854-4860; EP 0 275 955 A1; DE 40 03 180 A1; EP 0 113 640 A2; EP 0 126 430 A2). In the following, synthesis routes for obtaining the precursors are given.

In a first process, for example, phenoles A are reacted, in a first step, with derivatives B, wherein $X^1$ stands for I or Br, in particular Br (=bromo derivatives III), preferably in the presence of a base to result in compounds C.

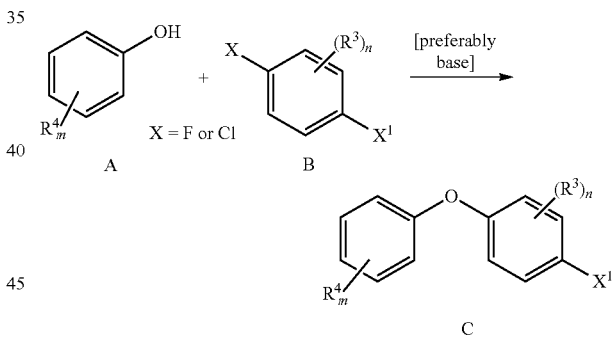

Thereafter, the resulting compounds C, in particular $X^1$ is Br, are then transformed into Grignard reagents by the reaction with transmetallation reagents such as isopropylmagnesium halides and subsequently reacted with acetyl chloride preferably under anhydrous conditions and preferably in the presence of a catalyst such as CuCl, $CuCl_2$, $AlCl_3$, LiCl and mixtures thereof, to obtain acetophenones D.

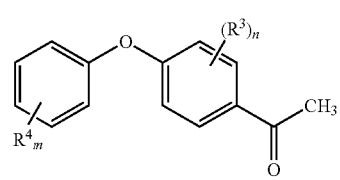

In a second process to obtain the precursors is as follows
In a first step, a halo derivative E, wherein $X^2$ is halogen, in particular F, and $X^3$ is halogen, in particular Br, is reacted with a transmetallation agent such as e.g. isopropylmagnesium bromide followed by an acyl chloride agent $R^1COCl$ (e.g. acetyl chloride) preferably under anhydrous conditions and optionally in the presence of a catalyst such as CuCl, $CuCl_2$, $AlCl_3$, LiCl and mixtures thereof, to obtain ketones F.

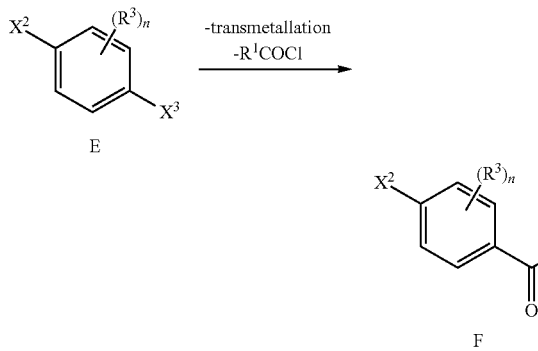

Thereafter, ketones F are reacted with phenoles A preferably in the presence of a base to obtain compounds III wherein $R^1$ is as defined and preferably defined, respectively, herein.

Compounds III may also be obtained in analogy to the first process described for compounds D (preferred conditions for the process step, see above). This is illustrated in the following:

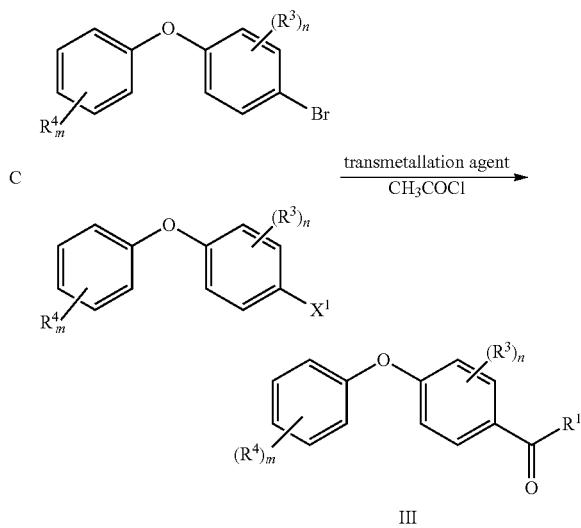

Alternatively, compounds III can be synthesized via a Friedel Crafts acylation as follows:

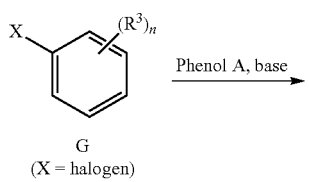

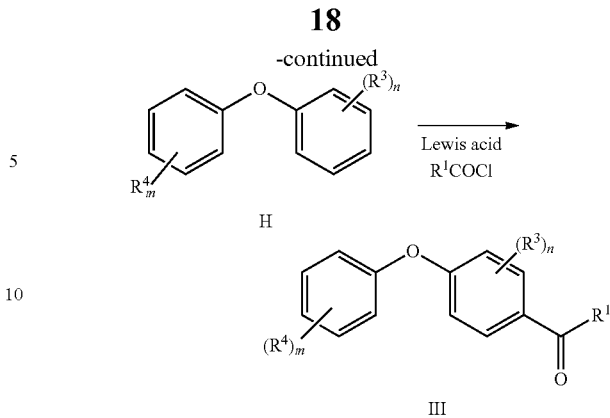

Ethers H can be synthesized by nucleophilic substitution of X group in compound G (Angewandte Chemie, International Edition, 45(35), 5803-5807; 2006, US 20070088015 A1, Journal of the American Chemical Society, 134(17), 7384-7391; 2012). Then, a Lewis acid catalyzed addition of an acid halide, preferably will lead to compounds III (Journal of Chemical Research, Synopses, (8), 245; 1992, WO2010096777 A1).

If individual compounds cannot be directly obtained by the routes described above, they can be prepared by derivatization of other compounds.

In case a work-up of the reaction mixture in any of the reaction steps of the inventive process or the other processes described, is suitable, it can be carried out by procedures known in a general manner to the person skilled in the art. Usually, the reaction mixture is extracted with a suitable organic solvent (for example aromatic hydrocarbons such as toluene and xylenes) and the residue is, if appropriate, purified by recrystallization and/or chromatography.

In the definitions of the variables given herein, collective terms are used which are generally representative for the substituents in question. The term "$C_n$-$C_m$" indicates the number of carbon atoms possible in each case in the substituent or substituent moiety in question.

The term "halogen" refers to fluorine, chlorine, bromine and iodine.

The term "$C_1$-$C_6$-alkyl" refers to a straight-chained or branched saturated hydrocarbon group having 1 to 6 carbon atoms, e.g. methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, 1,1-dimethylpropyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethyl-butyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl. Likewise, the term "$C_2$-$C_4$-alkyl" refers to a straight-chained or branched alkyl group having 2 to 4 carbon atoms, such as ethyl, propyl (n-propyl), 1-methylethyl (iso-propoyl), butyl, 1-methylpropyl (sec.-butyl), 2-methylpropyl (iso-butyl), 1,1-dimethylethyl (tert.-butyl).

The term "$C_1$-$C_6$-haloalkyl" refers to an alkyl group having 1 or 6 carbon atoms as defined above, wherein some or all of the hydrogen atoms in these groups may be replaced by halogen atoms as mentioned above. Examples are "$C_1$-$C_2$-haloalkyl" groups such as chloromethyl, bromomethyl, dichloromethyl, trichloromethyl, fluoromethyl, difluoromethyl, trifluoromethyl, chloro-fluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl.

The term "$C_2$-$C_6$-alkenyl" refers to a straight-chain or branched unsaturated hydrocarbon radical having 2 to 6 carbon atoms and a double bond in any position. Examples are "$C_2$-$C_4$-alkenyl" groups, such as ethenyl, 1-propenyl, 2-propenyl (allyl), 1-methylethenyl, 1-butenyl, 2-butenyl, 3-butenyl, 1-methyl-1-propenyl, 2-methyl-1-propenyl, 1-methyl-2-propenyl, 2-methyl-2-propenyl.

The term "$C_2$-$C_6$-alkynyl" refers to a straight-chain or branched unsaturated hydrocarbon radical having 2 to 6 carbon atoms and containing at least one triple bond. Examples are "$C_2$-$C_4$-alkynyl" groups, such as ethynyl, prop-1-ynyl, prop-2-ynyl (propargyl), but-1-ynyl, but-2-ynyl, but-3-ynyl, 1-methyl-prop-2-ynyl.

The term "$C_3$-$C_8$-cycloalkyl" refers to monocyclic saturated hydrocarbon radicals having 3 to 8 carbon ring members, such as cyclopropyl, cyclobutyl, cyclopentyl, cyclohexyl, cycloheptyl or cyclooctyl.

The term "$C_3$-$C_8$-cycloalkyl-$C_1$-$C_4$-alkyl" refers to alkyl having 1 to 4 carbon atoms (as defined above), wherein one hydrogen atom of the alkyl radical is replaced by a cycloalkyl radical having 3 to 8 carbon atoms (as defined above).

The term "$C_1$-$C_6$-alkoxy" refers to a straight-chain or branched alkyl group having 1 to 6 carbon atoms which is bonded via an oxygen, at any position in the alkyl group. Examples are "$C_1$-$C_4$-alkoxy" groups, such as methoxy, ethoxy, n-propoxy, 1-methylethoxy, butoxy, 1-methylpropoxy, 2-methylpropoxy or 1,1-dimethylethoxy.

The term "$C_1$-$C_6$-haloalkoxy" refers to a $C_1$-$C_6$-alkoxy radical as defined above, wherein some or all of the hydrogen atoms in these groups may be replaced by halogen atoms as mentioned above. Examples are "$C_1$-$C_4$-haloalkoxy" groups, such as $OCH_2F$, $OCHF_2$, $OCF_3$, $OCH_2Cl$, $OCHCl_2$, $OCCl_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloro¬ethoxy, $OC_2F_5$, 2-fluoropropoxy, 3-fluoropropoxy, 2,2-difluoropropoxy, 2,3-difluoro¬propoxy, 2 chloropropoxy, 3-chloropropoxy, 2,3-dichloropropoxy, 2-bromo¬propoxy, 3 bromopropoxy, 3,3,3-trifluoropropoxy, 3,3,3-trichloropropoxy, $OCH_2$—$C_2F_5$, $OCF_2$—$C_2F_5$, 1-fluoromethyl-2-fluoroethoxy, 1-chloromethyl-2-chloroethoxy, 1-bromomethyl-2-bromo¬ethoxy, 4-fluorobutoxy, 4-chlorobutoxy, 4-bromobutoxy or nonafluorobutoxy.

The term "phenyl-$C_1$-$C_6$-alkyl" refers to alkyl having 1 to 6 carbon atoms (as defined above), wherein one hydrogen atom of the alkyl radical is replaced by a phenyl radical. Likewise, the terms "phenyl-$C_2$-$C_6$-alkenyl" and "phenyl-$C_2$-$C_6$-alkynyl" refer to alkenyl and alkynyl, respectively, wherein one hydrogen atom of the aforementioned radicals is replaced by a phenyl radical.

The meanings and preferred meanings described in the following for the variables $R^1$, $R^2$, $R^3$, $R^4$, n and m apply to compounds and the precursors of the compounds I and side products in any of the above detailed inventive processes.

$R^1$ according to the present invention is hydrogen, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkyl-$C_1$-$C_6$-alkyl, phenyl, phenyl-$C_1$-$C_4$-alkyl, phenyl-$C_2$-$C_4$-alkenyl or phenyl-$C_2$-$C_4$-alkynyl, wherein the aliphatic moieties of $R^1$ may carry one, two, three or up to the maximum possible number of identical or different groups $R^{12a}$ which independently of one another are selected from halogen, OH, CN, nitro, $C_1$-$C_4$-alkoxy, $C_3$-$C_8$-cycloalkyl, $C_3$-$C_8$-halocycloalkyl and $C_1$-$C_4$-halogenalkoxy; and wherein the cycloalkyl and/or phenyl moieties of $R^1$ may carry one, two, three, four, five or up to the maximum number of identical or different groups $R^{12b}$, which independently of one another are selected from halogen, OH, CN, nitro, $C_1$-$C_4$-alkyl, $C_1$-$C_4$-alkoxy, $C_1$-$C_4$-halogenalkyl, $C_3$-$C_8$-cycloalkyl, $C_3$-$C_8$-halocycloalkyl and $C_1$-$C_4$-halogenalkoxy.

According to one embodiment, $R^1$ is H.

According to a further embodiment of the invention, $R^1$ is selected from $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkyl-$C_1$-$C_4$-alkyl, phenyl, phenyl-$C_1$-$C_4$-alkyl, phenyl-$C_2$-$C_4$-alkenyl and phenyl-$C_2$-$C_4$-alkynyl, wherein the $R^1$ are in each case unsubstituted or are substituted by $R^{12a}$ and/or $R^{12b}$ as defined and preferably defined herein. Specific embodiments thereof can be found in the below Table P1.

According to one particular embodiment, $R^1$ is $C_1$-$C_6$-alkyl, in particular $C_1$-$C_4$-alkyl, such as $CH_3$, $C_2H_5$, $CH(CH_3)_2$ or $C(CH_3)_3$. A further embodiment relates to compounds, wherein $R^1$ is $C_1$-$C_6$-alkyl, in particular $C_1$-$C_4$-alkyl, that is substituted by one, two or three or up to the maximum possible number of identical or different groups $R^{12a}$, as defined and preferably defined herein. According to a specific embodiment thereof, $R^1$ is $C_1$-$C_6$-haloalkyl, in particular $C_1$-$C_4$-haloalkyl, more particularly $C_1$-$C_2$-haloalkyl such as $CF_3$ or $CHF_2$. According to a further specific embodiment thereof, $R^1$ is $C_1$-$C_4$-alkoxy-$C_1$-$C_6$-alkyl, in particular $C_1$-$C_4$-alkoxy-$C_1$-$C_4$-alkyl, such as $CH_2$—$OCH_3$. Further specific embodiments thereof can be found in the below Table P1.

According to still another embodiment, $R^1$ is $C_3$-$C_8$-cycloalkyl-$C_1$-$C_6$-alkyl, in particular $C_3$-$C_6$-cycloalkyl-$C_1$-$C_4$-alkyl. A further embodiment relates to compounds, wherein $R^1$ is $C_3$-$C_8$-cycloalkyl-$C_1$-$C_6$-alkyl, in particular $C_3$-$C_6$-cycloalkyl-$C_1$-$C_4$-alkyl, that is substituted by one, two or three or up to the maximum possible number of identical or different groups $R^{12a}$ in the alkyl moiety and/or substituted by one, two, three four or five or up to the maximum possible number of identical or different groups $R^{12b}$ in the cycloalkyl moiety. $R^{12a}$ and $R^{12b}$ are in each case as defined and preferably defined herein. Specific embodiments thereof can be found in the below Table P1.

According to another embodiment, $R^1$ is $C_2$-$C_6$-alkenyl, in particular $C_2$-$C_4$-alkenyl, such as $CH=CH_2$, $CH_2CH=CH_2$, $CH=CHCH_3$ or $C(CH_3)=CH_2$. A further embodiment relates to compounds, wherein $R^1$ is $C_2$-$C_6$-alkenyl, in particular $C_2$-$C_4$-alkenyl, that is substituted by one, two or three or up to the maximum possible number of identical or different groups $R^{12a}$ as defined and preferably defined herein. According to a specific embodiment thereof, $R^1$ is $C_2$-$C_6$-haloalkenyl, in particular $C_2$-$C_4$-haloalkenyl. According to a further specific embodiment thereof, $R^1$ is $C_3$-$C_8$-cycloalkyl-$C_2$-$C_6$-alkenyl or $C_3$-$C_8$-halocycloalkyl-$C_2$-$C_6$-alkenyl, in particular $C_3$-$C_6$-cycloalkyl-$C_2$-$C_4$-alkenyl or $C_3$-$C_6$-halocycloalkyl-$C_2$-$C_4$-alkenyl. Further specific embodiments thereof can be found in the below Table P1.

According to still another embodiment, $R^1$ is $C_2$-$C_6$-alkynyl, in particular $C_2$-$C_4$-alkynyl, such as $C≡CH$, $C≡CCH_3$, $CH_2$—$C≡C$—$H$ or $CH_2$—$C≡C$—$CH_3$. A further embodiment relates to compounds, wherein $R^1$ is $C_2$-$C_6$-alkynyl, in particular $C_2$-$C_4$-alkynyl, that is substituted by one, two or three or up to the maximum possible number of identical or different groups $R^{12a}$, as defined and preferably defined herein. According to a specific embodiment thereof, $R^1$ is $C_2$-$C_6$-haloalkynyl, in particular $C_2$-$C_4$-haloalkynyl. According to a further specific embodiment thereof, $R^1$ is $C_3$-$C_8$-cycloalkyl-$C_2$-$C_6$-alkynyl or $C_3$-$C_5$-halocycloalkyl-$C_2$-$C_6$-alkynyl, in particular $C_3$-$C_6$-cycloalkyl-$C_2$-$C_4$-alkynyl or $C_3$-$C_6$-halocycloalkyl-$C_2$-$C_4$-alkynyl. Further specific embodiments thereof can be found in the below Table P1.

According to still another embodiment, $R^1$ is phenyl-$C_1$-$C_4$-alkyl, in particular phenyl-$C_1$-$C_2$-alkyl, such as benzyl, wherein the alkyl moiety in each case is unsubstituted or carries one, two or three $R^{12a}$ as defined and preferably defined herein, in particular selected from halogen, in particular F and Cl, $C_1$-$C_4$-alkoxy, in particular $OCH_3$, and CN, and wherein the phenyl in each case is unsubstituted or carries one, two or three $R^{12b}$ as defined and preferably defined herein, in particular selected from halogen, in particular Cl and F, $C_1$-$C_4$-alkoxy, in particular $OCH_3$, $C_1$-$C_4$-alkyl, in particular $CH_3$ or $C_2H_5$, and CN. Specific embodiments thereof can be found in the below Table P1.

According to still another embodiment, $R^1$ is phenyl-$C_2$-$C_4$-alkenyl, in particular phenyl-$C_2$-$C_3$-alkenyl, such as phenylethenyl, wherein the alkenyl moiety in each case is unsubstituted or carries one, two or three $R^{12a}$ as defined and preferably defined herein, in particular selected from halogen, in particular F and Cl, $C_1$-$C_4$-alkoxy, in particular $OCH_3$, and CN, and wherein the phenyl in each case is unsubstituted or carries one, two or three $R^{12b}$ as defined and preferably defined herein, in particular selected from halogen, in particular Cl and F, $C_1$-$C_4$-alkoxy, in particular $OCH_3$, $C_1$-$C_4$-alkyl, in particular $CH_3$ or $C_2H_5$, and CN. According to still another embodiment, $R^1$ is phenyl-$C_2$-$C_4$-alkynyl, in particular phenyl-$C_2$-$C_3$-alkynyl, such as phenylethinyl, wherein the alkynyl moiety in each case is unsubstituted or carries one, two or three $R^{12a}$, as defined and preferably defined herein, in particular selected from halogen, in particular F and Cl, $C_1$-$C_4$-alkoxy, in particular $OCH_3$, and CN, and wherein the phenyl in each case is unsubstituted or carries one, two or three $R^{12b}$ as defined and preferably defined herein, in particular selected from halogen, in particular Cl and F, $C_1$-$C_4$-alkoxy, in particular $OCH_3$, $C_1$-$C_4$-alkyl, in particular $CH_3$ or $C_2H_5$, and CN. Specific embodiments thereof can be found in the below Table P1.

According to still another embodiment, $R^1$ is $C_3$-$C_8$-cycloalkyl, in particular $C_3$-$C_6$-cycloalkyl, such as $C_3H_5$ (cyclopropyl), $C_4H_7$ (cyclobutyl), cyclopentyl or cyclohexyl. A further embodiment relates to compounds, wherein $R^1$ is $C_3$-$C_8$-cycloalkyl, in particular $C_3$-$C_6$-cycloalkyl, such as $C_3H_5$ (cyclopropyl) or $C_4H_7$ (cyclobutyl), that is substituted by one, two, three four or five or up to the maximum possible number of identical or different groups $R^{12b}$ as defined and preferably defined herein. According to a specific embodiment thereof, $R^1$ is $C_3$-$C_8$-halocycloalkyl, in particular $C_3$-$C_6$-halocycloalkyl, such as halocyclopropyl, in particular 1-F-cyclopropyl or 1-Cl-cyclopropyl. According to a further specific embodiment thereof, $R^1$ is $C_3$-$C_8$-cycloalkyl-$C_3$-$C_8$-cycloalkyl, in particular $C_3$-$C_6$-cycloalkyl-$C_3$-$C_6$-cycloalkyl, wherein each of said cycloalkyl-cycloalkyl moieties is unsubstituted or carries one, two or three $R^{12b}$ as defined and preferably defined herein, such as 1-cyclopropyl-cyclopropyl or 2-cyclopropyl-cyclopropyl. Specific embodiments thereof can be found in the below Table P1.

According to still another embodiment, $R^1$ is phenyl, wherein the phenyl is unsubstituted or carries one, two, three, four or five independently selected $R^{12b}$ as defined and preferably defined herein, in particular selected from halogen, in particular Cl and F, $C_1$-$C_4$-alkoxy, in particular $OCH_3$, $C_1$-$C_4$-alkyl, in particular $CH_3$ or $C_2H_5$, and CN. Specific embodiments thereof can be found in the below Table P1.

In a further embodiment of the invention, $R^1$ is selected from hydrogen, $C_1$-$C_6$-alkyl, $C_2$-$C_6$-alkenyl, $C_2$-$C_6$-alkynyl and $C_3$-$C_6$-cycloalkyl, wherein the $R^1$ are in each case unsubstituted or are substituted by $R^{12a}$ and/or $R^{12b}$ as defined and preferably defined herein. In each case, the substituents may also have the preferred meanings for the respective substituent as defined above. Specific embodiments thereof can be found in the below Table P1.

Particularly preferred embodiments of $R^1$ according to the invention are in Table P1 below, wherein each line of lines P1-1 to P1-160 corresponds to one particular embodiment of the invention, wherein P1-1 to P1-160 are also in any combination a preferred embodiment of the present invention.

TABLE P1

| line | $R^1$ |
|---|---|
| P1-1 | H |
| P1-2 | $CH_3$ |
| P1-3 | $CH_2CH_3$ |
| P1-4 | $CH_2CH_2CH_3$ |
| P1-5 | $CH(CH_3)_2$ |
| P1-6 | $C(CH_3)_3$ |
| P1-7 | $CH(CH_3)CH_2CH_3$ |
| P1-8 | $CH_2CH(CH_3)_2$ |
| P1-9 | $CH_2CH_2CH_2CH_3$ |
| P1-10 | $CF_3$ |
| P1-11 | $CHF_2$ |
| P1-12 | $CH_2F$ |
| P1-13 | $CHCl_2$ |
| P1-14 | $CH_2Cl$ |
| P1-15 | $CH_2OH$ |
| P1-16 | $CH_2CH_2OH$ |
| P1-17 | $CH_2CH_2CH_2OH$ |
| P1-18 | $CH(CH_3)CH_2OH$ |
| P1-19 | $CH_2CH(CH_3)OH$ |
| P1-20 | $CH_2CH_2CH_2CH_2OH$ |
| P1-21 | $CH(CH_3)CN$ |
| P1-22 | $CH_2CH_2CN$ |
| P1-23 | $CH_2CN$ |
| P1-24 | $CH_2CH_2CN$ |
| P1-25 | $CH_2CH_2CH_2CN$, |
| P1-26 | $CH(CH_3)CH_2CN$ |
| P1-27 | $CH_2CH(CH_3)CN$ |
| P1-28 | $CH_2CH_2CH_2CH_2CN$ |
| P1-29 | $CH_2OCH_3$ |
| P1-30 | $CH_2OCH_2CH_3$ |
| P1-31 | $CH(CH_3)OCH_3$ |
| P1-32 | $CH(CH_3)OCH_2CH_3$ |
| P1-33 | $CH_2CH_2OCH_2CH_3$ |
| P1-34 | $CH_2OCF_3$ |
| P1-35 | $CH_2CH_2OCF_3$ |
| P1-36 | $CH_2OCCl_3$ |
| P1-37 | $CH_2CH_2OCCl_3$ |
| P1-38 | $CH=CH_2$ |
| P1-39 | $CH_2CH=CH_2$ |
| P1-40 | $CH_2CH=CHCH_3$ |
| P1-41 | $CH_2C(CH_3)=CH_2$ |
| P1-42 | $CH_2C(CH_3)=CHCH_3$ |
| P1-43 | $CH_2C(CH_3)=C(CH_3)_2$ |
| P1-44 | $CH=CHCH_3$ |
| P1-45 | $C(CH_3)=CH_2$ |
| P1-46 | $CH=C(CH_3)_2$ |
| P1-47 | $C(CH_3)=C(CH_3)_2$ |
| P1-48 | $C(CH_3)=CH(CH_3)$ |
| P1-49 | $C(Cl)=CH_2$ |
| P1-50 | $C(H)=CHCl$ |
| P1-51 | $C(Cl)=CHCl$ |
| P1-52 | $CH=CCl_2$ |
| P1-53 | $C(Cl)=CCl_2$ |

TABLE P1-continued

| line | R$^1$ |
|---|---|
| P1-54 | C(H)=CH(F) |
| P1-55 | C(H)=CF$_2$ |
| P1-56 | C(F)=CF$_2$ |
| P1-57 | C(F)=CHF |
| P1-58 | CH=CHCH$_2$OH |
| P1-59 | CH=CHOCH$_3$ |
| P1-60 | CH=CHCH$_2$OCH$_3$ |
| P1-61 | CH=CHCH$_2$OCF$_3$ |
| P1-62 | CH=CHCH$_2$OCCl$_3$ |
| P1-63 | CH=CH(C$_3$H$_5$) |
| P1-64 | CH=CH(C$_4$H$_7$) |
| P1-65 | CH=CH(1-Cl—C$_3$H$_4$) |
| P1-66 | CH=CH(1-F—C$_3$H$_4$) |
| P1-67 | CH=CH(1-Cl—C$_4$H$_6$) |
| P1-68 | CH=CH(1-F—C$_4$H$_6$) |
| P1-69 | C≡CH |
| P1-70 | C≡CCH$_3$ |
| P1-71 | CH$_2$C≡CCH$_3$ |
| P1-72 | CH$_2$C≡CH |
| P1-73 | CH$_2$C≡CCH$_2$CH$_3$ |
| P1-74 | C≡CCH(CH$_3$)$_2$ |
| P1-75 | C≡CC(CH$_3$)$_3$ |
| P1-76 | C≡C(C$_3$H$_5$) |
| P1-77 | C≡C(C$_4$H$_7$) |
| P1-78 | C≡C(1-Cl—C$_3$H$_4$) |
| P1-79 | C≡C(1-Cl—C$_4$H$_6$) |
| P1-80 | C≡CCl |
| P1-81 | C≡CBr |
| P1-82 | C≡C—I |
| P1-83 | CH$_2$C≡CCl |
| P1-84 | CH$_2$C≡CBr |
| P1-85 | CH$_2$C≡C—I |
| P1-86 | C≡CCH$_2$OCH$_3$ |
| P1-87 | C≡CCH(OH)CH$_3$ |
| P1-88 | C≡CCH(OCH$_3$)CH$_3$ |
| P1-89 | C≡COCH$_3$ |
| P1-90 | CH$_2$C≡COCH$_3$ |
| P1-91 | C≡CCH$_2$OCCl$_3$ |
| P1-92 | C≡CCH$_2$OCF$_3$ |
| P1-93 | C≡CCH$_2$(C$_3$H$_5$) |
| P1-94 | C≡CCH$_2$(C$_4$H$_7$) |
| P1-95 | C≡C(1-Cl—C$_3$H$_4$) |
| P1-96 | C≡C(1-F—C$_3$H$_4$) |
| P1-97 | C≡C(1-Cl—C$_4$H$_6$) |
| P1-98 | C≡C(1-F—C$_4$H$_6$) |
| P1-99 | C$_3$H$_5$ (cyclopropyl) |
| P1-100 | C$_4$H$_7$ (cyclobutyl) |
| P1-101 | C$_5$H$_9$ (cyclopentyl) |
| P1-102 | cyclohexyl |
| P1-103 | CH(CH$_3$)—C$_3$H$_5$ (CH(CH$_3$)-cyclopropyl) |
| P1-104 | CH$_2$—C$_3$H$_5$ (CH$_2$-cyclopropyl) |
| P1-105 | 1-(Cl)-cyclopropyl |
| P1-106 | 1-(F)-cyclopropyl |
| P1-107 | 1-(CH$_3$)-cyclopropyl |
| P1-108 | 1-(CN)-cyclopropyl |
| P1-109 | 2-(Cl)-cyclopropyl |
| P1-110 | 2-(F)-cyclopropyl |
| P1-111 | 1-(Cl)-cyclobutyl |
| P1-112 | 1-(F)-cyclobutyl |
| P1-113 | 2-(Cl)-cyclobutyl |
| P1-114 | 3-(Cl)-cyclobutyl |
| P1-115 | 2-(F)-cyclobutyl |
| P1-116 | 3-(F)-cyclobutyl |
| P1-117 | 3,3-Cl$_2$-cyclobutyl |
| P1-118 | 3,3-F$_2$-cyclobutyl |
| P1-119 | 2-(CH$_3$)-cyclopropyl |
| P1-120 | 1-(CH$_3$)-cyclobutyl |
| P1-121 | 2-(CH$_3$)-cyclobutyl |
| P1-122 | 3-(CH$_3$)-cyclobutyl |
| P1-123 | 3,3-(CH$_3$)$_2$-cyclobutyl |
| P1-124 | 2-(CN)-cyclopropyl |
| P1-125 | 1-cyclopropyl-cyclopropyl |
| P1-126 | 2-cyclopropyl-cyclopropyl |
| P1-127 | CH(CH$_3$)(cyclobutyl) |
| P1-128 | CH$_2$-(cyclobutyl) |
| P1-129 | CH$_2$CH$_2$-(cyclopropyl) |
| P1-130 | CH$_2$CH$_2$-(cyclobutyl) |
| P1-131 | CH$_2$-(1-Cl-cyclopropyl) |
| P1-132 | CH$_2$-(1-F-cyclopropyl) |
| P1-133 | CH$_2$-(1-Cl-cyclobutyl) |
| P1-134 | CH$_2$-(1-F-cyclobutyl) |
| P1-135 | CHCH$_3$-(1-Cl-cyclopropyl) |
| P1-136 | C(CH$_3$)$_2$-(1-F-cyclopropyl) |
| P1-137 | C$_6$H$_5$ |
| P1-138 | 4-Cl—C$_6$H$_4$ |
| P1-139 | 4-OCH$_3$—C$_6$H$_4$ |
| P1-140 | 4-CH$_3$—C$_6$H$_4$ |
| P1-141 | 4-F—C$_6$H$_4$ |
| P1-142 | 2,4-F$_2$—C$_6$H$_3$ |
| P1-143 | 2,4-Cl$_2$—C$_6$H$_3$ |
| P1-144 | 2-CH$_3$—C$_6$H$_4$ |
| P1-145 | 2-CF$_3$—C$_6$H$_4$ |
| P1-146 | 4-CH$_3$—C$_6$H$_4$ |
| P1-147 | 4-CF$_3$—C$_6$H$_4$ |
| P1-148 | 2-OCH$_3$—C$_6$H$_4$ |
| P1-149 | 2-OCF$_3$—C$_6$H$_4$ |
| P1-150 | 4-OCH$_3$—C$_6$H$_4$ |
| P1-151 | 4-OCF$_3$—C$_6$H$_4$ |
| P1-152 | 2,4,6-F$_3$—C$_6$H$_2$ |
| P1-153 | 2,4,6-Cl$_3$—C$_6$H$_2$ |
| P1-154 | CH$_2$C$_6$H$_5$ |
| P1-155 | CH$_2$-(4-Cl)—C$_6$H$_4$ |
| P1-156 | CH$_2$-(4-CH$_3$)—C$_6$H$_4$ |
| P1-157 | CH$_2$-(4-OCH$_3$)—C$_6$H$_4$ |
| P1-158 | CH$_2$-(4-F)—C$_6$H$_4$ |
| P1-159 | CH$_2$-(2,4-Cl$_2$)—C$_6$H$_3$ |
| P1-160 | CH$_2$-(2,4-F$_2$)—C$_6$H$_3$ |

R$^2$ in compounds I-1 prepared according to the present invention or in precursors thereof, is C$_1$-C$_6$-alkyl, C$_2$-C$_6$-alkenyl, C$_2$-C$_6$-alkynyl, C$_3$-C$_8$-cycloalkyl, C$_3$-C$_8$-cycloalkyl-C$_1$-C$_6$-alkyl, phenyl, phenyl-C$_1$-C$_4$-alkyl, phenyl-C$_2$-C$_4$-alkenyl or phenyl-C$_2$-C$_4$-alkynyl, wherein the aliphatic groups of R$^2$ may carry one, two, three or up to the maximum possible number of identical or different groups R$^{12a}$ which independently of one another are selected from halogen, OH, CN, nitro, C$_1$-C$_4$-alkoxy, C$_3$-C$_8$-cycloalkyl, C$_3$-C$_8$-halocycloalkyl and C$_1$-C$_4$-halogenalkoxy; and wherein the cycloalkyl and/or phenyl moieties of R$^2$ may carry one, two, three, four, five or up to the maximum number of identical or different groups R$^{12b}$, which independently of one another are selected from halogen, OH, CN, nitro, C$_1$-C$_4$-alkyl, C$_1$-C$_4$-alkoxy, C$_1$-C$_4$-halogenalkyl, C$_3$-C$_8$-cycloalkyl, C$_3$-C$_8$-halocycloalkyl and C$_1$-C$_4$-halogenalkoxy.

According to a further embodiment of the invention, R$^2$ is selected from C$_1$-C$_6$-alkyl, C$_2$-C$_6$-alkenyl, C$_2$-C$_6$-alkynyl, C$_3$-C$_8$-cycloalkyl, C$_3$-C$_8$-cycloalkyl-C$_1$-C$_4$-alkyl, phenyl, phenyl-C$_1$-C$_4$-alkyl, phenyl-C$_2$-C$_4$-alkenyl and phenyl-C$_2$-C$_4$-alkynyl, wherein the R$^2$ are in each case unsubstituted or are substituted by R$^{12a}$ and/or R$^{12b}$ as defined and preferably defined herein. Specific embodiments thereof can be found in the below Table P2.

According to one particular embodiment, R$^2$ is C$_1$-C$_6$-alkyl, in particular C$_1$-C$_4$-alkyl, such as CH$_3$, C$_2$H$_5$, CH(CH$_3$)$_2$, CH$_2$CH$_2$CH$_3$, CH$_2$CH$_2$CH$_2$CH$_3$, CH$_2$CH(CH$_3$)$_2$. A further embodiment relates to compounds, wherein R$^2$ is C$_1$-C$_6$-alkyl, in particular C$_1$-C$_4$-alkyl, that is substituted by one, two or three or up to the maximum possible number of identical or different groups R$^{12a}$, as defined and preferably defined herein. According to a specific embodiment thereof, R$^2$ is C$_1$-C$_6$-haloalkyl, in particular C$_1$-C$_4$-haloalkyl, more particularly C$_1$-C$_2$-haloalkyl. According to a further specific embodiment, R$^2$ is C$_1$-C$_4$-alkoxy-C$_1$-C$_6$-alkyl, in particular C$_1$-C$_4$-alkoxy-C$_1$-C$_4$-alkyl, such as CH$_2$OCH$_3$ or CH$_2$CH$_2$OCH$_3$. According to still a further specific embodiment thereof, $R^2$ is hydroxy-$C_1$-$C_6$-alkyl, in particular hydroxyl-$C_1$-$C_4$-alkyl, such as $CH_2CH_2OH$. Further specific embodiments thereof can be found in the below Table P2

According to still another embodiment, $R^2$ is $C_3$-$C_8$-cycloalkyl-$C_1$-$C_6$-alkyl, in particular $C_3$-$C_6$-cycloalkyl-$C_1$-$C_4$-alkyl. A further embodiment relates to compounds, wherein $R^2$ is $C_3$-$C_8$-cycloalkyl-$C_1$-$C_6$-alkyl, in particular $C_3$-$C_6$-cycloalkyl-$C_1$-$C_4$-alkyl, more particularly $C_3$-$C_6$-cycloalkyl-$C_1$-$C_2$-alkyl, that is substituted by one, two or three or up to the maximum possible number of identical or different groups $R^{12a}$ in the alkyl moiety and/or substituted by one, two, three four or five or up to the maximum possible number of identical or different groups $R^{12b}$ in the cycloalkyl moiety. $R^{12a}$ and $R^{12b}$ are in each case as defined and preferably defined herein. Specific embodiments thereof can be found in the below Table P2.

According to another embodiment, $R^2$ is $C_2$-$C_6$-alkenyl, in particular $C_2$-$C_4$-alkenyl, such as $CH_2CH=CH_2$, $CH_2C(CH_3)=CH_2$ or $CH_2CH=CHCH_3$. A further embodiment relates to compounds, wherein $R^2$ is $C_2$-$C_6$-alkenyl, in particular $C_2$-$C_4$-alkenyl, that is substituted by one, two or three or up to the maximum possible number of identical or different groups $R^{12a}$ as defined and preferably defined herein. According to a specific embodiment thereof, $R^2$ is $C_2$-$C_6$-haloalkenyl, in particular $C_2$-$C_4$-haloalkenyl, such as $CH_2C(Cl)=CH_2$ and $CH_2C(H)=CHCl$. According to a further specific embodiment thereof, $R^2$ is $C_3$-$C_8$-cycloalkyl-$C_2$-$C_6$-alkenyl or $C_3$-$C_8$-halocycloalkyl-$C_2$-$C_6$-alkenyl, in particular $C_3$-$C_6$-cycloalkyl-$C_2$-$C_4$-alkenyl or $C_3$-$C_6$-halocycloalkyl-$C_2$-$C_4$-alkenyl. Further specific embodiments thereof can be found in the below Table P2.

According to still another embodiment, $R^2$ is $C_2$-$C_6$-alkynyl, in particular $C_2$-$C_4$-alkynyl, such as $CH_2C\equiv CH$ or $CH_2C\equiv CCH_3$. A further embodiment relates to compounds, wherein $R^2$ is $C_2$-$C_6$-alkynyl, in particular $C_2$-$C_4$-alkynyl, that is substituted by one, two or three or up to the maximum possible number of identical or different groups $R^{12a}$, as defined and preferably defined herein. According to a specific embodiment thereof, $R^2$ is $C_2$-$C_6$-haloalkynyl, in particular $C_2$-$C_4$-haloalkynyl. According to a further specific embodiment thereof, $R^2$ is $C_3$-$C_8$-cycloalkyl-$C_2$-$C_6$-alkynyl or $C_3$-$C_8$-halocycloalkyl-$C_2$-$C_6$-alkynyl, in particular $C_3$-$C_6$-cycloalkyl-$C_2$-$C_4$-alkynyl or $C_3$-$C_6$-halocycloalkyl-$C_2$-$C_4$-alkynyl. Specific embodiments thereof can be found in the below Table P2.

According to still another embodiment, $R^2$ is phenyl-$C_1$-$C_4$-alkyl, in particular phenyl-$C_1$-$C_2$-alkyl, such as benzyl, wherein the alkyl moiety in each case is unsubstituted or carries one, two or three $R^{12a}$ as defined and preferably defined herein, in particular selected from halogen, in particular F and Cl, $C_1$-$C_4$-alkoxy, in particular $OCH_3$, and CN, and wherein the phenyl in each case is unsubstituted or carries one, two or three $R^{12b}$ as defined and preferably defined herein, in particular selected from halogen, in particular Cl and F, $C_1$-$C_4$-alkoxy, in particular $OCH_3$, $C_1$-$C_4$-alkyl, in particular $CH_3$ or $C_2H_5$, and CN. Specific embodiments thereof can be found in the below Table P2.

According to still another embodiment, $R^2$ is phenyl-$C_2$-$C_4$-alkenyl, in particular phenyl-$C_2$-$C_3$-alkenyl, such as phenylethenyl, wherein the alkenyl moiety in each case is unsubstituted or carries one, two or three $R^{12a}$ as defined and preferably defined herein, in particular selected from halogen, in particular F and Cl, $C_1$-$C_4$-alkoxy, in particular $OCH_3$, and CN, and wherein the phenyl in each case is unsubstituted or carries one, two or three $R^{12b}$ as defined and preferably defined herein, in particular selected from halogen, in particular Cl and F, $C_1$-$C_4$-alkoxy, in particular $OCH_3$, $C_1$-$C_4$-alkyl, in particular $CH_3$ or $C_2H_5$, and CN.

According to still another embodiment, $R^2$ is phenyl-$C_2$-$C_4$-alkynyl, in particular phenyl-$C_2$-$C_3$-alkynyl, such as phenylethinyl, wherein the alkynyl moiety in each case is unsubstituted or carries one, two or three $R^{12a}$, as defined and preferably defined herein, in particular selected from halogen, in particular F and Cl, $C_1$-$C_4$-alkoxy, in particular $OCH_3$, and CN, and wherein the phenyl in each case is unsubstituted or carries one, two or three $R^{12b}$ as defined and preferably defined herein, in particular selected from halogen, in particular Cl and F, $C_1$-$C_4$-alkoxy, in particular $OCH_3$, $C_1$-$C_4$-alkyl, in particular $CH_3$ or $C_2H_5$, and CN.

According to still another embodiment, $R^2$ is $C_3$-$C_8$-cycloalkyl, in particular $C_3$-$C_6$-cycloalkyl, such as $C_3H_5$ (cyclopropyl), $C_4H_7$ (cyclobutyl), cyclopentyl or cyclohexyl. A further embodiment relates to compounds, wherein $R^2$ is $C_3$-$C_8$-cycloalkyl, in particular $C_3$-$C_6$-cycloalkyl, such as $C_3H_5$ (cyclopropyl) or $C_4H_7$ (cyclobutyl), that is substituted by one, two, three four or five or up to the maximum possible number of identical or different groups $R^{12b}$ as defined and preferably defined herein. According to a specific embodiment thereof, $R^2$ is $C_3$-$C_8$-halocycloalkyl, in particular $C_3$-$C_6$-halocycloalkyl, such as halocyclopropyl, in particular 1-F-cyclopropyl or 1-Cl-cyclopropyl. According to a further specific embodiment thereof, $R^2$ is $C_3$-$C_8$-cycloalkyl-$C_3$-$C_8$-cycloalkyl, in particular $C_3$-$C_6$-cycloalkyl-$C_3$-$C_6$-cycloalkyl, wherein each of said cycloalkyl-cycloalkyl moieties is unsubstituted or carries one, two or three $R^{12b}$ as defined and preferably defined herein.

According to still another embodiment, $R^2$ is phenyl, wherein the phenyl is unsubstituted or carries one, two, three, four or five independently selected $R^{12b}$ as defined and preferably defined herein, in particular selected from halogen, in particular Cl and F, $C_1$-$C_4$-alkoxy, in particular $OCH_3$, $C_1$-$C_4$-alkyl, in particular $CH_3$ or $C_2H_5$, and CN.

In a further embodiment of the invention, $R^2$ is selected from $C_1$-$C_6$-alkyl, $C_2$-$C_6$-alkenyl and $C_2$-$C_6$-alkynyl, wherein the $R^2$ are in each case unsubstituted or are substituted by $R^{12a}$ and/or $R^{12b}$ as defined and preferably defined herein. In each case, the substituents may also have the preferred meanings for the respective substituent as defined above. Specific embodiments thereof can be found in the below Table P2.

$R^{12a}$ are the possible substituents for any aliphatic moiety of $R^1$ and/or $R^2$ and can independently be defined for $R^1$ and $R^2$.

$R^{12a}$ according to the invention is independently selected from halogen, CH, CN, nitro, $C_1$-$C_4$-alkoxy, $C_3$-$C_8$-cycloalkyl, $C_3$-$C_8$-halocycloalkyl and $C_1$-$C_4$-halogenalkoxy.

According to one embodiment $R^{12a}$ is independently selected from halogen, CH, CN, $C_1$-$C_2$-alkoxy, $C_3$-$C_6$-cycloalkyl, $C_3$-$C_6$-halocycloalkyl and $C_1$-$C_2$-halogenalkoxy. Specifically, $R^{12a}$ is independently selected from F, Cl, CH, CN, $C_1$-$C_2$-alkoxy, cyclopropyl, 1-F-cyclopropyl, 1-Cl-cyclopropyl and $C_1$-$C_2$-halogenalkoxy.

$R^{12b}$ are the possible substituents for any cycloalkyl and/or phenyl moiety of $R^1$ and/or $R^2$ and can independently be defined for $R^1$ and $R^2$.

$R^{12b}$ according to the invention is independently selected from halogen, OH, CN, nitro, $C_1$-$C_4$-alkyl, $C_1$-$C_4$-alkoxy, $C_1$-$C_4$-halogenalkyl, $C_3$-$C_8$-cycloalkyl, $C_3$-$C_8$-halocycloalkyl and $C_1$-$C_4$-halogenalkoxy.

According to one embodiment $R^{12b}$ is independently selected from halogen, CN, nitro, $C_1$-$C_2$-alkyl, $C_1$-$C_2$-alkoxy, $C_1$-$C_2$-halogenalkyl, $C_3$-$C_6$-cycloalkyl, $C_3$-$C_6$-halocycloalkyl and $C_1$-$C_2$-halogenalkoxy. Specifically, $R^{12b}$ is independently selected from F, Cl, OH, CN, nitro, $CH_3$, $OCH_3$, cyclopropyl, 1-F-cyclopropyl, 1-Cl-cyclopropyl and halogenmethoxy.

Particularly preferred embodiments of $R^2$ according to the invention are in Table P2 below, wherein each line of lines P2-1 to P2-87 corresponds to one particular embodiment of the invention, wherein P2-1 to P2-87 are also in any combination a preferred embodiment of the present invention.

TABLE P2

| line | $R^2$ |
|---|---|
| P2-1 | $CH_3$ |
| P2-2 | $CH_2CH_3$ |
| P2-3 | $CH(CH_3)_2$ |
| P2-4 | $CH_2CH_2CH_3$ |
| P2-5 | $CH_2CH_2CH_2CH_3$ |
| P2-6 | $CH_2CH(CH_3)_2$ |
| P2-7 | $CF_3$. |
| P2-8 | $CHF_2$ |
| P2-9 | $CFH_2$ |
| P2-10 | $CCl_3$. |
| P2-11 | $CHCl_2$ |
| P2-12 | $CClH_2$ |
| P2-13 | $CH_2CF_3$ |
| P2-14 | $CH_2CHF_2$ |
| P2-15 | $CH_2CCl_3$ |
| P2-16 | $CH_2CHCl_2$ |
| P2-17 | $CH_2CH_2OCH_2CH_3$ |
| P2-18 | $CH(CH_3)OCH_2CH_3$ |
| P2-19 | $CH(CH_3)OCH_3$ |
| P2-20 | $CH_2OCH_3$ |
| P2-21 | $CH_2CH_2OCH_3$ |
| P2-22 | $CH_2OCF_3$ |
| P2-23 | $CH_2CH_2OCF_3$ |
| P2-24 | $CH_2OCCl_3$ |
| P2-25 | $CH_2CH_2OCCl_3$ |
| P2-26 | $CH_2CH_2OH$ |
| P2-27 | $CH_2OH$ |
| P2-28 | $CH_2CH_2CH_2OH$, |
| P2-29 | $CH(CH_3)CH_2OH$ |
| P2-30 | $CH_2CH(CH_3)OH$ |
| P2-31 | $CH_2CH_2CH_2CH_2OH$ |
| P2-32 | $CH_2CN$, |
| P2-33 | $CH_2CH_2CN$, |
| P2-34 | $CH_2CH_2CH_2CN$, |
| P2-35 | $CH(CH_3)CH_2CN$, |
| P2-36 | $CH_2CH(CH_3)CN$, |
| P2-37 | $CH_2CH_2CH_2CH_2CN$ |
| P2-38 | $CH=CH_2$ |
| P2-39 | $C(CH_3)=CH_2$ |
| P2-40 | $CH=CHCH_3$ |
| P2-41 | $CH_2CH=CH_2$ |
| P2-42 | $CH_2CH=CHCH_3$ |
| P2-43 | $CH_2C(CH_3)=CH_2$ |
| P2-44 | $C(CH_3)=CH(CH_3)$ |
| P2-45 | $C(CH_3)=C(CH_3)_2$ |
| P2-46 | $CH=C(CH_3)_2$ |
| P2-47 | $CH=C(Cl)_2$ |
| P2-48 | $C(CH_3)=CH_2$ |
| P2-49 | $CH_2C(Cl)=CH_2$ |
| P2-50 | $CH_2C(H)=CHCl$ |
| P2-51 | $CH=CHCH_2OH$ |
| P2-52 | $CH=C(CH_3)OH$ |
| P2-53 | $CH=CHOCH_3$ |
| P2-54 | $CH=CHCH_2OCH_3$ |
| P2-55 | $CH_2CH=CHCH_2OCH_3$ |
| P2-56 | $CH=CHOCF_3$ |
| P2-57 | $CH=CHCH_2OCF_3$ |
| P2-58 | $CH=CHOCCl_3$ |
| P2-59 | $CH=CHCH_2OCCl_3$ |
| P2-60 | $CH_2CH=CH(C_3H_5)$ |
| P2-61 | $CH_2CH=CH(C_4H_7)$ |
| P2-62 | $CH_2CH=CH(1\text{-}Cl\text{—}C_3H_4)$ |
| P2-63 | $CH_2CH=CH(1\text{-}F\text{—}C_3H_4)$ |
| P2-64 | $C\equiv CH$ |
| P2-65 | $CH_2C\equiv CH$ |
| P2-66 | $CH_2C\equiv CCH_3$ |
| P2-67 | $CH_2C\equiv CCH_2CH_3$ |
| P2-68 | $CH_2C\equiv CCl$ |
| P2-69 | $CH_2C\equiv CF$ |
| P2-70 | $CH_2C\equiv C\text{—}I$ |
| P2-71 | $CH_2C\equiv CCH_2OH$ |
| P2-72 | $C\equiv COCH_3$ |
| P2-73 | $CH_2C\equiv COCH_3$ |
| P2-74 | $CH_2C\equiv CCCH_2OCH_3$ |
| P2-75 | $C\equiv COCF_3$ |
| P2-76 | $CH_2C\equiv COCF_3$ |
| P2-77 | $C\equiv COCCl_3$ |
| P2-78 | $CH_2C\equiv COCCl_3$ |
| P2-79 | $CH_2$-(cyclopropyl) |
| P2-80 | $CH_2$-(cyclobutyl) |
| P2-81 | $CH_2$-(1-Cl-cyclopropyl) |
| P2-82 | $CH_2$-(1-F-cyclopropyl) |
| P2-83 | $CH_2C_6H_5$ |
| P2-84 | $CH_2\text{-}(4\text{-}Cl)\text{—}C_6H_4$ |
| P2-85 | $CH_2\text{-}(4\text{-}F)\text{—}C_6H_4$ |
| P2-86 | $CH_2\text{-}(4\text{-}CH_3)\text{—}C_6H_4$ |
| P2-87 | $CH_2\text{-}(4\text{-}OCH_3)\text{—}C_6H_4$ |

Particularly preferred embodiments of combination of $R^1$ and $R^2$ according to the invention are given in Table A below, wherein each line of lines A-1 to A-56 corresponds to one particular embodiment of the invention, wherein A-1 to A-56 are also in any combination a preferred embodiment for combinations of $R^1$ and $R^2$ of the present invention.

TABLE A

| line | $R^1$ | $R^2$ |
|---|---|---|
| A-1 | H | $CH_3$ |
| A-2 | $CH_3$ | $CH_3$ |
| A-3 | $CH_2CH_3$ | $CH_3$ |
| A-4 | $CH(CH_3)_2$ | $CH_3$ |
| A-5 | $C_3H_5$ (cyclopropyl) | $CH_3$ |
| A-6 | $C_4H_7$ (cyclobutyl) | $CH_3$ |
| A-7 | $C\equiv CCH_3$ | $CH_3$ |
| A-8 | $C(CH_3)_3$ | $CH_3$ |
| A-9 | $CF_3$ | $CH_3$ |
| A-10 | $CHF_2$ | $CH_3$ |
| A-11 | $CH=CHCH_3$ | $CH_3$ |
| A-12 | $C(CH_3)=CH_2$ | $CH_3$ |
| A-13 | 1-(Cl)-cyclopropyl | $CH_3$ |
| A-14 | 1-(F)-cyclopropyl | $CH_3$ |
| A-15 | H | $CH_2CH_3$ |
| A-16 | $CH_3$ | $CH_2CH_3$ |
| A-17 | $CH_2CH_3$ | $CH_2CH_3$ |
| A-18 | $CH(CH_3)_2$ | $CH_2CH_3$ |
| A-19 | $C_3H_5$ (cyclopropyl) | $CH_2CH_3$ |
| A-20 | $C_4H_7$ (cyclobutyl) | $CH_2CH_3$ |
| A-21 | $C\equiv CCH_3$ | $CH_2CH_3$ |
| A-22 | $C(CH_3)_3$ | $CH_2CH_3$ |
| A-23 | $CF_3$ | $CH_2CH_3$ |
| A-24 | $CHF_2$ | $CH_2CH_3$ |
| A-25 | $CH=CHCH_3$ | $CH_2CH_3$ |
| A-26 | $C(CH_3)=CH_2$ | $CH_2CH_3$ |
| A-27 | 1-(Cl)-cyclopropyl | $CH_2CH_3$ |
| A-28 | 1-(F)-cyclopropyl | $CH_2CH_3$ |
| A-29 | H | $CH_2\text{—}CH=CH_2$ |
| A-30 | $CH_3$ | $CH_2\text{—}CH=CH_2$ |
| A-31 | $CH_2CH_3$ | $CH_2\text{—}CH=CH_2$ |
| A-32 | $CH(CH_3)_2$ | $CH_2\text{—}CH=CH_2$ |
| A-33 | $C_3H_5$ (cyclopropyl) | $CH_2\text{—}CH=CH_2$ |
| A-34 | $C_4H_7$ (cyclobutyl) | $CH_2\text{—}CH=CH_2$ |
| A-35 | $C\equiv CCH_3$ | $CH_2\text{—}CH=CH_2$ |
| A-36 | $C(CH_3)_3$ | $CH_2\text{—}CH=CH_2$ |
| A-37 | $CF_3$ | $CH_2\text{—}CH=CH_2$ |
| A-38 | $CHF_2$ | $CH_2\text{—}CH=CH_2$ |
| A-39 | $CH=CHCH_3$ | $CH_2\text{—}CH=CH_2$ |
| A-40 | $C(CH_3)=CH_2$ | $CH_2\text{—}CH=CH_2$ |

TABLE A-continued

| line | $R^1$ | $R^2$ |
| --- | --- | --- |
| A-41 | 1-(Cl)-cyclopropyl | $CH_2$—CH=$CH_2$ |
| A-42 | 1-(F)-cyclopropyl | $CH_2$—CH=$CH_2$ |
| A-43 | H | $CH_2$—C≡C—H |
| A-44 | $CH_3$ | $CH_2$—C≡C—H |
| A-45 | $CH_2CH_3$ | $CH_2$—C≡C—H |
| A-46 | $CH(CH_3)_2$ | $CH_2$—C≡C—H |
| A-47 | $C_3H_5$ (cyclopropyl) | $CH_2$—C≡C—H |
| A-48 | $C_4H_7$ (cyclobutyl) | $CH_2$—C≡C—H |
| A-49 | C≡$CCH_3$ | $CH_2$—C≡C—H |
| A-50 | $C(CH_3)_3$ | $CH_2$—C≡C—H |
| A-51 | $CF_3$ | $CH_2$—C≡C—H |
| A-52 | $CHF_2$ | $CH_2$—C≡C—H |
| A-53 | CH=$CHCH_3$ | $CH_2$—C≡C—H |
| A-54 | $C(CH_3)$=$CH_2$ | $CH_2$—C≡C—H |
| A-55 | 1-(Cl)-cyclopropyl | $CH_2$—C≡C—H |
| A-56 | 1-(F)-cyclopropyl | $CH_2$—C≡C—H |

According to the invention, there can be zero, one, two, three or four $R^3$ present, namely for n is 0, 1, 2, 3 or 4.

According to one embodiment, n is 0.

According to a further embodiment, n is 1. According to still a further embodiment, n is 1 or 2.

According to still a further embodiment, n is 2 or 3. According to one specific embodiment thereof, n is 2, according to a further specific embodiment, n is 3.

According to one embodiment of the invention, one $R^3$ is attached to the 2-position ($R^{31}$).

According to one specific embodiment thereof, n is 1, according to a further specific embodiment, n is 2.

According to one embodiment of the invention, one $R^3$ is attached to the 3-position ($R^{32}$).

According to one specific embodiment thereof, n is 1, according to a further specific embodiment, n is 2.

According to a further embodiment of the invention, one $R^3$ is attached to the 5-position ($R^{34}$).

According to one specific embodiment thereof, n is 1, according to a further specific embodiment, n is 2.

According to still a further embodiment, n is 1, 2 or 3 and one $R^3$ is in 2- or 6-position.

According to a further embodiment of the invention, two $R^3$ are attached in 2,3-position.

According to one specific embodiment thereof, n is 2, according to a further specific embodiment, n is 3.

According to a further embodiment of the invention, two $R^3$ are attached in 2,5-position.

According to one specific embodiment thereof, n is 2, according to a further specific embodiment, n is 3.

According to a further embodiment of the invention, two $R^3$ are attached in 2,6-position.

According to one specific embodiment thereof, n is 2, according to a further specific embodiment, n is 3.

According to a further embodiment of the invention, two $R^3$ are attached in 3,5-position.

According to one specific embodiment thereof, n is 2, according to a further specific embodiment, n is 3.

For every $R^3$ (or $R^{31}$, $R^{32}$, $R^{34}$, $R^{35}$, respectively) that is present in the inventive compounds, the following embodiments and preferences apply independently of the meaning of any other $R^3$ (or $R^{31}$, $R^{32}$, $R^{33}$, $R^{34}$, $R^{35}$, respectively) that may be present in the phenyl ring. Furthermore, the particular embodiments and preferences given herein for $R^3$ (or $R^{31}$, $R^{32}$, $R^{33}$, $R^{34}$, $R^{35}$, respectively) apply independently for each of n=1, n=2, n=3 and n=4.

According to the invention, each $R^3$ is independently selected from halogen, CN, $NO_2$, OH, SH, $C_1$-$C_6$-alkyl, $C_1$-$C_6$-alkoxy, $C_2$-$C_6$-alkenyl, $C_2$-$C_6$-alkynyl, $C_3$-$C_8$-cycloalkyl, $C_3$-$C_8$-cycloalkyloxy, $NH_2$, $NH(C_1$-$C_4$-alkyl), $N(C_1$-$C_4$-alkyl)$_2$, $NH(C_3$-$C_6$-cycloalkyl), $N(C_3$-$C_6$-cycloalkyl)$_2$, $S(O)_p(C_1$-$C_4$-alkyl), $C(=O)(C_1$-$C_4$-alkyl), $C(=O)(OH)$, $C(=O)(O$—$C_1$-$C_4$-alkyl), $C(=O)(NH(C_1$-$C_4$-alkyl))$, $C(=O)(N(C_1$-$C_4$-alkyl)$_2)$, $C(=O)(NH(C_3$-$C_6$-cycloalkyl))$ and $C(=O)$—$(N(C_3$-$C_6$-cycloalkyl)$_2)$; wherein each of $R^3$ is unsubstituted or further substituted by one, two, three or four $R^{3a}$; wherein $R^{3a}$ is independently selected from halogen, CN, $NO_2$, OH, $C_1$-$C_4$-alkyl, $C_1$-$C_4$-haloalkyl, $C_3$-$C_8$-cycloalkyl, $C_3$-$C_8$-halocycloalkyl, $C_1$-$C_4$-alkoxy and $C_1$-$C_4$-haloalkoxy.

According to one embodiment, $R^3$ is independently selected from halogen, CN, $NO_2$, $C_1$-$C_4$-alkyl, $C_1$-$C_4$-haloalkyl, $C_1$-$C_4$-alkoxy, $C_1$-$C_4$-haloalkoxy, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl, $S(C_1$-$C_2$-alkyl), $S(O)(C_1$-$C_2$-alkyl), $S(O)_2(C_1$-$C_2$-alkyl), $C(=O)(C_1$-$C_2$-alkyl), $C(=O)(OH)$ and $C(=O)(O$—$C_1$-$C_2$-alkyl).

According to a further embodiment, $R^3$ is independently selected from halogen, CN, $NO_2$, OH, SH, $C_1$-$C_6$-alkyl, $C_1$-$C_6$-alkoxy, $C_2$-$C_6$-alkenyl, $C_2$-$C_6$-alkynyl, $C_3$-$C_8$-cycloalkyl, $C_3$-$C_8$-cycloalkyloxy, $NH_2$, $NH(C_1$-$C_4$-alkyl), $N(C_1$-$C_4$-alkyl)$_2$, $NH(C_3$-$C_6$-cycloalkyl), $N(C_3$-$C_6$-cycloalkyl)$_2$, $S(O)_p(C_1$-$C_4$-alkyl) (p=0, 1 or 2), $C(=O)(C_1$-$C_4$-alkyl), $C(=O)(OH)$, $C(=O)(O$—$C_1$-$C_4$-alkyl), $C(=O)(NH(C_1$-$C_4$-alkyl))$, $C(=O)(N(C_1$-$C_4$-alkyl)$_2)$, $C(=O)(NH(C_3$-$C_6$-cycloalkyl))$ and $C(=O)$—$(N(C_3$-$C_6$-cycloalkyl)$_2)$; wherein each of $R^3$ is unsubstituted or further substituted by one, two, three or four $R^{3a}$, wherein $R^{3a}$ is as defined and preferably defined herein.

According to still a further embodiment, $R^3$ is independently selected from halogen, CN, $NO_2$, $C_1$-$C_4$-alkyl, $C_1$-$C_4$-haloalkyl, $C_1$-$C_4$-alkoxy, $C_1$-$C_4$-haloalkoxy, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl, $S(C_1$-$C_2$-alkyl), $S(O)(C_1$-$C_2$-alkyl), $S(O)_2(C_1$-$C_2$-alkyl), $C(=O)(C_1$-$C_2$-alkyl), $C(=O)(OH)$ and $C(=O)(O$—$C_1$-$C_2$-alkyl).

According to still a further embodiment, $R^3$ is independently selected from F, Cl, Br, CN, $C_1$-$C_4$-alkyl, $C_1$-$C_4$-haloalkyl, $C_1$-$C_4$-alkoxy, $C_1$-$C_4$-haloalkoxy, $S(C_1$-$C_4$-alkyl), $S(O)(C_1$-$C_4$-alkyl) and $S(O)_2(C_1$-$C_4$-alkyl).

According to one specific embodiment, $R^3$ is halogen, in particular Br, F or Cl, more specifically F or Cl.

According to a further specific embodiment, $R^3$ is CN.

According to a further specific embodiment, $R^3$ is $C_1$-$C_6$-alkyl, in particular $C_1$-$C_4$-alkyl, such as $CH_3$.

According to a further specific embodiment, $R^3$ is $C_1$-$C_6$-haloalkyl, in particular $C_1$-$C_4$-haloalkyl, such as $CF_3$, $CHF_2$, $CH_2F$, $CCl_3$, $CHCl_2$ or $CH_2Cl$.

According to a further specific embodiment, $R^3$ is $C_1$-$C_6$-alkoxy, in particular $C_1$-$C_4$-alkoxy, more specifically $C_1$-$C_2$-alkoxy such as $OCH_3$ or $OCH_2CH_3$.

According to a further specific embodiment, $R^3$ is $C_1$-$C_6$-haloalkoxy, in particular $C_1$-$C_4$-haloalkoxy, more specifically $C_1$-$C_2$-haloalkoxy such as $OCF_3$, $OCHF_2$, $OCH_2F$, $OCCl_3$, $OCHCl_2$ or $OCH_2Cl$, in particular $OCF_3$, $OCHF_2$, $OCCl_3$ or $OCHCl_2$.

According to still a further embodiment, $R^3$ is $C_2$-$C_6$-alkenyl or $C_2$-$C_6$-haloalkenyl, in particular $C_2$-$C_4$-alkenyl or $C_2$-$C_4$-haloalkenyl, such as CH=$CH_2$.

According to still a further embodiment, $R^3$ is $C_2$-$C_6$-alkynyl or $C_2$-$C_6$-haloalkynyl, in particular $C_2$-$C_4$-alkynyl or $C_2$-$C_4$-haloalkynyl, such as C≡CH.

According to still a further embodiment, $R^3$ is selected from $C(=O)(C_1$-$C_4$-alkyl), $C(=O)(OH)$, $C(=O)(O$—$C_1$-$C_4$-alkyl), $C(=O)(NH(C_1$-$C_4$-alkyl))$, $C(=O)(N(C_1$-$C_4$- alkyl)$_2$), C(=O)(NH(C$_3$-C$_6$-cycloalkyl)) and C(=O)(N(C$_3$-C$_6$-cycloalkyl)$_2$), in particular selected from C(=O)(C$_1$-C$_2$-alkyl), C(=O)(OH), C(=O)(O—C$_1$-C$_2$-alkyl), C(=O)(NH(C$_1$-C$_2$-alkyl)), C(=O)(N(C$_1$-C$_2$-alkyl)$_2$), C(=O)(NH(C$_3$-C$_6$-cycloalkyl)) and C(=O)(N(C$_3$-C$_6$-cycloalkyl)$_2$)). According to one specific embodiment thereof, R$^3$ is C(=O)(OH) or C(=O)(O—C$_1$-C$_4$-alkyl), in particular C(=O)(OCH$_3$).

According to still a further embodiment, R$^3$ is selected from S(C$_1$-C$_2$-alkyl), S(O)(C$_1$-C$_2$-alkyl) and S(O)$_2$(C$_1$-C$_2$-alkyl), in particular SCH$_3$, S(O)(CH$_3$) and S(O)$_2$(CH$_3$).

R$^{3a}$ is independently selected from halogen, CN, NO$_2$, OH, C$_1$-C$_4$-alkyl, C$_1$-C$_4$-haloalkyl, C$_3$-C$_8$-cycloalkyl, C$_3$-C$_8$-halocycloalkyl, C$_1$-C$_4$-alkoxy and C$_1$-C$_4$-halogenalkoxy, in particular selected from halogen, CN, C$_1$-C$_2$-alkyl, C$_1$-C$_2$-haloalkyl, C$_3$-C$_6$-cycloalkyl, C$_3$-C$_6$-halocycloalkyl, C$_1$-C$_2$-alkoxy and C$_1$-C$_2$-halogenalkoxy. Specifically, R$^{3a}$ is independently selected from F, Cl, CN, OH, CH$_3$, halomethyl, cyclopropyl, halocyclopropyl, OCH$_3$ and halogenmethoxy.

Particularly preferred embodiments of R$^3$ according to the invention are in Table P3 below, wherein each line of lines P3-1 to P3-16 corresponds to one particular embodiment of the invention, wherein P3-1 to P3-16 are also in any combination with one another a preferred embodiment of the present invention. Thereby, for every R$^3$ that is present in the inventive compounds, these specific embodiments and preferences apply independently of the meaning of any other R$^3$ that may be present in the phenyl ring:

TABLE P3

| No. | R$^3$ |
| --- | --- |
| P3-1 | Cl |
| P3-2 | F |
| P3-3 | CN |
| P3-4 | NO$_2$ |
| P3-5 | CH$_3$ |
| P3-6 | CH$_2$CH$_3$ |
| P3-7 | CF$_3$ |
| P3-8 | CHF$_2$ |
| P3-9 | OCH$_3$ |
| P3-10 | OCH$_2$CH$_3$ |
| P3-11 | OCF$_3$ |
| P3-12 | OCHF$_2$ |
| P3-13 | SCH$_3$ |
| P3-14 | SOCH$_3$ |
| P3-15 | SO$_2$CH$_3$ |
| P3-16 | CO$_2$CH$_3$ |

Particularly preferred embodiments of (R$^3$)$_n$, according to the invention are in Table P33 below, wherein each line of lines P33-1 to P33-60 corresponds to one particular embodiment of the invention, wherein P33-1 to P33-60 are also in any combination a preferred embodiment of the present invention.

TABLE P33

| No. | (R$^3$)$_n$ |
| --- | --- |
| P33-1 | —* |
| P33-2 | 2-Cl |
| P33-3 | 3-Cl |
| P33-4 | 2-F |
| P33-5 | 3-F |
| P33-6 | 2-CN |
| P33-7 | 3-CN |
| P33-8 | 2-NO$_2$ |
| P33-9 | 3-NO$_2$ |
| P33-10 | 2-SCH$_3$ |
| P33-11 | 3-SCH$_3$ |
| P33-12 | 2-SOCH$_3$ |
| P33-13 | 3-SOCH$_3$ |
| P33-14 | 2-SO$_2$CH$_3$ |
| P33-15 | 3-SO$_2$CH$_3$ |
| P33-16 | 2-CO$_2$CH$_3$ |
| P33-17 | 3-CO$_2$CH$_3$ |
| P33-18 | 2,3-Cl$_2$ |
| P33-19 | 2,5-Cl$_2$ |
| P33-20 | 3,5-Cl$_2$ |
| P33-21 | 2,6-Cl$_2$ |
| P33-22 | 2,3-F$_2$ |
| P33-23 | 2,5-F$_2$ |
| P33-24 | 3,5-F$_2$ |
| P33-25 | 2,6-F$_2$ |
| P33-26 | 2-F-3-Cl |
| P33-27 | 2-F-6-Cl |
| P33-28 | 2-Cl-3-F |
| P33-29 | 2-CH$_3$ |
| P33-30 | 3-CH$_3$ |
| P33-31 | 2-CH$_2$CH$_3$ |
| P33-32 | 3-CH$_2$CH$_3$ |
| P33-33 | 2-CF$_3$ |
| P33-34 | 3-CF$_3$ |
| P33-35 | 2-CHF$_2$ |
| P33-36 | 3-CHF$_2$ |
| P33-37 | 2-OCH$_3$ |
| P33-38 | 3-OCH$_3$ |
| P33-39 | 2-OCH$_2$CH$_3$ |
| P33-40 | 3-OCH$_2$CH$_3$ |
| P33-41 | 2-OCF$_3$ |
| P33-42 | 3-OCF$_3$ |
| P33-43 | 2-OCHF$_2$ |
| P33-44 | 3-OCHF$_2$ |
| P33-45 | 2,3-(CH$_3$)$_2$ |
| P33-46 | 2,6-(CH$_3$)$_2$ |
| P33-47 | 2,3-(CH$_2$CH$_3$)$_2$ |
| P33-48 | 2,6-(CH$_2$CH$_3$)$_2$ |
| P33-49 | 2,3-(CF$_3$)$_2$ |
| P33-50 | 2,6-(CF$_3$)$_2$ |
| P33-51 | 2,3-(CHF$_2$)$_2$ |
| P33-52 | 2,6-(CHF$_2$)$_2$ |
| P33-53 | 2,3-(OCH$_3$)$_2$ |
| P33-54 | 2,6-(OCH$_3$)$_2$ |
| P33-55 | 2,3-(OCH$_2$CH$_3$)$_2$ |
| P33-56 | 2,6-(OCH$_2$CH$_3$)$_2$ |
| P33-57 | 2,3-(OCF$_3$)$_2$ |
| P33-58 | 2,6-(OCF$_3$)$_2$ |
| P33-59 | 2,3-(OCHF$_2$)$_2$ |
| P33-60 | 2,6-(OCHF$_2$)$_2$ |

Each R$^4$ according to the present invention is independently selected from halogen, CN, NO$_2$, OH, SH, C$_1$-C$_6$-alkyl, C$_1$-C$_6$-alkoxy, C$_2$-C$_6$-alkenyl, C$_2$-C$_6$-alkynyl, C$_3$-C$_8$-cycloalkyl, C$_3$-C$_8$-cycloalkyloxy, NH$_2$, NH(C$_1$-C$_4$-alkyl), N(C$_1$-C$_4$-alkyl)$_2$, NH(C$_3$-C$_6$-cycloalkyl), N(C$_3$-C$_6$-cycloalkyl)$_2$, S(O)$_p$(C$_1$-C$_4$-alkyl), C(=O)(C$_1$-C$_4$-alkyl), C(=O)(OH), C(=O)(O—C$_1$-C$_4$-alkyl), C(=O)(NH(C$_1$-C$_4$-alkyl)), C(=O)(N(C$_1$-C$_4$-alkyl)$_2$), C(=O)(NH(C$_3$-C$_6$-cycloalkyl)) and C(=O)—(N(C$_3$-C$_6$-cycloalkyl)$_2$); wherein each of R$^4$ is unsubstituted or further substituted by one, two, three or four R$^{4a}$ independently selected from halogen, CN, NO$_2$, OH, C$_1$-C$_4$-alkyl, C$_1$-C$_4$-haloalkyl, C$_3$-C$_8$-cycloalkyl, C$_3$-C$_8$-halocycloalkyl, C$_1$-C$_4$-alkoxy and C$_1$-C$_4$-haloalkoxy.

According to the invention, there can be zero, one, two, three, four or five R$^4$ present, namely for m is 0, 1, 2, 3, 4 or 5. In particular, m is 0, 1, 2, 3 or 4.

According to one embodiment, m is 0.

According to a further embodiment, m is 1, 2, 3 or 4, in particular 1, 2 or 3, more specifically 1 or 2. According to one specific embodiment thereof, m is 1, according to a further specific embodiment, m is 2.

According to still a further embodiment, m is 2, 3 or 4.

According to still a further embodiment, m is 3.

According to one embodiment of the invention, one $R^4$ is attached to the para-position (4-position).

According to a further embodiment of the invention, one $R^4$ is attached to the meta-position (3-position).

According to a further embodiment of the invention, one $R^4$ is attached to the ortho-position (2-position).

According to a further embodiment of the invention, two $R^4$ are attached in 2,4-position.

According to a further embodiment of the invention, two $R^4$ are attached in 2,3-position.

According to a further embodiment of the invention, two $R^4$ are attached in 2,5-position.

According to a further embodiment of the invention, two $R^4$ are attached in 2,6-position.

According to a further embodiment of the invention, two $R^4$ are attached in 3,4-position.

According to a further embodiment of the invention, two $R^4$ are attached in 3,5-position.

According to a further embodiment of the invention, three $R^4$ are attached in 2,4,6-position.

For every $R^4$ that is present in the inventive compounds, the following embodiments and preferences apply independently of the meaning of any other $R^4$ that may be present in the phenyl ring. Furthermore, the particular embodiments and preferences given herein for $R^4$ apply independently for each of m=1, m=2, m=3, m=4 and m=5.

According to one embodiment, $R^4$ is independently selected from halogen, CN, $NO_2$, OH, SH, $C_1$-$C_6$-alkyl, $C_1$-$C_6$-alkoxy, $C_2$-$C_6$-alkenyl, $C_2$-$C_6$-alkynyl, $C_3$-$C_8$-cycloalkyl, $C_3$-$C_8$-cycloalkyloxy, $NH_2$, $NH(C_1$-$C_4$-alkyl), $N(C_1$-$C_4$-alkyl)$_2$, $NH(C_3$-$C_6$-cycloalkyl), $N(C_3$-$C_6$-cycloalkyl)$_2$, $S(O)_p(C_1$-$C_4$-alkyl) (p=0, 1 or 2), $C(=O)(C_1$-$C_4$-alkyl), $C(=O)(OH)$, $C(=O)(O$—$C_1$-$C_4$-alkyl), $C(=O)(NH(C_1$-$C_4$-alkyl))$, $C(=O)(N(C_1$-$C_4$-alkyl)$_2$), $C(=O)(NH(C_3$-$C_6$-cycloalkyl))$ and $C(=O)$—$(N(C_3$-$C_6$-cycloalkyl)$_2$); wherein each of $R^4$ is unsubstituted or further substituted by one, two, three or four independently selected $R^{4a}$, wherein $R^{4a}$ is as defined and preferably defined herein.

According to a further embodiment, $R^4$ is independently selected from halogen, CN, $NO_2$, $C_1$-$C_4$-alkyl, $C_1$-$C_4$-alkoxy, $C_2$-$C_4$-alkenyl, $C_2$-$C_4$-alkynyl, $C_3$-$C_6$-cycloalkyl, $C_3$-$C_6$-cycloalkyloxy, $NH_2$, $NH(C_1$-$C_{42}$-alkyl), $N(C_1$-$C_2$-alkyl)$_2$, $S(O)_p(C_1$-$C_2$-alkyl) (p=0, 1 or 2), $C(=O)(C_1$-$C_2$-alkyl), $C(=O)(OH)$ and $C(=O)(O$—$C_1$-$C_2$-alkyl), wherein each of $R^4$ is unsubstituted or further substituted by one, two, three or four independently selected $R^{4a}$, wherein $R^{4a}$ is as defined and preferably defined herein.

According to a further embodiment, $R^4$ is independently selected from halogen, CN, $NO_2$, $C_1$-$C_4$-alkyl, $C_1$-$C_4$-haloalkyl, $C_1$-$C_4$-alkoxy, $C_1$-$C_4$-haloalkoxy, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl, $S(C_1$-$C_2$-alkyl), $S(O)(C_1$-$C_2$-alkyl), $S(O)_2(C_1$-$C_2$-alkyl), $C(=O)(C_1$-$C_2$-alkyl), $C(=O)(OH)$ and $C(=O)(O$—$C_1$-$C_2$-alkyl).

According to a further embodiment, $R^4$ is independently selected from halogen, CN, $NO_2$, $C_1$-$C_2$-alkyl, $C_1$-$C_2$-haloalkyl, $C_1$-$C_2$-alkoxy, $C_1$-$C_2$-haloalkoxy, $S(C_1$-$C_2$-alkyl), $S(O)(C_1$-$C_2$-alkyl), $S(O)_2(C_1$-$C_2$-alkyl), $C(=O)(OH)$ and $C(=O)(O$—$C_1$-$C_2$-alkyl).

According to a further embodiment, $R^4$ is independently selected from F, Cl, Br, CN, $C_1$-$C_4$-alkyl, $C_1$-$C_4$-haloalkyl, $C_1$-$C_4$-alkoxy, $C_1$-$C_4$-haloalkoxy, $S(C_1$-$C_4$-alkyl), $S(O)(C_1$-$C_4$-alkyl) and $S(O)_2(C_1$-$C_4$-alkyl).

According to still a further specific embodiment, $R^4$ is independently selected from halogen, in particular from Br, F and Cl, more specifically from F and Cl.

According to a further specific embodiment, $R^4$ is CN.

According to one further embodiment $R^4$ is $NO_2$.

According to one further embodiment $R^4$ is OH.

According to one further embodiment $R^4$ is SH.

According to a further specific embodiment, $R^4$ is $C_1$-$C_6$-alkyl, in particular $C_1$-$C_4$-alkyl, such as $CH_3$. Further appropriate alkyls are ethyl, n-propyl, i-propyl, n-butyl, i-butyl and t-butyl.

According to a further specific embodiment, $R^4$ is $C_1$-$C_6$-haloalkyl, in particular $C_1$-$C_4$-haloalkyl, such as $CF_3$, $CHF_2$, $CH_2F$, $CCl_3$, $CHCl_2$ or $CH_2Cl$.

According to a further specific embodiment $R^4$ is $C_1$-$C_6$-alkyl, preferably $C_1$-$C_4$-alkyl, substituted by OH, more preferably $CH_2OH$, $CH_2CH_2OH$, $CH_2CH_2CH_2OH$, $CH(CH_3)CH_2OH$, $CH_2CH(CH_3)OH$, $CH_2CH_2CH_2CH_2OH$. In a special embodiment $R^4$ is $CH_2OH$. According to a further specific embodiment $R^4$ is $C_1$-$C_6$-alkyl, preferably $C_1$-$C_4$-alkyl substituted by CN, more preferably $CH_2CN$, $CH_2CH_2CN$, $CH_2CH_2CH_2CN$, $CH(CH_3)CH_2CN$, $CH_2CH(CH_3)CN$, $CH_2CH$—$_2CH_2CH_2CN$. In a special embodiment $R^4$ is $CH_2CH_2CN$. In a further special embodiment $R^4$ is $CH(CH_3)CN$. According to a further specific embodiment $R^4$ is $C_1$-$C_4$-alkoxy-$C_1$-$C_6$-alkyl, more preferably $C_1$-$C_4$-alkoxy-$C_1$-$C_4$-alkyl. In a special embodiment $R^4$ is $CH_2OCH_3$. In a further special embodiment $R^4$ is $CH_2CH_2OCH_3$. In a further special embodiment $R^4$ is $CH(CH_3)OCH_3$. In a further special embodiment $R^4$ is $CH(CH_3)OCH_2CH_3$. In a further special embodiment $R^4$ is $CH_2CH_2OCH_2CH_3$. According to a further specific embodiment $R^4$ is $C_1$-$C_4$-haloalkoxy-$C_1$-$C_6$-alkyl, more preferably $C_1$-$C_4$-alkoxy-$C_1$-$C_4$-alkyl. In a special embodiment $R^4$ is $CH_2OCF_3$. In a further special embodiment $R^4$ is $CH_2CH_2OCF_3$. In a further special embodiment $R^4$ is $CH_2OCCl_3$. In a further special embodiment $R^4$ is $CH_2CH_2OCCl_3$.

According to a further specific embodiment, $R^4$ is $C_1$-$C_6$-alkoxy, in particular $C_1$-$C_4$-alkoxy, more specifically $C_1$-$C_2$-alkoxy such as $OCH_3$ or $OCH_2CH_3$.

According to a further specific embodiment, $R^4$ is $C_1$-$C_6$-haloalkoxy, in particular $C_1$-$C_4$-haloalkoxy, more specifically $C_1$-$C_2$-haloalkoxy such as $OCF_3$, $OCHF_2$, $OCH_2F$, $OCCl_3$, $OCHCl_2$ or $OCH_2Cl$, in particular $OCF_3$, $OCHF_2$, $OCCl_3$ or $OCHCl_2$.

According to still a further embodiment, $R^4$ is $C_2$-$C_6$-alkenyl or $C_2$-$C_6$-haloalkenyl, in particular $C_2$-$C_4$-alkenyl or $C_2$-$C_4$-haloalkenyl, such as $CH=CH_2$, $CH_2CH=CH_2$, $CH=CHCH_3$ or $C(CH_3)=CH_2$.

According to a further specific embodiment $R^4$ is $C_2$-$C_6$-alkenyl, preferably $C_2$-$C_4$-alkenyl, substituted by OH, more preferably, $CH=CHOH$, $CH=CHCH_2OH$, $C(CH_3)=CHOH$, $CH=C(CH_3)OH$. In a special embodiment $R^4$ is $CH=CHOH$. In a further special embodiment $R^4$ is $CH=CHCH_2OH$.

According to a further specific embodiment $R^4$ is $C_1$-$C_4$-alkoxy-$C_2$-$C_6$-alkenyl, more preferably $C_1$-$C_4$-alkoxy-$C_2$-$C_4$-alkenyl. In a special embodiment $R^4$ is $CH=CHOCH_3$. In a further special embodiment $R^4$ is $CH=CHCH_2OCH_3$. According to a further specific embodiment $R^4$ is $C_1$-$C_4$-haloalkoxy-$C_2$-$C_6$-alkenyl, more preferably $C_1$-$C_4$-haloalkoxy-$C_2$-$C_4$-alkenyl. In a special embodiment $R^4$ is $CH=CHOCF_3$. In a further special embodiment $R^4$ is $CH=CHCH_2OCF_3$. In a further special embodiment $R^4$ is $CH=CHOCCl_3$. In a further special embodiment $R^4$ is $CH=CHCH_2OCCl_3$. According to a further specific embodiment $R^4$ is $C_3$-$C_8$-cycloalkyl-$C_2$-$C_6$-alkenyl, preferably $C_3$-$C_6$-cycloalkyl-$C_2$-$C_4$-alkenyl. According to a further specific embodiment $R^4$ is $C_3$-$C_6$-halocycloalkyl-$C_2$-$C_4$-alkenyl, preferably $C_3$-$C_8$-halocycloalkyl-$C_2$-$C_6$-alkenyl.

According to still a further embodiment, $R^4$ is $C_2$-$C_6$-alkynyl or $C_2$-$C_6$-haloalkynyl, in particular $C_2$-$C_4$-alkynyl or $C_2$-$C_4$-haloalkynyl, such as C≡CH, $CH_2$CCH or $CH_2$CCCH$_3$.

According to a further specific embodiment $R^4$ is $C_2$-$C_6$-alkynyl, preferably $C_2$-$C_4$-alkynyl, substituted by OH, more preferably, CCOH, $CH_2$CCOH. In a special embodiment $R^4$ is CCOH. In a further special embodiment $R^4$ is $CH_2$CCOH. According to a further specific embodiment $R^4$ is $C_1$-$C_4$-alkoxy-$C_2$-$C_6$-alkynyl, more preferably $C_1$-$C_4$-alkoxy-$C_2$-$C_4$-alkynyl. In a special embodiment $R^4$ is CCOCH$_3$. In a further special embodiment $R^4$ is $CH_2$CCOCH$_3$. According to a further specific embodiment $R^4$ is $C_1$-$C_4$-haloalkoxy-$C_2$-$C_6$-alkynyl, more preferably $C_1$-$C_4$-haloalkoxy-$C_2$-$C_4$-alkynyl. In a special embodiment $R^4$ is CCOCF$_3$. In a further special embodiment $R^4$ is $CH_2$CCOCF$_3$. In a further special embodiment $R^4$ is CCOCCl$_3$. In a further special embodiment $R^4$ is $CH_2$CCOCCl$_3$. According to a further specific embodiment $R^4$ is $C_3$-$C_8$-cycloalkyl-$C_2$-$C_6$-alkynyl, preferably $C_3$-$C_6$-cycloalkyl-$C_2$-$C_4$-alkynyl. According to a further specific embodiment $R^4$ is $C_3$-$C_6$-halocycloalkyl-$C_2$-$C_4$-alkynyl, preferably $C_3$-$C_8$-halocycloalkyl-$C_2$-$C_6$-alkynyl.

According to one another embodiment $R^4$ is $C_3$-$C_8$-cycloalkyl, preferably cyclopropyl, cyclobutyl, cyclopentyl or cyclohexyl, in particular cyclopropyl or cyclobutyl. In a special embodiment $R^4$ is cyclopropyl. In a further special embodiment $R^4$ is cyclobutyl. In a further special embodiment $R^4$ is cyclopentyl. In a further special embodiment $R^4$ is cyclohexyl.

According to one another embodiment $R^4$ is $C_3$-$C_8$-cycloalkoxy, preferably $C_3$-$C_6$-cycloalkoxy. In a special embodiment $R^4$ is O-cyclopropyl.

According to a specific embodiment $R^4$ is $C_3$-$C_8$-halocycloalkyl, more preferably fully or partially halogenated $C_3$-$C_6$-cycloalkyl. In a special embodiment $R^4$ is fully or partially halogenated cyclopropyl. In a further special embodiment $R^4$ is 1-Cl-cyclopropyl. In a further special embodiment $R^4$ is 2-Cl-cyclopropyl. In a further special embodiment $R^4$ is 1-F-cyclopropyl. In a further special embodiment $R^4$ is 2-F-cyclopropyl. In a further special embodiment $R^4$ is fully or partially halogenated cyclobutyl. In a further special embodiment $R^4$ is 1-Cl-cyclobutyl. In a further special embodiment $R^4$ is 1-F-cyclobutyl. In a further special embodiment $R^4$ is 3,3-Cl$_2$-cyclobutyl. In a further special embodiment $R^4$ is 3,3-F$_2$-cyclobutyl. According to a specific embodiment $R^4$ is $C_3$-$C_8$-cycloalkyl substituted by $C_1$-$C_4$-alkyl, more preferably is $C_3$-$C_6$-cycloalkyl substituted by $C_1$-$C_4$-alkyl. In a special embodiment $R^4$ is 1-CH$_3$-cyclopropyl. According to a specific embodiment $R^4$ is $C_3$-$C_8$-cycloalkyl substituted by CN, more preferably is $C_3$-$C_6$-cycloalkyl substituted by CN. In a special embodiment $R^4$ is 1-CN-cyclopropyl. According to a further specific embodiment $R^4$ is $C_3$-$C_8$-cycloalkyl-$C_3$-$C_8$-cycloalkyl, preferably $C_3$-$C_6$-cycloalkyl-$C_3$-$C_6$-cycloalkyl. In a special embodiment $R^4$ is cyclopropyl-cyclopropyl. In a special embodiment $R^4$ is 2-cyclopropyl-cyclopropyl. According to a further specific embodiment $R^4$ is $C_3$-$C_8$-cycloalkyl-$C_3$-$C_8$-halocycloalkyl, preferably $C_3$-$C_6$-cycloalkyl-$C_3$-$C_6$-halocycloalkyl.

According to one another embodiment $R^4$ is $C_3$-$C_8$-cycloalkyl-$C_1$-$C_4$-alkyl, preferably $C_3$-$C_6$-cycloalkyl-$C_1$-$C_4$-alkyl. In a further special embodiment $R^4$ is CH(CH$_3$)(cyclopropyl). In a further special embodiment $R^4$ is $CH_2$-(cyclopropyl).

According to a further preferred embodiment $R^4$ is $C_3$-$C_8$-cycloalkyl-$C_1$-$C_4$-alkyl wherein the alkyl moiety can be substituted by one, two, three or up to the maximum possible number of identical or different groups $R^a$ as defined and preferably herein and the cycloalkyl moiety can be substituted by one, two, three or up to the maximum possible number of identical or different groups Rb as defined and preferably herein.

According to a specific embodiment $R^4$ is $C_3$-$C_8$-cycloalkyl-$C_1$-$C_4$-haloalkyl, $C_3$-$C_6$-cycloalkyl-$C_1$-$C_4$-haloalkyl. According to a specific embodiment $R^4$ is $C_3$-$C_8$-halocycloalkyl-$C_1$-$C_4$-alkyl, $C_3$-$C_6$-halocycloalkyl-$C_1$-$C_4$-alkyl. In a special embodiment $R^4$ is fully or partially halogenated cyclopropyl-$C_1$-$C_4$-alkyl. In a further special embodiment $R^4$ is 1-Cl-cyclopropyl-$C_1$-$C_4$-alkyl. In a further special embodiment $R^4$ is 1-F-cyclopropyl-$C_1$-$C_4$-alkyl.

According to one another embodiment $R^4$ is NH$_2$.

According to one another embodiment $R^4$ is NH($C_1$-$C_4$-alkyl). According to a specific embodiment $R^4$ is NH(CH$_3$). According to a specific embodiment $R^4$ is NH(CH$_2$CH$_3$). According to a specific embodiment $R^4$ is NH(CH$_2$CH$_2$CH$_3$). According to a specific embodiment $R^4$ is NH(CH(CH$_3$)$_2$). According to a specific embodiment $R^4$ is NH(CH$_2$CH$_2$CH$_2$CH$_3$). According to a specific embodiment $R^4$ is NH(C(CH$_3$)$_3$).

According to one another embodiment $R^4$ is N($C_1$-$C_4$-alkyl)$_2$. According to a specific embodiment $R^4$ is N(CH$_3$)$_2$. According to a specific embodiment $R^4$ is N(CH$_2$CH$_3$)$_2$. According to a specific embodiment $R^4$ is N(CH$_2$CH$_2$CH$_3$)$_2$. According to a specific embodiment $R^4$ is N(CH(CH$_3$)$_2$)$_2$. According to a specific embodiment $R^4$ is N(CH$_2$CH$_2$CH$_2$CH$_3$)$_2$. According to a specific embodiment $R^4$ is NH(C(CH$_3$)$_3$)$_2$.

According to one another embodiment $R^4$ is NH($C_3$-$C_8$-cycloalkyl) preferably NH($C_3$-$C_6$-cycloalkyl). According to a specific embodiment $R^4$ is NH(cyclopropyl). According to a specific embodiment $R^4$ is NH(cyclobutyl). According to a specific embodiment $R^4$ is NH(cyclopentyl). According to a specific embodiment $R^4$ is NH(cyclohexyl).

According to one another embodiment $R^4$ is N($C_3$-$C_8$-cycloalkyl)$_2$ preferably N($C_3$-$C_6$-cycloalkyl)$_2$. According to a specific embodiment $R^4$ is N(cyclopropyl)$_2$. According to a specific embodiment $R^4$ is N(cyclobutyl)$_2$. According to a specific embodiment $R^4$ is N(cyclopentyl)$_2$. According to a specific embodiment $R^4$ is N(cyclohexyl)$_2$.

According to still a further embodiment, $R^4$ is selected from C(=O)($C_1$-$C_4$-alkyl), C(=O)(OH), C(=O)(O—$C_1$-$C_4$-alkyl), C(=O)(NH($C_1$-$C_4$-alkyl)), C(=O)(N($C_1$-$C_4$-alkyl)$_2$), C(=O)(NH($C_3$-$C_6$-cycloalkyl)) and C(=O)(N($C_3$-$C_6$-cycloalkyl)$_2$), in particular selected from C(=O)($C_1$-$C_2$-alkyl), C(=O)(OH), C(=O)(O—$C_1$-$C_2$-alkyl), C(=O)(NH($C_1$-$C_2$-alkyl)), C(=O)(N($C_1$-$C_2$-alkyl)$_2$), C(=O)(NH($C_3$-$C_6$-cycloalkyl)) and C(=O)(N($C_3$-$C_6$-cycloalkyl)$_2$). According to one specific embodiment thereof, $R^4$ is C(=O)(OH) or C(=O)(O—$C_1$-$C_4$-alkyl), in particular C(=O)(OCH$_3$).

According to one another embodiment $R^4$ is C(=O)(—$C_1$-$C_4$-alkyl). According to a specific embodiment $R^4$ is C(=O)CH$_3$. According to a further specific embodiment $R^4$ is C(=O)CH$_2$CH$_3$. According to a further specific embodiment $R^4$ is C(=O)CH$_2$CH$_2$CH$_3$. According to a further specific embodiment $R^4$ is $C(=O)CH(CH_3)_2$. According to a further specific embodiment $R^4$ is $C(=O)C(CH_3)_3$.

According to one another embodiment $R^4$ is $C(=O)OH$.

According to one another embodiment $R^4$ is $C(=O)(-O-C_1-C_4$-alkyl). According to a specific embodiment $R^4$ is $C(=O)OCH_3$. According to a further specific embodiment $R^4$ is $C(=O)OCH_2CH_3$.

According to a further specific embodiment $R^4$ is $C(=O)OCH_2CH_2CH_3$. According to a further specific embodiment $R^4$ is $C(=O)OCH(CH_3)_2$. According to a further specific embodiment $R^4$ is $C(=O)OC(CH_3)_3$.

According to one another embodiment $R^4$ is $C(=O)-NH(C_1-C_4$-alkyl). According to a specific embodiment $R^4$ is $C(=O)NHCH_3$. According to a further specific embodiment $R^4$ is $C(=O)NHCH_2CH_3$.

According to a further specific embodiment $R^4$ is $C(=O)NHCH_2CH_2CH_3$. According to a further specific embodiment $R^4$ is $C(=O)NHCH(CH_3)_2$. According to a further specific embodiment $R^4$ is $C(=O)NHC(CH_3)_3$.

According to one another embodiment $R^4$ is $C(=O)-N(C_1-C_4$-alkyl)$_2$. According to a specific embodiment $R^4$ is $C(=O)N(CH_3)_2$. According to a further specific embodiment $R^4$ is $C(=O)N(CH_2CH_3)_2$. According to a further specific embodiment $R^4$ is $C(=O)N(CH_2CH_2CH_3)_2$. According to a further specific embodiment $R^4$ is $C(=O)N(CH(CH_3)_2)_2$. According to a further specific embodiment $R^4$ is $C(=O)N(C(CH_3)_3)_2$.

According to one another embodiment $R^4$ is $C(=O)-NH(C_3-C_6$-cycloalkyl). According to a specific embodiment $R^4$ is $C(=O)NH(cyclopropyl)$. According to a further specific embodiment $R^4$ is $C(=O)NH(cyclobutyl)$ According to a further specific embodiment $R^4$ is $C(=O)NH(cyclopentyl)$ According to a further specific embodiment $R^4$ is $C(=O)NH(cyclohexyl)$.

According to one another embodiment $R^4$ is $C(=O)-N(C_3-C_6$-cycloalkyl)$_2$. According to a specific embodiment $R^4$ is $C(=O)N(cyclopropyl)_2$. According to a further specific embodiment $R^4$ is $C(=O)N(cyclobutyl)_2$. According to a further specific embodiment $R^4$ is $C(=O)N(cyclopentyl)_2$. According to a further specific embodiment $R^4$ is $C(=O)N(cyclohexyl)_2$.

According to still a further embodiment, $R^4$ is selected from $S(C_1-C_2$-alkyl), $S(O)(C_1-C_2$-alkyl) and $S(O)_2(C_1-C_2$-alkyl), in particular $SCH_3$, $S(O)(CH_3)$ and $S(O)_2(CH_3)$. According to a specific embodiment $R^4$ is selected from $S(C_1-C_2$-haloalkyl), $S(O)(C_1-C_2$-haloalkyl) and $S(O)_2(C_1-C_2$-haloalkyl), such as $SO_2CF_3$.

Particularly preferred embodiments of $R^4$ according to the invention are in Table P4 below, wherein each line of lines P4-1 to P4-16 corresponds to one particular embodiment of the invention, wherein P4-1 to P4-16 are also in any combination with one another a preferred embodiment of the present invention. Thereby, for every $R^4$ that is present in the inventive compounds, these specific embodiments and preferences apply independently of the meaning of any other $R^4$ that may be present in the phenyl ring:

TABLE P4

| No. | $R^4$ |
|---|---|
| P4-1 | Cl |
| P4-2 | F |
| P4-3 | CN |
| P4-4 | $NO_2$ |
| P4-5 | $CH_3$ |
| P4-6 | $CH_2CH_3$ |
| P4-7 | $CF_3$ |
| P4-8 | $CHF_2$ |
| P4-9 | $OCH_3$ |
| P4-10 | $OCH_2CH_3$ |
| P4-11 | $OCF_3$ |
| P4-12 | $OCHF_2$ |
| P4-13 | $SCH_3$ |
| P4-14 | $SOCH_3$ |
| P4-15 | $SO_2CH_3$ |
| P4-16 | $CO_2CH_3$ |

Particularly preferred embodiments of $(R^4)_m$ according to the invention are in Table P44 below, wherein each line of lines P44-1 to P44-155 corresponds to one particular embodiment of the invention, wherein P44-1 to P44-155 are also in any combination a preferred embodiment of the present invention.

TABLE P44

| No. | $(R^4)_m$ |
|---|---|
| P44-1 | —* |
| P44-2 | 2-Cl |
| P44-3 | 3-Cl |
| P44-4 | 4-Cl |
| P44-5 | 2-F |
| P44-6 | 3-F |
| P44-7 | 4-F |
| P44-8 | 2-CN |
| P44-9 | 3-CN |
| P44-10 | 4-CN |
| P44-11 | 2-$NO_2$ |
| P44-12 | 3-$NO_2$ |
| P44-13 | 4-$NO_2$ |
| P44-14 | 2-$SCH_3$ |
| P44-15 | 3-$SCH_3$ |
| P44-16 | 4-$SCH_3$ |
| P44-17 | 2-$SOCH_3$ |
| P44-18 | 3-$SOCH_3$ |
| P44-19 | 4-$SOCH_3$ |
| P44-20 | 2-$SO_2CH_3$ |
| P44-21 | 3-$SO_2CH_3$ |
| P44-22 | 4-$SO_2CH_3$ |
| P44-23 | 2-$CO_2CH_3$ |
| P44-24 | 3-$CO_2CH_3$ |
| P44-25 | 4-$CO_2CH_3$ |
| P44-26 | 2,3-$Cl_2$ |
| P44-27 | 2,4-$Cl_2$ |
| P44-28 | 2,5-$Cl_2$ |
| P44-29 | 3,4-$Cl_2$ |
| P44-30 | 3,5-$Cl_2$ |
| P44-31 | 2,6-$Cl_2$ |
| P44-32 | 2,3-$F_2$ |
| P44-33 | 2,4-$F_2$ |
| P44-34 | 2,5-$F_2$ |
| P44-35 | 3,4-$F_2$ |
| P44-36 | 3,5-$F_2$ |
| P44-37 | 2,6-$F_2$ |
| P44-38 | 2-F-3-Cl |
| P44-39 | 2-F-4-Cl |
| P44-40 | 3-F-4-Cl |
| P44-41 | 2-F-6-Cl |
| P44-42 | 2-Cl-3-F |
| P44-43 | 2-Cl-4-F |
| P44-44 | 3-Cl-4-F |
| P44-45 | 2,3,4-$Cl_3$ |
| P44-46 | 2,4,5-$Cl_3$ |
| P44-47 | 3,4,5-$Cl_3$ |
| P44-48 | 2,4,6-$Cl_3$ |
| P44-49 | 2,3,4-$F_3$ |
| P44-50 | 2,4,5-$F_3$ |
| P44-51 | 3,4,5-$F_3$ |
| P44-52 | 2,4,6-$F_3$ |
| P44-53 | 2,3-4-$F_3$ |
| P44-54 | 2,4-$F_2$-3-Cl |

TABLE P44-continued

| No. | $(R^4)_m$ |
|---|---|
| P44-55 | 2,6-F$_2$-4-Cl |
| P44-56 | 2,5-F$_2$-4-Cl |
| P44-57 | 2,4-Cl$_2$-3-F |
| P44-58 | 2,6-Cl$_2$-4-F |
| P44-59 | 2,5-Cl$_2$-4-F |
| P44-60 | 2-CH$_3$ |
| P44-61 | 3-CH$_3$ |
| P44-62 | 4-CH$_3$ |
| P44-63 | 2-CH$_2$CH$_3$ |
| P44-64 | 3-CH$_2$CH$_3$ |
| P44-65 | 4-CH$_2$CH$_3$ |
| P44-66 | 2-CF$_3$ |
| P44-67 | 3-CF$_3$ |
| P44-68 | 4-CF$_3$ |
| P44-69 | 2-CHF$_2$ |
| P44-70 | 3-CHF$_2$ |
| P44-71 | 4-CHF$_2$ |
| P44-72 | 2-OCH$_3$ |
| P44-73 | 3-OCH$_3$ |
| P44-74 | 4-OCH$_3$ |
| P44-75 | 2-OCH$_2$CH$_3$ |
| P44-76 | 3-OCH$_2$CH$_3$ |
| P44-77 | 4-OCH$_2$CH$_3$ |
| P44-78 | 2-OCF$_3$ |
| P44-79 | 3-OCF$_3$ |
| P44-80 | 4-OCF$_3$ |
| P44-81 | 2-OCHF$_2$ |
| P44-82 | 3-OCHF$_2$ |
| P44-83 | 4-OCHF$_2$ |
| P44-84 | 2,3-(CH$_3$)$_2$ |
| P44-85 | 2,4-(CH$_3$)$_2$ |
| P44-86 | 3,4-(CH$_3$)$_2$ |
| P44-87 | 2,6-(CH$_3$)$_2$ |
| P44-88 | 2,3-(CH$_2$CH$_3$)$_2$ |
| P44-89 | 2,4-(CH$_2$CH$_3$)$_2$ |
| P44-90 | 3,4-(CH$_2$CH$_3$)$_2$ |
| P44-91 | 2,6-(CH$_2$CH$_3$)$_2$ |
| P44-92 | 2,3-(CF$_3$)$_2$ |
| P44-93 | 2,4-(CF$_3$)$_2$ |
| P44-94 | 3,4-(CF$_3$)$_2$ |
| P44-95 | 2,6-(CF$_3$)$_2$ |
| P44-96 | 2,3-(CHF$_2$)$_2$ |
| P44-97 | 2,4-(CHF$_2$)$_2$ |
| P44-98 | 3,4-(CHF$_2$)$_2$ |
| P44-99 | 2,6-(CHF$_2$)$_2$ |
| P44-100 | 2,3-(OCH$_3$)$_2$ |
| P44-101 | 2,4-(OCH$_3$)$_2$ |
| P44-102 | 3,4-(OCH$_3$)$_2$ |
| P44-103 | 2,6-(OCH$_3$)$_2$ |
| P44-104 | 2,3-(OCH$_2$CH$_3$)$_2$ |
| P44-105 | 2,4-(OCH$_2$CH$_3$)$_2$ |
| P44-106 | 3,4-(OCH$_2$CH$_3$)$_2$ |
| P44-107 | 2,6-(OCH$_2$CH$_3$)$_2$ |
| P44-108 | 2,3-(OCF$_3$)$_2$ |
| P44-109 | 2,4-(OCF$_3$)$_2$ |
| P44-110 | 3,4-(OCF$_3$)$_2$ |
| P44-111 | 2,6-(OCF$_3$)$_2$ |
| P44-112 | 2,3-(OCHF$_2$)$_2$ |
| P44-113 | 2,4-(OCHF$_2$)$_2$ |
| P44-114 | 3,4-(OCHF$_2$)$_2$ |
| P44-115 | 2,6-(OCHF$_2$)$_2$ |
| P44-116 | 2,3,4-(CH$_3$)$_3$ |
| P44-117 | 2,4,5-(CH$_3$)$_3$ |
| P44-118 | 3,4,5-(CH$_3$)$_3$ |
| P44-119 | 2,4,6-(CH$_3$)$_3$ |
| P44-120 | 2,3,4-(CH$_2$CH$_3$)$_3$ |
| P44-121 | 2,4,5-(CH$_2$CH$_3$)$_3$ |
| P44-122 | 3,4,5-(CH$_2$CH$_3$)$_3$ |
| P44-123 | 2,4,6-(CH$_2$CH$_3$)$_3$ |
| P44-124 | 2,3,4-(CF$_3$)$_3$ |
| P44-125 | 2,4,5-(CF$_3$)$_3$ |
| P44-126 | 3,4,5-(CF$_3$)$_3$ |
| P44-127 | 2,4,6-(CF$_3$)$_3$ |
| P44-128 | 2,3,4-(CHF$_2$)$_3$ |
| P44-129 | 2,4,5-(CHF$_2$)$_3$ |
| P44-130 | 3,4,5-(CHF$_2$)$_3$ |
| P44-131 | 2,4,6-(CHF$_2$)$_3$ |
| P44-132 | 2,3,4-(OCH$_3$)$_3$ |
| P44-133 | 2,4,5-(OCH$_3$)$_3$ |
| P44-134 | 3,4,5-(OCH$_3$)$_3$ |
| P44-135 | 2,4,6-(OCH$_3$)$_3$ |
| P44-136 | 2,3,4-(OCH$_2$CH$_3$)$_3$ |
| P44-137 | 2,4,5-(OCH$_2$CH$_3$)$_3$ |
| P44-138 | 3,4,5-(OCH$_2$CH$_3$)$_3$ |
| P44-139 | 2,4,6-(OCH$_2$CH$_3$)$_3$ |
| P44-140 | 2,3,4-(OCF$_3$)$_3$ |
| P44-141 | 2,4,5-(OCF$_3$)$_3$ |
| P44-142 | 3,4,5-(OCF$_3$)$_3$ |
| P44-143 | 2,4,6-(OCF$_3$)$_3$ |
| P44-144 | 2,3,4-(OCHF$_2$)$_3$ |
| P44-145 | 2,4,5-(OCHF$_2$)$_3$ |
| P44-146 | 3,4,5-(OCHF$_2$)$_3$ |
| P44-147 | 2,4,6-(OCHF$_2$)$_3$ |
| P44-148 | 2-CF$_3$-4-Cl |
| P44-149 | 2-CF$_3$-4-F |
| P44-150 | 2-Cl-4-CF$_3$ |
| P44-151 | 2-F-4-CF$_3$ |
| P44-152 | 2-CN-4-Cl |
| P44-153 | 2-CN-4-F |
| P44-154 | 2-Cl-4-CN |
| P44-155 | 2-F-4-CN |

In particular, in the inventive process, compounds III.a are used to obtain compounds II.a and, then may be further reacted to compounds Ia, and optionally further reacted to the respective I-1 compounds (containing "OR$^2$" see above):

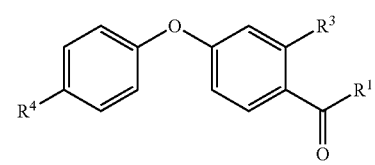

III.a

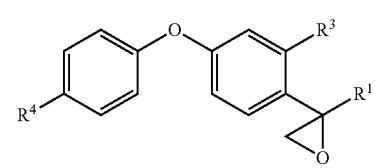

II.a

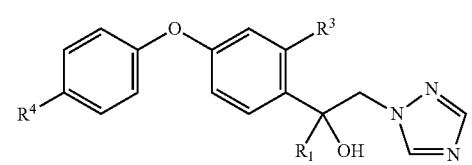

I.a

Wherein the substituents are as defined and preferably defined above. In particular, the substituents have the following preferred meanings. There, the specific meanings of the respective substituents are in each case on their own but also in any combination with one another, particular embodiments of the present invention.

According to one particular embodiment of the invention, in the compounds I (or I-1), II and III, respectively, $R^1$ is $(C_1-C_4)$-alkyl, $(C_3-C_6)$-cycloalkyl or $(C_2-C_4)$-alkinyl. Preferably, $R^1$ is $(C_1-C_4)$-alkyl, $(C_3)$-cycloalkyl or $(C_3)$-alkinyl. In one specific embodiment thereof, $R^1$ is $CH_3$. In a further specific embodiment $R^1$ is $C_2H_5$. In still a further specific embodiment $R^1$ is n-$(C_3H_7)$. In still a further specific embodiment $R^1$ is i-$(C_3H_7)$. In still a further specific embodiment $R^1$ is $C(CH_3)_3$. In still a further embodiment $R^1$ is cyclopropyl. In still a further embodiment $R^1$ is $C\equiv C-CH_3$.

According to one particular embodiment of the invention, in the compounds I-1, $R^2$ is $(C_1-C_3)$-alkyl, $(C_2-C_4)$-alkenyl or $(C_2-C_4)$-alkynyl, in particular hydrogen, $(C_1-C_3)$-alkyl, $(C_2-C_3)$-alkenyl or $(C_2-C_4)$-alkynyl. Preferably, $R^2$ is $(C_1-C_3)$-alkyl. In a further specific embodiment $R^2$ is $CH_3$. In still a further specific embodiment $R^2$ is $C_2H_5$. In still a further specific embodiment $R^2$ is n-$(C_3H_7)$. In still a further specific embodiment $R^2$ is i-$(C_3H_7)$. In still a further specific embodiment $R^2$ is $CH_2CH=CH_2$ (allyl). In still a further specific embodiment $R^2$ is $CH_2C(CH_3)=CH_2$. In still a further specific embodiment $R^2$ is $CH_2C\equiv CH$.

According to one particular embodiment of the invention, in the compounds I (or I-1), II and III, respectively, $R^3$ is Cl or $CF_3$. In one embodiment $R^3$ is $C_1$. In the further embodiment, $R^3$ is $CF_3$.

According to one particular embodiment of the invention, in the compounds I (or I-1), II and III, respectively, $R^4$ is Cl or F. In one embodiment $R^4$ is Cl. In the further embodiment $R^4$ is F.

Specifically, the following compounds I.1 to I.18 and I.19 to I.31 can advantageously be prepared using the process according to the present invention:

compound I.1 2-[2-chloro-4-(4-chlorophenoxy)phenyl]-1-(1,2,4-triazol-1-yl)pent-3-yn-2-ol;
compound I.2 1-[2-chloro-4-(4-chlorophenoxy)phenyl]-1-cyclopropyl-2-(1,2,4-triazol-1-yl)ethanol;
compound I.3 2-[4-(4-chlorophenoxy)-2-(trifluoromethyl)phenyl]-1-(1,2,4-triazol-1-yl)propan-2-ol;
compound I.4 1-[4-(4-chlorophenoxy)-2-(trifluoromethyl)phenyl]-1-cyclopropyl-2-(1,2,4-triazol-1-yl)ethanol;
compound I.5 2-[4-(4-chlorophenoxy)-2-(trifluoromethyl)phenyl]-3-methyl-1-(1,2,4-triazol-1-yl)butan-2-ol;
compound I.6 1-[2-[2-chloro-4-(4-chlorophenoxy)phenyl]-2-methoxy-pent-3-ynyl]-1,2,4-triazole;
compound I.7 2-[4-(4-chlorophenoxy)-2-(trifluoromethyl)phenyl]-1-(1,2,4-triazol-1-yl)butan-2-ol;
compound I.8 1-[2-[2-chloro-4-(4-chlorophenoxy)phenyl]-2-cyclopropyl-2-methoxy-ethyl]-1,2,4-triazole;
compound I.9 1-[2-[4-(4-chlorophenoxy)-2-(trifluoromethyl)phenyl]-2-methoxy-propyl]-1,2,4-triazole;
compound I.10 2-[2-chloro-4-(4-chlorophenoxy)phenyl]-3,3-dimethyl-1-(1,2,4-triazol-1-yl)butan-2-ol,
compound I.11 1-[2-[4-(4-chlorophenoxy)-2-(trifluoromethyl)phenyl]-2-cyclopropyl-2-methoxy-ethyl]-1,2,4-triazole;
compound I.12 1-[2-[2-chloro-4-(4-chlorophenoxy)phenyl]-2-methoxy-3,3-dimethyl-butyl]-1,2,4-triazole;
compound I.13 1-[2-[4-(4-chlorophenoxy)-2-(trifluoromethyl)phenyl]-2-methoxy-butyl]1,2,4-triazole;
compound I.14 2-[4-(4-chlorophenoxy)-2-(trifluoromethyl)phenyl]-1-(1,2,4-triazol-1-yl)pent-3-yn-2-ol;
compound I.15 1-[2-[4-(4-chlorophenoxy)-2-(trifluoromethyl)phenyl]-2-methoxy-pent-3-ynyl]-1,2,4-triazole;
compound I.16 2-[4-(4-chlorophenoxy)-2-(trifluoromethyl)phenyl]-1-(1,2,4-triazol-1-yl)but-3-yn-2-ol;
compound I.17 2-[2-chloro-4-(4-chlorophenoxy)phenyl]-1-(1,2,4-triazol-1-yl)propan-2-ol; and
compound I.18 2-[2-chloro-4-(4-fluorophenoxy)phenyl]-1-(1,2,4-triazol-1-yl)propan-2-ol.
compound I.19 2-[2-chloro-4-(4-chlorophenoxy)phenyl]-3-methyl-1-(1,2,4-triazol-1-yl)butan-2-01;
compound I.20 1-[2-[2-chloro-4-(4-chlorophenoxy)phenyl]-2-methoxy-propyl]-1,2,4-triazole;
compound I.21 1-[2-[2-chloro-4-(4-chlorophenoxy)phenyl]-2-methoxy-butyl]-1,2,4-riazole;
compound I.22 1-[2-[2-chloro-4-(4-chlorophenoxy)phenyl]-2-methoxy-pentyl]-1,2,4-triazole;
compound I.23 2-[2-chloro-4-(4-chlorophenoxy)phenyl]-1,1,1-trifluoro-3-(1,2,4-triazol-1-yl)propan-2-ol;
compound I.24 2-[2-chloro-4-(4-chlorophenoxy)phenyl]-3-fluoro-1-(1,2,4-triazol-1-yl)butan-2-ol hydrochloride;
compound I.25 2-[2-chloro-4-(4-chlorophenoxy)phenyl]-1-(1,2,4-triazol-1-yl)pent-4-yn-2-ol;
compound I.26 2-[2-chloro-4-(4-chlorophenoxy)phenyl]-1-methoxy-3-(1,2,4-triazol-1-yl)propan-2-ol;
compound I.27 2-[2-chloro-4-(4-fluorophenoxy)phenyl]-1-methoxy-3-(1,2,4-triazol-1-yl)propan-2-ol;
compound I.28 2-[4-(4-chlorophenoxy)-2-(trifluoromethyl)phenyl]-1-(1,2,4-triazol-1-yl)pentan-2-ol;
compound I.29 and 2-[4-(4-fluorophenoxy)-2-(trifluoromethyl)phenyl]-1-(1,2,4-triazol-1-yl)propan-2-ol;
compound I.30 2-[2-chloro-4-(4-chlorophenoxy)phenyl]-1-(1,2,4-triazol-1-yl)butan-2-ol; and
compound I.31 2-[2-chloro-4-(4-chlorophenoxy)phenyl]-1-(1,2,4-triazol-1-yl)pentan-2-ol.

Specifically, the following compounds IC.1 to IC.7 can advantageously be prepared using the process according to the present invention:

compound IC.1 2-[4-(4-chlorophenoxy)-2-(trifluoromethyl)phenyl]-1-(1,2,4-triazol-1-yl)propan-2-ol;
compound IC.2 1-[4-(4-chlorophenoxy)-2-(trifluoromethyl)phenyl]-1-cyclopropyl-2-(1,2,4-triazol-1-yl)ethanol;
compound IC.3 2-[4-(4-chlorophenoxy)-2-(trifluoromethyl)phenyl]-3-methyl-1-(1,2,4-triazol-1-yl)butan-2-ol;
compound IC.4 2-[4-(4-chlorophenoxy)-2-(trifluoromethyl)phenyl]-1-(1,2,4-triazol-1-yl)butan-2-ol;
compound IC.5 1-[2-[4-(4-chlorophenoxy)-2-(trifluoromethyl)phenyl]-2-methoxy-propyl]-1,2,4-triazole;
compound IC.6 1-[2-[4-(4-chlorophenoxy)-2-(trifluoromethyl)phenyl]-2-cyclopropyl-2-methoxy-ethyl]-1,2,4-triazole;
compound IC.7 1-[2-[4-(4-chlorophenoxy)-2-(trifluoromethyl)phenyl]-2-methoxy-butyl]1,2,4-triazole.

Compounds I comprise chiral centers and they are generally obtained in the form of racemates. The R- and S-enantiomers of the compounds can be separated and isolated in pure form with methods known by the skilled person, e.g. by using chiral HPLC. Furthermore, components I can be present in different crystal modifications, which may differ in biological activity.

The compounds according to the invention may be present in various crystal modifications.

They are likewise provided by the present invention.

Furthermore, using the inventive crystallization step, solvates may occur, in particular from any one of compounds I.1 to I.18 that are likewise comprised by the present invention. A further aspect of the invention is, therefore, a crystalline solvate of compound I, in particular a crystalline solvate with a compounds I selected from I.1, I.2, I.3, I.4, I.5, I.6, I.7, I.8, I.9, I.10, I.11, I.12, I.13, I.14, I.15, I.16, I.17 and I.18. In particular, the solvate is formed using an aliphatic alcohol as detailed abovem, in particular methanol or ethanol.

It was surprisingly found that the process of the present invention allows to prepare a specific crystalline form of 2-[4-(4-chlorophenoxy)-2-(trifluoromethyl)phenyl]-1-(1,2,4-triazol-1-yl)propane-2-ol (compound I.3), hereinafter also termed form A of compound I.3, which has not yet been described so far and which has beneficial properties in comparison with the known solid forms of the compound I.3. 2-[4-(4-chlorophenoxy)-2-(trifluoromethyl)phenyl]-1-(1,2,4-triazol-1-yl)propane-2-ol is a compound of formula I, where R1 is methyl, $(R^3)_n$ is trifloromethyl, which is located in the meta position with respect to the phenoxy radical and is $(R^4)_m$ chlorine, which is located para with respect to the oxygen atom.

Form A of compound I.3 can be characterized by its X-ray powder diffractogram at 25° C. using Cu—$K_\alpha$ radiation. Said X-ray powder diffractogram shows at least six, in particular at least 8, more particularly at least 10 or 12 and especially all of the fifteen following reflexes, given in the following table 1 as 2θ values and d-spacings:

TABLE 1

Relevant reflections in the XRPD pattern of crystalline form of Form A of compound I.3

| 2θ values [°] | d [Å] |
|---|---|
| 9.16 ± 0.2 | 9.65 |
| 13.95 ± 0.2 | 6.35 |
| 15.35 ± 0.2 | 5.77 |
| 16.04 ± 0.2 | 5.52 |
| 16.51 ± 0.2 | 5.37 |
| 17.17 ± 0.2 | 5.17 |
| 18.26 ± 0.2 | 4.86 |
| 18.89 ± 0.2 | 4.70 |
| 20.59 ± 0.2 | 4.31 |
| 21.11 ± 0.2 | 4.21 |
| 21.49 ± 0.2 | 4.14 |
| 22.33 ± 0.2 | 3.98 |
| 22.60 ± 0.2 | 3.93 |
| 23.26 ± 0.2 | 3.82 |
| 26.46 ± 0.2 | 3.37 |

A skilled person appreciates understands that Cu—$K_\alpha$ radiation is electromagnetic radiation having maximum intensity at wavelength of 1.54178 Å.

Therefore, a further aspect of the present invention relates to a crystalline form A of 2-[4-(4-chlorophenoxy)-2-(trifluoromethyl)phenyl]-1-(1,2,4-triazol-1-yl)propane-2-ol, as described above.

The crystal form A of compound I.3 according to the invention is easier to handle than the previously known form of compound I.3 (known e.g. from PCT/EP2012/063626), since during production form A is obtained in the form of discrete crystals or crystallites having increased particle size in comparison to other forms of compound I.3. Increased particle size and the compact habit of form A facilitates filtration from mother liquour and allows easier drying of the solid material.

Compared to the known forms of compound I.3, pure form A is likely to display increased stability with regard to conversion into another modification. The stability of formulations which contain the compound I.3 in form A is likely higher than the stability of formulations which contain mixtures of different modifications of compound I.3. The terms "pure form A" should be understood to mean that the proportion of the modification in question, based on the total quantity of compound I.3, is at least 80% by weight in particular at least 90% by weight and especially at least 95% by weight. Accordingly, a further object of the present invention relates a composition of the compound I.3 which at least 80% by weight, in particular at least 90% by weight or at least 95% by weight consists of the crystalline form A, based on the total amount of the compound I.3, contained in the composition.

Furthermore, form A of compound I.3 may be distinguished from the known forms of compound I.3 by differences in one or more of the following properties: solubility, vapor pressure, dissolution rate, stability against a phase change into a different modification, stability during grinding, suspension stability, optical and mechanical properties, hygroscopicity, crystal form and size, filterability, density, melting point, stability to decomposition, color and even chemical reactivity or biological activity.

Studies on single crystals of form A of compound I.3 demonstrate that the underlying crystal structure is orthorhombic. The unit cell has the space group Iba2. The characteristic data of the crystal structure of form A (determined at 100 K, Cu—$K_\alpha$ radiation) are compiled in the following table 2.

TABLE 2

Crystallographic characteristics of form A of compound I.3

| Parameter | Form A |
|---|---|
| class | orthorhombic |
| space group | Iba2 |
| a | 38.612(2) Å |
| b | 8.5677(5) Å |
| c | 10.6625(6) Å |
| α | 90° |
| β | 90° |
| γ | 90° |
| volume | 3527.3(3) Å³ |
| Z | 8 |
| R factor | 10.81% | a, b, c = unit cell length
α, β, γ = unit cell angle
Z = number of molecules in the unit cell Form A of compound I.3 displays a thermogram with a characteristic melting peak in the range from 120 to 135° C. The melting point, determined as the onset of the melting peak, typically lies in the range from about 125° C. to 126° C. The values quoted here relate to values determined by differential calorimetry (differential scanning calorimetry: DSC, crimped but vented aluminium pans, heating rate 10 K/min, vented with nitrogen 150 ml/min).

Form A of compound I.3 was prepared by example C.1 as described hereinafter, followed by crystallization from a solution of compound I.3 in an aromatic hydrocarbon solvents, such as toluene. Preferably, crystallization is achieved by cooling a hot solution of compound I.3 in the aromatic hydrocarbon solvent. Preferably, the hot solution has a temperature of at least 60°, e.g. from 70 to 110° C. Preferably cooling is performed with controlled cooling rate, the cooling rate being in particular from 1 to 20 k/h, in particular from 2 to 10 k/h. Single crystals of form A of compound I.3 were obtained from slow evaporation of a solution of compound I.3 in acetonitrile.

The crystallization of form A can be promoted or accelerated by seeding with seed crystals of form A of compound I.3, for example by adding seed crystals of form 3 before or during the crystallization. If seed crystals are added during the crystallization, the quantity thereof is typically 0.001 to 10 wt. %, often 0.005 to 5 wt. %, in particular 0.01 to 1 wt. % and especially 0.05 to 0.5 wt. %, based on the total amount of compound I.3 to be crystallized.

It was also surprisingly found that the process of the present invention allows to prepare a specific crystalline form of 2-[4-(4-chlorophenoxy)-2-(trifluoromethyl)phenyl]-3-methyl-1-(1,2,4-triazol-1-yl)butane-2-ol (compound I.5), hereinafter also termed form A of compound I.5, which has not yet been described so far and which has beneficial properties in comparison with the known solid forms of the compound I.5. 2-[4-(4-chlorophenoxy)-2-(trifluoromethyl) phenyl]-3-methyl-1-(1,2,4-triazol-1-yl)butane-2-ol is a compound of formula I, where $R^1$ is isopropyl, $(R^3)_n$ is trifloromethyl, which is located in the meta position with respect to the phenoxy radical and is $(R^4)_m$ chlorine, which is located para with respect to the oxygen atom.

Form A of compound I.5 can be characterized by its X-ray powder diffractogram at 25° C. and Cu—$K_\alpha$ radiation, which shows at least six, in particular at least 8, more particularly at least 10 or 12 and especially all of the fourteen following reflexes, given as 2θ values and d-spacings in the following table 3:

TABLE 3

Relevant reflections in the XRPD pattern of compound I.5 form A

| 2θ values [°] | d [Å] |
|---|---|
| 6.26 ± 0.2 | 14.11 |
| 11.68 ± 0.2 | 7.58 |
| 12.52 ± 0.2 | 7.07 |
| 13.64 ± 0.2 | 6.49 |
| 14.69 ± 0.2 | 6.03 |
| 18.84 ± 0.2 | 4.71 |
| 19.36 ± 0.2 | 4.59 |
| 20.44 ± 0.2 | 4.35 |
| 21.32 ± 0.2 | 4.17 |
| 22.02 ± 0.2 | 4.04 |
| 22.99 ± 0.2 | 3.87 |
| 24.18 ± 0.2 | 3.68 |
| 25.22 ± 0.2 | 3.53 |
| 25.68 ± 0.2 | 3.47 |

Therefore, a further aspect of the present invention relates to a crystalline form A of 2-[4-(4-chlorophenoxy)-2-(trifluoromethyl)phenyl]-3-methyl-1-(1,2,4-triazol-1-yl)butane-2-ol, as described above.

The crystal form A of compound I.5 according to the invention is easier to handle than the previously known forms of compound I.5 (known e.g. from PCT/EP2012/063626), since during production form A is obtained in the form of discrete crystals or crystallites having increased particle size in comparison to other forms of compound I.5. Increased particle size and the compact habit of form A facilitates filtration from mother liquour and allows easier drying of the solid material.

Compared to the known forms of compound I.5, pure form A is likely to display increased stability with regard to conversion into another modification. The stability of formulations which contain the compound I.5 in form A is likely higher than the stability of formulations which contain mixtures of different modifications of compound I.3. The terms "pure form A" should be understood to mean that the proportion of the modification in question, based on the total quantity of compound I.5, is at least 80% by weight in particular at least 90% by weight and especially at least 95% by weight. Accordingly, a further object of the present invention relates a composition of the compound I.3 which at least 80% by weight, in particular at least 90% by weight or at least 95% by weight consists of the crystalline form A, based on the total amount of the compound I.5, contained in the composition.

Furthermore, form A of compound I.5 may be distinguished from the known forms of compound I.5 by differences in one or more of the following properties: solubility, vapor pressure, dissolution rate, stability against a phase change into a different modification, stability during grinding, suspension stability, optical and mechanical properties, hygroscopicity, crystal form and size, filterability, density, melting point, stability to decomposition, color and even chemical reactivity or biological activity.

Studies on single crystals of form A demonstrate that the underlying crystal structure is monoclinic. The unit cell has the space group $P2_1/n$. The characteristic data of the crystal structure of form A (determined at 100 K, Cu—$K_\alpha$ radiation) are compiled in the following table 4.

TABLE 4

Crystallographic characteristics of form A of compound 1.5

| Parameter | Form A |
|---|---|
| class | Monoclinic |
| space group | $P2_1/n$ |
| a | 8.0285(2) Å |
| b | 27.8467(6) Å |
| c | 9.1925(2) Å |
| α | 90° |
| β | 103.3169(10)° |
| γ | 90° |
| volume | 1991.32(8) Å³ |
| Z | 4 |
| R factor | 2.80% | a, b, c = unit cell length
α, β, γ = unit cell angle
Z = number of molecules in the unit cell Form A of compound I.5 displays a thermogram with a characteristic melting peak in the range from 109 to 116° C. The melting point, determined as the onset of the melting peak, typically lies in the range from about 114° C. to 115° C. The values quoted here relate to values determined by differential calorimetry (differential scanning calorimetry: DSC, crimped but vented aluminium pans, heating rate 10 K/min, vented with nitrogen 150 ml/min).

Form A of compound I.5 was prepared by example C.3 as described hereinafter, followed by crystallization from a solution of compound I.5 in lower alkanol, such as methanol. Preferably, crystallization is achieved by cooling a hot solution of compound I.5 in the alkanol. Preferably, the hot solution has a temperature of at least 50°, e.g. from 50 to 70° C. Preferably cooling is performed with controlled cooling rate, the cooling rate being in particular from 1 to 20 k/h, in particular from 2 to 10 k/h. Single crystals of form A of compound I.5 were obtained by diffusion of heptane into a solution of compound I.5 in 2-propanol.

The crystallization of form A can be promoted or accelerated by seeding with seed crystals of form A of compound I.5, for example by adding seed crystals of form A before or during the crystallization. If seed crystals are added during the crystallization, the quantity thereof is typically 0.001 to 10 wt. %, often 0.005 to 5 wt. %, in particular 0.01 to 1 wt. % and especially 0.05 to 0.5 wt. %, based on the total amount of compound I.5 to be crystallized.

Just like the known forms of compounds I.3 and I.5, forms A of compounds I.3 and I.5, respectively are suitable as fungicides, i.e. for controlling harmful fungi, in particular for controlling plant pathogenic fungi. However they are superior to these as regards its handling and formulation properties. Hence, the invention relates to the use of forms A and B of compounds I.3 and I.5, respectively for controlling harmful fungi, in particular for controlling plant pathogenic fungi.

The invention thus also relates to agrochemical compositions containing the crystalline form A of compound I.3 or the crystalline form A of compound I.5, and also one or more auxiliaries, conventionally used for the formulation of plant protection agents, in particular plant protection agents in the form of aqueous suspension concentrates (so-called SC's) or non-aqueous suspension concentrates (so-called OD's), and plant protection agents in the form of powders (so-called WP's) and granules (so-called WG's) dispersible in water.

The invention also relates to a method for controlling harmful fungi, in particular for controlling plant pathogenic fungi, which method comprises treating the fungi or the plants, the soil, seeds or non-living materials with the crystalline form A of compound I.3 or with the crystalline form A of compound I.5, preferably as a suitable active substance preparation, is used on plants, their habitat and/or on seeds.

The crystalline form A of compound I.3 as well as the crystalline form A of compound I.5 and the agrochemical compositions which contain the crystalline form A of compound I.3 or the crystalline form A of compound I.5 may be used for combating a broad spectrum of phytopathogenic fungi, including soil-borne fungi, which derive especially from the classes of the Plasmodiophoromycetes, Peronosporomycetes (syn. Oomycetes), Chytridiomycetes, Zygomycetes, Ascomycetes, Basidiomycetes and Deuteromycetes (syn. Fungi imperfecti). Some are systemically effective and they can be used in crop protection as foliar fungicides, fungicides for seed dressing and soil fungicides. Moreover, they are suitable for controlling harmful fungi, which inter alia occur in wood or roots of plants.

The crystalline form A of compound I.3 as well as the crystalline form A of compound I.5 and the agrochemical compositions which contain the crystalline form A of compound I.3 or the crystalline form A of compound I.5 are particularly important in the control of a multitude of phytopathogenic fungi on various cultivated plants, such as cereals, e. g. wheat, rye, barley, triticale, oats or rice; beet, e. g. sugar beet or fodder beet; fruits, such as pomes, stone fruits or soft fruits, e. g. apples, pears, plums, peaches, almonds, cherries, strawberries, raspberries, blackberries or gooseberries; leguminous plants, such as lentils, peas, alfalfa or soybeans; oil plants, such as rape, mustard, olives, sunflowers, coconut, cocoa beans, castor oil plants, oil palms, ground nuts or soybeans; cucurbits, such as squashes, cucumber or melons; fiber plants, such as cotton, flax, hemp or jute; citrus fruit, such as oranges, lemons, grapefruits or mandarins; vegetables, such as spinach, lettuce, asparagus, cabbages, carrots, onions, tomatoes, potatoes, cucurbits or paprika; lauraceous plants, such as avocados, cinnamon or camphor; energy and raw material plants, such as corn, soybean, rape, sugar cane or oil palm; corn; tobacco; nuts; coffee; tea; bananas; vines (table grapes and grape juice grape vines); hop; turf; sweet leaf (also called *Stevia*); natural rubber plants or ornamental and forestry plants, such as flowers, shrubs, broad-leaved trees or evergreens, e. g. conifers; and on the plant propagation material, such as seeds, and the crop material of these plants.

The crystalline form A of compound I.3 as well as the crystalline form A of compound I.5 and the agrochemical compositions which contain the crystalline form A of compound I.3 or the crystalline form A of compound I.5 may also be used for protecting plant propagation material against infection with phytopathogenic fungi. The term "plant propagation material" is to be understood to denote all the generative parts of the plant such as seeds and vegetative plant material such as cuttings and tubers (e. g. potatoes), which can be used for the multiplication of the plant. This includes seeds, roots, fruits, tubers, bulbs, rhizomes, shoots, sprouts and other parts of plants, including seedlings and young plants, which are to be transplanted after germination or after emergence from soil. These young plants may also be protected before transplantation by a total or partial treatment by immersion or pouring.

The crystalline form A of compound I.3 as well as the crystalline form A of compound I.5 and the agrochemical compositions which contain the crystalline form A of compound I.3 or the crystalline form A of compound I.5 may also be used for controlling harmful fungi in the protection of stored products or harvest and in the protection of materials. The term "protection of materials" is to be understood to denote the protection of technical and non-living materials, such as adhesives, glues, wood, paper and paperboard, textiles, leather, paint dispersions, plastics, coiling lubricants, fiber or fabrics, against the infestation and destruction by harmful microorganisms, such as fungi and bacteria. As to the protection of wood and other materials.

Further, crystalline form A of compound I.3 as well as the crystalline form A of compound I.5 and the agrochemical compositions which contain the crystalline form A of compound I.3 or the crystalline form A of compound I.5 can also be used in crops which through breeding including genetic engineering methods are tolerant towards insect or fungal attack. Plants that have been modified by breeding, mutagenesis or genetic engineering, e. g. have been rendered tolerant to applications of specific classes of herbicides, such as auxin herbicides such as dicamba or 2,4-D; bleacher herbicides such as hydroxylphenylpyruvate dioxygenase (HPPD) inhibitors or phytoene desaturase (PDS) inhibittors; acetolactate synthase (ALS) inhibitors such as sulfonyl ureas or imidazolinones; enolpyruvylshikimate-3-phosphate synthase (EPSPS) inhibitors, such as glyphosate; glutamine synthetase (GS) inhibitors such as glufosinate; protoporphyrinogen-IX oxidase inhibitors; lipid biosynthesis inhibitors such as acetyl CoA carboxylase (ACCase) inhibitors; or oxynil (i. e. bromoxynil or ioxynil) herbicides as a result of conventional methods of breeding or genetic engineering. Furthermore, plants have been made resistant to multiple classes of herbicides through multiple genetic modifications, such as resistance to both glyphosate and glufosinate or to both glyphosate and a herbicide from another class such as ALS inhibitors, HPPD inhibitors, auxin herbicides, or ACCase inhibitors. These herbicide resistance technologies are e. g. described in Pest Managem. Sci. 61, 2005, 246; 61, 2005, 258; 61, 2005, 277; 61, 2005, 269; 61, 2005, 286; 64, 2008, 326; 64, 2008, 332; Weed Sci. 57, 2009, 108; Austral. J. Agricult. Res. 58, 2007, 708; Science 316, 2007, 1185; and references quoted therein. Several cultivated plants have been rendered tolerant to herbicides by conventional methods of breeding (mutagenesis), e. g. Clearfield® summer rape (Canola, BASF SE, Germany) being tolerant to imidazolinones, e. g. imazamox, or ExpressSun® sunflowers (DuPont, USA) being tolerant to sulfonyl ureas, e. g. tribenuron. Genetic engineering methods have been used to render cultivated plants such as soybean, cotton, corn, beets and rape, tolerant to herbicides such as glyphosate and glufosinate, some of which are commercially available under the trade names RoundupReady® (glyphosate-tolerant, Monsanto, U.S.A.), Cultivance® (imidazolinone tolerant, BASF SE, Germany) and LibertyLink® (glufosinate-tolerant, Bayer CropScience, Germany).

Form A of compound I.3 or with form A of compound I.5 and compositions thereof, respectively, may be used for improving the health of a plant. The invention also relates to a method for improving plant health by treating a plant, its propagation material and/or the locus where the plant is growing or is to grow with an effective amount of compounds I and compositions thereof, respectively. The term "plant health" is to be understood to denote a condition of the plant and/or its products which is determined by several indicators alone or in combination with each other such as yield (e. g. increased biomass and/or increased content of valuable ingredients), plant vigor (e. g. improved plant growth and/or greener leaves ("greening effect")), quality (e. g. improved content or composition of certain ingredients) and tolerance to abiotic and/or biotic stress. The above identified indicators for the health condition of a plant may be interdependent or may result from each other.

Form A of compound I.3 or form A of compound I.5 are employed as such or in form of compositions by treating the fungi or the plants, plant propagation materials, such as seeds, soil, surfaces, materials or rooms to be protected from fungal attack with a fungicidally effective amount of the active substances. The application can be carried out both before and after the infection of the plants, plant propagation materials, such as seeds, soil, surfaces, materials or rooms by the fungi. Plant propagation materials may be treated with form A of compound I.3 or with form A of compound I.5 as such or a composition comprising form A of compound I.3 or form A of compound I.5 prophylactically either at or before planting or transplanting.

The crystalline form A of compound I.3 as well as the crystalline form A of compound I.5 and the agrochemical compositions which contain the crystalline forms A of compounds I.3 or I.5, respectively, can, for example, be used in the form of directly sprayable aqueous solutions, powders, suspensions and also high concentration aqueous, oily or other suspensions, oil suspensions, pastes, dusting agents, scattering agents or granules by spraying, misting, dusting, scattering or pouring. The use forms are determined by the use purposes; in each case, they should ensure the finest possible distribution of the active substances according to the invention.

The invention also relates to agrochemical compositions comprising an auxiliary and forms A of compounds I.3 or I.5 according to the invention.

The agrochemical compositions according to the invention contain either form A of compound I.3 or form A of compound I.5. The purity, based on the modification in question, is preferably at least 80 wt. %, in particular at least 90% or at least 95%, based on the total amount of compound I.3 or I.5, respectively. However, the purity, based on the modification in question, may also be as low as 5% or at least 10%, based on the total amount of compound I.3 or I.5, respectively.

The agrochemical compositions according to the invention also contain one or more auxiliaries, which are usual for the formulation of plant protection agents. In such agrochemical compositions, the quantity of active substance, i.e. the total quantity of compounds I.3 or I.5 and of other active substances, if present, normally lies in the range from 1 to 98 wt. %, in particular in the range from 5 to 95 wt. %, based on the total weight of the agrochemical compositions, the remainder being one or more auxiliaries.

Suitable auxiliaries are liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

All solid and liquid substances which are normally used as carriers in plant protection agents, in particular in herbicide formulations are possible as carriers.

Solid carriers are for example mineral earths such as silicic acids, silica gels, silicates, talc, kaolin, limestone, lime, chalk, bole, loess, clay, dolomite, diatomaceous earth, calcium and magnesium sulfate, magnesium oxide, ground plastics, fertilizers such as ammonium sulfate, ammonium phosphate, ammonium nitrate, ureas and plant products such as cereal flour, tree bark, wood and nutshell flour, cellulose powder and other solid carriers.

Liquid carriers, as well as water, are also organic liquids, for example mineral oil fractions of medium to high boiling point such as kerosene and diesel oil, also coal tar oils and oils of plant or animal origin, aliphatic, cyclic and aromatic hydrocarbons, for example paraffins, tetrahydronaphthalene, alkylated naphthalenes and derivatives thereof, alkylated benzenes and derivatives thereof, including aromatic and non-aromatic hydrocarbon mixtures, for example the products marketed under the trade names Exxsol and Solvesso, alcohols such as propanol, butanol and cyclohexanol.

Typical further auxiliaries include surface-active substances, in particular those wetting agents, emulsifiers and dispersant (additives) normally used in plant protection agents, and also viscosity-modifying additives (thickeners and rheology modifiers), antifoaming agents, antifreeze agents, pH adjusting agents, stabilizers, anticaking agents and biocides (preservatives).

Possible surface-active substances are preferably anionic and nonionic surfactants. Protective colloids are also suitable surface-active substances.

The quantity of surface-active substances will as a rule be 0.1 to 50 wt. %, in particular 0.5 to 30 wt. %, based on the total weight of the plant protection agents according to the invention, or 0.5 to 100 wt. %, based on the total quantity of solid active substances in the formulation. Preferably, the surface-active substance include at least one anionic surface-active substance and at least one nonionic surface-active substance, and the proportion of anionic to nonionic surface-active substance typically lies in the range from 10:1 to 1:10.

Surface-active compounds, also termed surfactants may be anionic, cationic, nonionic and amphoteric surfactants, block polymers, polyelectrolytes, and mixtures thereof. Such surfactants can be used as emulsifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Examples of anionic surfactants include alkyl aryl-sulfonates, aromatic sulfonates, for example ligninsulfonates (Borresperse types, Borregaard), phenylsulfonates, naphthalenesulfonates (Morwet types, Akzo Nobel), dibutylnaphthalenesulfonates (Nekal types, BASF), alkyl sulfates, in particular fatty alcohol sulfates, lauryl sulfates, and sulfated hexadeca-, heptadeca- and octadecanols, alkylsulfonates, alkyl ether sulfates, in particular fatty alcohol (poly)glycol ether sulfates, alkyl aryl ether sulfates, alkyl polyglycol ether phosphates, polyarylphenyl ether phosphates, alkyl-sulfosuccinates, olefin sulfonates, paraffin sulfon-ates, petroleum sulfonates, taurides, sarcosides, fatty acids, alkylnaphthalenesulfonic acids, naphthalene-sulfonic acids, ligninsulfonic acids, condensation products of sulfonated naphthalenes with formaldehyde, condensation products of sulfonated naphthalenes with formaldehyde and phenol and optionally urea and condensation products of phenolsulfonic acid with formaldehyde and urea, lignin sulfite waste liquor, alkyl phosphates, alkyl aryl phosphates, for example tristyryl phosphates, and polycarboxylates such as for example polyacrylates, maleic anhydride/olefin copolymers (for example Sokalan® CP9, BASF), including the alkali metal, alkaline earth, ammonium and amine salts of the aforesaid substances. Preferred anionic surface-active substances are those which bear at least one sulfonate group and in particular the alkali metal and ammonium salts thereof.

Examples of non-ionic surface-active substances are alkylphenol alkoxylates, in particular ethoxylates and ethoxylate-copropoxylates of octylphenol, isooctylphenol, nonylphenol and tributylphenol, di- and tristyrylphenol alkoxylates, alcohol alkoxylates, in particular fatty alcohol ethoxylates and fatty alcohol ethoxylate-copropoxylates, for example alkoxylated isotridecanol, fatty amine alkoxylates, polyoxyethylene glycerol fatty acid esters, castor oil alkoxylates, fatty acid alkoxylates, fatty acid amide alkoxylates, fatty acid polydiethanolamides, lanolin ethoxylates, fatty acid polyglycol esters, isotridecyl alcohol, ethoxylated fatty acid amides, ethoxylated fatty acid esters, alkyl polyglycosides, ethoxylated alkyl polyglycosides, sorbitan fatty acid esters, ethoxylated sorbitan fatty acid esters, glycerol fatty acid esters, lower molecular weight polyalkylene oxides such as polyethylene glycol, polypropylene oxide, polyethylene oxide co-propylene oxide di- and tri-block copolymers, and mixtures thereof. Preferred nonionic surface-active substances are fatty alcohol ethoxylates, alkyl polyglycosides, glycerol fatty acid esters, castor oil ethoxylates, fatty acid ethoxylates, fatty acid amide ethoxylates, lanolin ethoxylates, fatty acid polyglycol esters, ethylene oxide propylene oxide block copolymers and mixtures thereof.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B—C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Protective colloids are typically water-soluble, amphiphilic polymers which unlike the aforesaid surfactants typically have molecular weights over 2,000 daltons (number average). Examples thereof are proteins and denatured proteins such as casein, polysaccharides such as water-soluble starch derivatives and cellulose derivatives, hydrophobically modified starches and celluloses, for example methylcellulose, and also polycarboxylates such as polyacrylic acid, acrylic acid copolymers and maleic acid copolymers (BASF Sokalan types), polyvinyl alcohol (Mowiol types from Clariant), polyalkoxylates, polyvinylpyrrolidone, vinylpyrrolidone copolymers, polyvinyl amines, polyethyleneimines (Lupasol types from BASF) and higher molecular weight polyalkylene oxides such as polyethylene glycol, polypropylene oxides, and polyethylene oxide copolypropylene oxide di- and tri-block copolymers.

The agrochemical compositions according to the invention can also contain one or more additives modifying the viscosity (rheology modifiers). These are understood in particular to mean substances and substance mixtures which impart modified flow behavior to the formulation, for example a high viscosity in the resting state and low viscosity in the moving state. The nature of the rheology modifier is determined by the nature of the formulation. As examples of rheology modifiers, inorganic substances, for example layer silicates and organically modified layer silicates such as bentonites or attapulgites (for example Attaclay®, Engelhardt Co.), and organic substances such as polysaccharides and heteropolysaccharides such as Xanthan Gum® (Kelzan® from Kelco Co.), Rhodopol® 23 (Rhone Poulenc) or Veegum® (R.T. Vanderbilt Co.) should be mentioned. The quantity of the viscosity-modifying additives is often 0.1 to 5 wt. %, based on the total weight of the plant protection agent.

Examples of antifoaming agents are the silicone emulsions known for this purpose (Silikon® SRE, Wacker Co. or Rhodorsil® from Rhodia Co.), long-chain alcohols, fatty acids and salts thereof, foam suppressants of the aqueous wax dispersion type, solid foam suppressants (so-called Compounds) and organofluorine compounds and mixtures thereof. The quantity of anti-foaming agent is typically 0.1 to 1 wt. %, based on the total weight of the plant protection agent.

The agrochemical compositions according to the invention may also contain preservatives for stabilization. Suitable preservatives are those based on isothiazol-ones, for example Proxel® from ICI Co., or Acticide® from Thor Chemie Co. or Kathon® MK from Rohm & Hass Co. The quantity of preservative is typically 0.05 to 0.5 wt. %, based on the total weight of the SC.

Aqueous agrochemical compositions, i.e. those with an aqueous carrier, often contain antifreeze agents. Suitable antifreeze agents are liquid polyols, for example ethylene glycol, propylene glycol or glycerine, and urea. The quantity of antifreeze agent is as a rule 1 to 20 wt. %, in particular 5 to 10 wt. %, based on the total weight of the aqueous plant protection agent.

If the agrochemical composition, which contain the crystalline forms A of compounds I.3 or I.5, respectively, are used for seed treatment, they can also contain normal components such as are used for seed treatment, for example in dressing or coating. In addition to the aforesaid components, these include in particular colorants, adhesives, fillers and plasticizers.

All the dyes and pigments usual for such purposes are possible as colorants. Both pigments of low solubility in water and also dyes soluble in water are usable here. As examples, the dyes and pigments known under the names Rhodamin B, C.I. Pigment Red 112 and C.I. Solvent Red 1, Pigment Blue 15:4, Pigment Blue 15:3, Pigment Blue 15:2, Pigment Blue 15:1, Pigment Blue 80, Pigment Yellow 1, Pigment Yellow 13, Pigment Red 48:2, Pigment Red 48:1, Pigment Red 57:1, Pigment Red 53:1, Pigment Orange 43, Pigment Orange 34, Pigment Orange 5, Pigment Green 36, Pigment Green 7, Pigment White 6, Pigment Brown 25, Basic Violet 10, Basic Violet 49, Acid Red 51, Acid Red 52, Acid Red 14, Acid Blue 9, Acid Yellow 23, Basic Red 10, Basic Red 10 and Basic Red 108 may be mentioned. The quantity of colorant will normally not constitute more than 20 wt. % of the formulation and preferably lies in the range from 0.1 to 15 wt. %, based on the total weight of the agrochemical composition.

All binders normally usable in dressings come under consideration as adhesives. Examples of suitable binders include thermoplastic polymers such as poly-vinylpyrrolidone, polyvinyl acetate, polyvinyl alcohol and tylose and also polyacrylates, polymethacrylates, polybutenes, polyisobutenes, polystyrene, polyethylene amines, polyethylene amides, the aforesaid protective colloids, polyesters, polyether esters, polyanhydrides, polyester urethanes, polyester amides, thermoplastic polysaccharides, for example cellulose derivatives such as cellulose esters, cellulose ethers, cellulose ether esters, including methylcellulose, ethylcellulose, hydroxymethylcellulose, carboxymethylcellulose, hydroxypropyl cellulose and starch derivatives and modified starches, dextrins, maltodextrins, alginates and chitosans, and also fats, oils, proteins, including casein, gelatin and zein, gum Arabic and shellac. The adhesives are preferably plant-compatible, i.e. they exhibit no, or no significant, phytotoxic effects. The adhesives are preferably biodegradable. The adhesive is preferably selected such that it acts as a matrix for the active components of the formulation. The quantity of adhesive will normally not constitute more than 40 wt. % of the formulation and preferably lies in the range from 1 to 40 wt. % and in particular in the range from 5 to 30 wt. %, based on the total weight of the agrochemical composition.

In addition to the adhesive, the agrochemical composition for seed treatment can also contain inert fillers. Examples of these are the aforesaid solid carriers, in particular finely divided inorganic materials such as clays, chalk, bentonite, kaolin, talc, perlite, mica, silica gel, diatomaceous earth, quartz powder and montmorillonite but also fine-particle organic materials such as wood flour, cereal flour, active charcoal and the like. The quantity of filler is preferably selected such that the total quantity of filler does not exceed 70 wt. %, based on the total weight of all non-volatile components of the formulation. Often, the quantity of filler lies in the range from 1 to 50 wt. %, based on the total weight of all non-volatile components of the agrochemical composition.

In addition, the agrochemical composition for seed treatment can also contain a plasticizer which increases the flexibility of the coating. Examples of plasticizers are oligomeric polyalkylene glycols, glycerine, dialkyl phthalates, alkylbenzyl phthalates, glycol benzoates and comparable compounds. The quantity of plasticizer in the coating often lies in the range from 0.1 to 20 wt. %, based on the total weight of all non-volatile components of the agrochemical composition.

A preferred embodiment of the invention relates to liquid formulations of the forms A of compounds I.3 or I.5, respecitvely. In addition to the solid active substance phase, these have at least one liquid phase, in which form A of compound I.3 and form A of compound I.5, respectively, are present in the form of dispersed particles. Possible liquid phases are essentially water and those organic solvents in which the forms A of compounds I.3 or I.5, respectively, are only slightly soluble, or insoluble, for example those wherein the solubilities of forms A of compounds I.3 or I.5, respectively, at 25° C. and 1013 mbar are not more than 1 wt. %, in particular not more than 0.1 wt. %, and especially not more than 0.01 wt. %.

According to a first preferred embodiment, the liquid phase is selected from water and aqueous solvents, i.e. solvent mixtures which in addition to water also contain up to 20 wt. %, preferably however not more than 10 wt. %, based on the total quantity of water and solvent, of one or more organic solvents miscible with water, for example ethers miscible with water such as tetrahydrofuran, methyl glycol, methyl diglycol, alkanols such as isopropanol or polyols such as glycol, glycerine, diethylene glycol, propylene glycol and the like. Such formulations are also referred to below as suspension concentrates (SCs).

Such suspension concentrates contain compound I.3 as form A or compound I.5 as form A in a particulate form, wherein the particles of the forms A are present suspended in an aqueous phase. The size of the active substance particles, i.e. the size which 90 wt. % of the active substance particles do not exceed, here typically lies below 30 µm, in particular below 20 µm. Advantageously, in the SCs according to the invention, at least 40 wt. % and in particular at least 60 wt. % of the particles have diameters below 2 µm.

In such SCs the quantity of active substance, i.e. the total quantity of tembotrione and of other active substances if necessary, usually lies in the range from 5 to 70 wt. %, in particular in the range from 10 to 50 wt. %, based on the total weight of the suspension concentrate.

In addition to the active substance, aqueous suspension concentrates typically contain surface-active substances, and also if necessary antifoaming agents, thickeners (=rheology modifiers), antifreeze agents, stabilizers (biocides), agents for adjusting the pH and anticaking agents.

Possible surface-active substances are the previously named surface-active substances. Preferably the aqueous plant protection agents according to the invention contain at least one of the previously named anionic surfactants and if necessary one or more nonionic surfactants, if necessary in combination with a protective colloid. The quantity of surface-active substances will as a rule be 1 to 50 wt. %, in particular 2 to 30 wt. %, based on the total weight of the aqueous SCs according to the invention. Preferably the surface-active substances include at least one anionic surface-active substance and at least one nonionic surface-active substance, and the proportion of anionic to nonionic surface-active substance typically lies in the range from 10:1 to 1:10.

Concerning the nature and quantity of the antifoaming agents, thickeners, antifreeze agents and biocides, the same applies as aforesaid.

If necessary, the aqueous SCs according to the invention can contain buffers for pH regulation. Examples of buffers are alkali metal salts of weak inorganic or organic acids, such as for example phosphoric acid, boric acid, acetic acid, propionic acid, citric acid, fumaric acid, tartaric acid, oxalic acid and succinic acid.

According to a second preferred embodiment, the liquid phase consists of non-aqueous organic solvents in which the solubility of form A of compound I.3 and of form A of compound I.5, respectively, at 25° C. and 1013 mbar is not more than 1 wt. %, in particular not more than 0.1 wt. %, and especially not more than 0.01 wt. %. These include in particular aliphatic and cycloaliphatic hydrocarbons and oils, in particular those of plant origin, and also $C_1$-$C_4$ alkyl esters of saturated or unsaturated fatty acids or fatty acid mixtures, in particular the methyl esters, for example methyl oleate, methyl stearate and rape oil methyl ester, but also paraffinic mineral oils and the like. Accordingly, the present invention relates also to agents for plant protection in the form of a non-aqueous suspension concentrate, which will also be referred to below as OD (oildispersion). Such ODs contain the forms A of compounds I.3 or I.5, respectively, in particulate form, wherein the particles of forms A of compounds I.3 or I.5, respectively, are present suspended in a non-aqueous phase. The size of the active substance particles, i.e. the size which 90 wt. % of the active substance particles do not exceed, here typically lies below 30 µm, in particular below 20 µm. Advantageously, in the non-aqueous suspension concentrates, at least 40 wt. % and in particular at least 60 wt. % of the particles have diameters below 2 µm.

In such ODs, the quantity of active substance, i.e. the total quantity of compound I.3 or I.5 and of other active substances if necessary, usually lies in the range from 10 to 70 wt. %, in particular in the range from 20 to 50 wt. %, based on the total weight of the non-aqueous suspension concentrate.

In addition to the active substance and the liquid carrier, non-aqueous suspension concentrates typically contain surface-active substances, and also if necessary antifoaming agents, agents to modify the rheology and stabilizers (biocides).

Possible surface-active substances are preferably the previously named anionic and nonionic surfactants. The quantity of surface-active substances will as a rule be 1 to 30 wt. %, in particular 2 to 20 wt. %, based on the total weight of the non-aqueous SCs according to the invention. Preferably the surface-active substances include at least one anionic surface-active substance and at least one nonionic surface-active substance, and the proportion of anionic to nonionic surface-active substance typically lies in the range from 10:1 to 1:10.

Forms A of compounds I.3 or I.5, respectively, can also be formulated as solid plant protection agents. These include powder, scattering and dusting agents but also water-dispersible powders and granules, for example coated, impregnated and homogenous granules. Such formulations can be produced by mixing or simultaneous grinding of either form A of compound I.3 or form A of compound I.5, respectively, with a solid carrier and if necessary other additives, in particular surface-active substances. Granules can be produced by binding of the active substances to solid carriers. Solid carriers are mineral earths such as silicic acids, silica gels, silicates, talc, kaolin, limestone, lime, chalk, bole, loess, clay, dolomite, diatomaceous earth, calcium and magnesium sulfate, magnesium oxide, ground plastics, fertilizers such as ammonium sulfate, ammonium phosphate, ammonium nitrate, ureas and plant products such as cereal flour, tree bark, wood and nutshell flour, cellulose powder or other solid carriers. Solid formulations can also be produced by spray drying, if necessary in the presence of polymeric or inorganic drying aids, and if necessary in the presence of solid carriers. For the production of solid formulations of forms A of compounds I.3 or I.5, respectively, extrusion processes, fluidized bed granulation, spray granulation and comparable technologies are suitable.

Possible surface-active substances are the previously named surfactants and protective colloids. The quantity of surface-active substances will as a rule be 1 to 30 wt. %, in particular 2 to 20 wt. %, based on the total weight of the solid formulation according to the invention.

In such solid formulations, the quantity of active substance, i.e. the total quantity of tembotrione and of other active substances if necessary, usually lies in the range from 10 to 70 wt. %, in particular in the range from 20 to 50 wt. %, based on the total weight of the solid formulation.

The following formulation examples illustrate the production of such preparations:

I. Water-dispersible powder:
   20 parts by weight of forms A of compounds I.3 or I.5, respectively, are mixed well with 3 parts by weight of the sodium salt of diisobutylnaphthalenesulfonic acid, 17 parts by weight of the sodium salt of a ligninsulfonic acid from a sulfite waste liquor and 60 parts by weight of powdered silica gel and ground in a hammer mill. In this manner, a water-dispersible powder which contains the respective form A is obtained.

II. Dusting agent
   5 parts by weight of the forms A of compounds I.3 or I.5, respectively, are mixed with 95 parts by weight of finely divided kaolin. In this manner, a dusting agent which contains 5 wt. % of the respective form A is obtained.

III. Non-aqueous suspension concentrate:
   20 parts by weight of forms A of compounds I.3 or I.5, respectively, are mixed intimately with 2 parts by weight of the calcium salt of dodecylbenzenesulfonic acid, 8 parts by weight of fatty alcohol polyglycol ether, 2 parts by weight of the sodium salt of a phenolsulfonic acid urea formaldehyde condensate and 68 parts by weight of a paraffinic mineral oil. A stable, non-aqueous suspension concentrate of the respective form A is obtained.

IV. Non-aqueous suspension concentrate:
   20 parts by weight of forms A of compounds I.3 or I.5, respectively, are ground to a fine active substance suspension in an agitator ball mill with the addition of 10 parts by weight of dispersants and wetting agents and 70 parts by weight of a paraffinic mineral oil. A stable, non-aqueous suspension concentrate of the respective form A is obtained. On dilution in water, a stable suspension of the respective form A is obtained. The active substance content in the formulation is 20 wt. %.

V. Aqueous suspension concentrate:
   10 parts by weight of forms A of compounds I.3 or I.5, respectively, are formulated as an aqueous suspension concentrate in a solution of 17 parts by weight of a poly(ethylene glycol)(propylene glycol) block copolymer, 2 parts by weight of a phenolsulfonic acid formaldehyde condensate and about 1 part by weight of other additives (thickeners, foam suppressants) in a mixture of 7 parts by weight of propylene glycol and 63 parts by weight of water.

VI. Aqueous suspension concentrate:
   20 parts by weight of forms A of compounds I.3 or I.5, respectively, are ground to a fine active substance suspension in a stirred ball mill with the addition of 10 parts by weight of dispersants and wetting agents and 70 parts by weight of water. On dilution in water, a stable suspension of the respective form A is obtained. The active substance content in the formulation is 20 wt. %.

VII. Water-dispersible and water-soluble granules
   50 parts by weight of forms A of compounds I.3 or I.5, respectively, are finely ground with the addition of 50 parts by weight of dispersants and wetting agents and formulated as water-dispersible or water-soluble granules by means of industrial devices (for example extrusion, spray tower, fluidized bed). On dilution in water, a stable dispersion or solution of the respective form A is obtained. The formulation has an active substance content of 50 wt. %.

VIII. Water-dispersible and water-soluble powder
   75 parts by weight of forms A of compounds I.3 or I.5, respectively, are ground in a rotorstator mill with the addition of 25 parts by weight of dispersants and wetting agents and also silica gel. On dilution in water, a stable dispersion or solution of the respective form A is obtained. The active substance content of the formulation is 75 wt. %.

IX. Gel formulations:
   20 parts by weight of forms A of compounds I.3 or I.5, respectively, 10 parts by weight of dispersant, 1 part by weight of gelling agent and 70 parts by weight of water or an organic solvent are ground to a fine suspension in a ball mill. On dilution in water, a stable suspension of the respective form A is obtained. The active substance content of the formulation is 20 wt. %.

X. Directly usable granules (GR, FG, GG, MG)
   0.5 parts by weight of the forms A of compounds I.3 or I.5, respectively, are finely ground and combined with 99.5 parts by weight of carriers. Common processes here are extrusion, spray drying or fluidized bed. Granules for direct application with 0.5 wt. % active substance content are thus obtained.

The application of forms A of compounds I.3 or I.5, respectively, or the agrochemical composition containing them is effected, if the formulation is not already ready for use, in the form of aqueous spray fluids. These are prepared by dilution of the aforesaid compositions containing forms A of compounds I.3 or I.5, respectively, with water. The spray fluids can also contain other components in dissolved, emulsified or suspended form, for example fertilizers, active substances of other herbicidal or growth-regulating active substance groups, other active substances, for example active substances for combating animal pests or phytopathogenic fungi or bacteria, and also mineral salts which are used for the elimination of nutritional and trace element deficiencies, and non-phytotoxic oils and oil concentrates. As a rule, these components are added to the spray fluid before, during or after the dilution of the formulations according to the invention. The user applies the composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

When employed in plant protection, the amounts of compounds I.3 or I.5 applied are, depending on the kind of effect desired, from 0.001 to 2 kg per ha, preferably from 0.005 to 2 kg per ha, more preferably from 0.05 to 0.9 kg per ha, and in particular from 0.1 to 0.75 kg per ha.

In treatment of plant propagation materials such as seeds, e. g. by dusting, coating or drenching seed, amounts of compounds I.3 or I.5 of from 0.1 to 1000 g, preferably from 1 to 1000 g, more preferably from 1 to 100 g and most preferably from 5 to 100 g, per 100 kilogram of plant propagation material (preferably seeds) are generally required.

When used in the protection of materials or stored products, the amounts of compounds I.3 or I.5 applied depends on the kind of application area and on the desired effect. Amounts customarily applied in the protection of materials are 0.001 g to 2 kg, preferably 0.005 g to 1 kg, of active substance per cubic meter of treated material.

Various types of oils, wetters, adjuvants, fertilizer, or micronutrients, and further pesticides (e.g. herbicides, insecticides, fungicides, growth regulators, safeners, biopesticides) may be added to the active substances or the compositions comprising them as premix or, if appropriate not until immediately prior to use (tank mix). These agents can be admixed with the compositions according to the invention in a weight ratio of 1:100 to 100:1, preferably 1:10 to 10:1.

EXAMPLES AND FIGURES

The following figures and examples further illustrate the present invention and do not restrict the invention in any manner.

ANALYTICS

Figure 1:
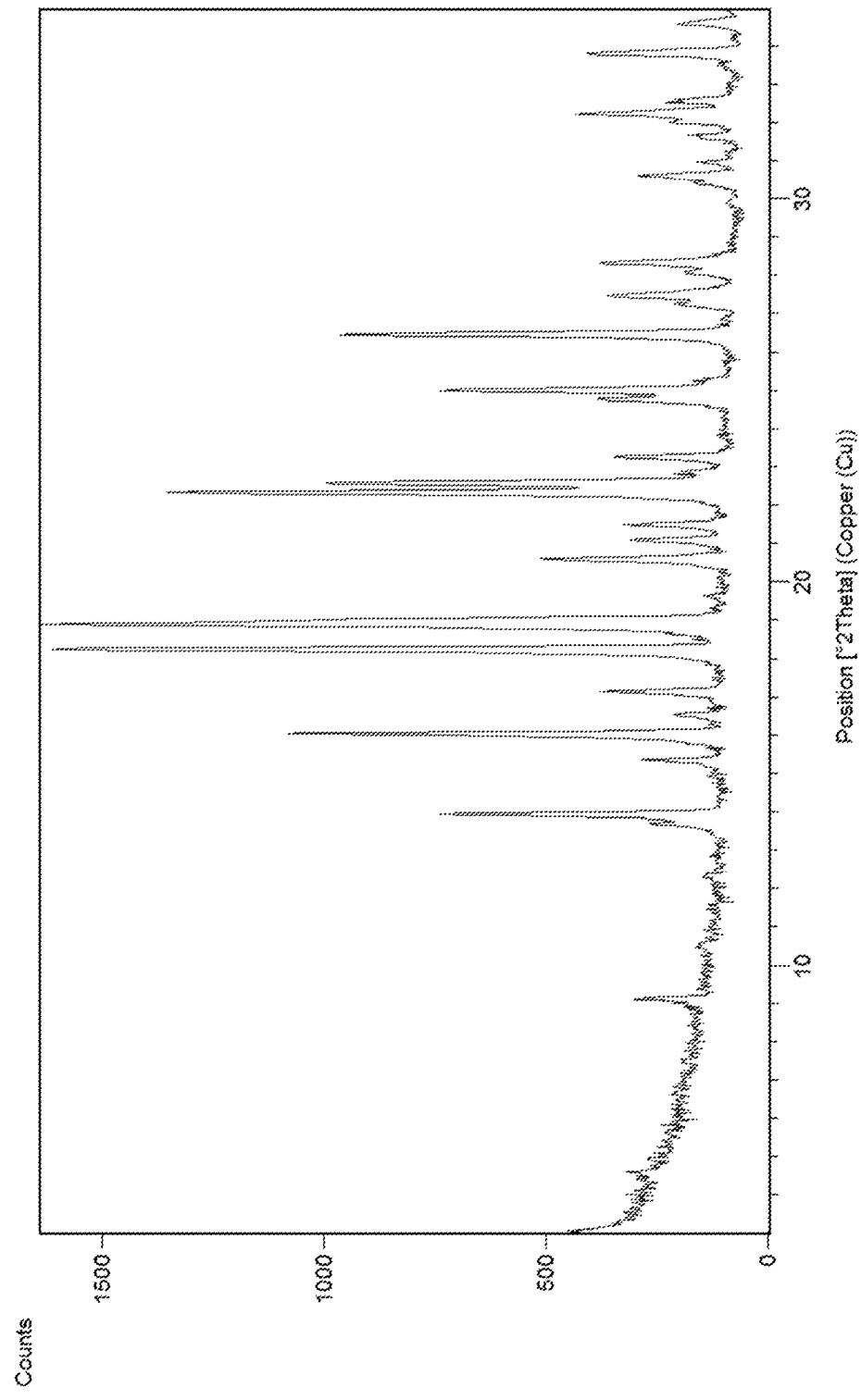
FIG. 1 shows an X-ray powder diffraction diagram of form A of compound I.3.

The X-ray powder diffractogramm of forms A and B were recorded with a Panalytical X'Pert Pro diffractometer in reflection geometry in the range from 2θ=3°-35° with a step width of 0.0167° using Cu-Kα radiation (1.54178 Å) at 25° C. The recorded 2θ valuese were used to calculate the d values. The intensity of the peaks (linear intensity counts) is plotted versus 2θ angel (x axis in °2θ).

Single crystal X-ray diffraction data were collected at 100 K on a Bruker AXS CCD Detector, using graphite-monochromated CuKα radiation (λ=1.54178 Å). The structure was solved with direct methods, refined, and expanded by using Fourier techniques with the SHELX software package (G.M. Sheldrick, SHELX-97, University of Gottingen 1997). Absorbtion correction was performed with SADABS software.

DSC was performed on a Mettler Toledo DSC 823e module. The sample was placed in crimped but vented aluminium pans. Sample size was 3 mg. The thermal behaviour was analysed in the range 30-200° C. by using a heating rate of 10° C./min and a nitrogen stream of 150 mL/min.

Melting point values and polymorphic transitions were confirmed by a Mettler Hot Stage in combination with a light microscope.

A) Preparation of Reagent IV

Example A1

Preparation of an aqueous trimethylsulfonium-methylsulfate solution (11.3 wt-% water)

304 g dimethylsulfide and 30 g water (1.67 mole) were stirred at 25° C. Then, 146 g dimethylsulfate (1.15 mole) were added over 60 min, wherein the temperature increased to up to 35° C. Then, it was stirred 2 h at 35 to 38° C. In order to achieve phase separation, it was cooled to 30° C. and not stirred. 246 g of the lower aqueous phase were obtained.

The water content of the solution was measure by means of Karl-Fischer-titration and was 11.3 wt-%. The content of trimethylsulfonium-methylsulfate was quantified to be 85.3 wt-%; $(SMe_3)^+$: 35 wt-% (quant.-NMR in $D_2O$, di-Na-salt of fumaric acid as internal standard). The viscosity of the solution at 25° C. was 18.3 mPa*s.

Characterization: $^1$H-NMR (400 MHz, D2O): δ/ppm=2.9 (s, 9H), 3.72 (s, 3H), 4.66 (s, $H_2O$).

Example A2

Preparation of an aqueous trimethylsulfonium-methylsulfate solution (14.9 wt-% water)

304 g dimethylsulfide and 41.3 g water (2.3 mole) were stirred at 25° C. Then, 146 g dimethylsulfate (1.15 mole) were added over 60 min, wherein the temperature increased to up to 35° C. Then, it was stirred 2 h at 35 to 38° C. In order to achieve phase separation, it was cooled to 30° C. and not stirred. 259 g of the lower aqueous phase were obtained.

The water content of the solution was measure by means of Karl-Fischer-titration and was 14.9 wt-%. The content of trimethylsulfonium-methylsulfate was quantified to be 83.2 wt-%; (SMe$_3$)$^+$: 34 wt-% (quant.-NMR in D$_2$O, di-Na-salt of fumaric acid as internal standard). The viscosity of the solution at 25° C. was 12.5 mPa*s.

Example A3

Preparation of an aqueous trimethylsulfonium-methylsulfate solution (11.2 wt-% water)

144 g dimethylsulfide, 30 g water (1.67 mole) and 236 g toluol were stirred at 25° C. Then, 146 g dimethylsulfate (1.15 mole) were added over 60 min, wherein the temperature increased to up to 46° C. Then, it was stirred 2 h at 30° C. In order to achieve phase separation, it was cooled to 30° C. and not stirred. 245 g of the lower aqueous phase were obtained.

The water content of the solution was measure by means of Karl-Fischer-titration and was 11.2 wt-%. The content of trimethylsulfonium-methylsulfate was quantified to be 84.5 wt-%; (SMe$_3$)$^+$: 34.8 wt-% (quant.-NMR in D$_2$O, di-Na-salt of fumaric acid as internal standard).

Comparative Example

Preparation of an aqueous trimethylsulfonium-methylsulfate solution (6.5 wt-% water)

304 g dimethylsulfide and 15.0 g water (0.83 mole) were stirred at 25° C. Then, 146 g dimethylsulfate (1.15 mole) were added over 60 min, wherein the temperature was at most 35° C. Then, it was stirred for 2 h at 35 to 38° C. In order to achieve phase separation, it was cooled to 30° C. and not stirred. 237 g of the lower aqueous phase were obtained.

The water content of the solution was measured by means of Karl-Fischer-titration and was 6.5 wt-%. The content of trimethylsulfonium-methylsulfate was quantified to be 89.6 wt-%; (SMe$_3$)$^+$: 37.2 wt-% (quant.-NMR in D$_2$O, di-Na-salt of fumaric acid as internal standard). The viscosity of the solution at 30° C. was 35.1 mPa*s. The solution was not stable at 25° C. Long specular crystals were formed.

B) Synthesis of Oxiranes

Example B1

Synthesis of 2-[4-(4-chlorophenoxy)-2-(trifluoromethyl)phenyl]-2-methyl-oxirane

1-[4-(4-chlorophenoxy)-2-(trifluoromethyl)phenyl]ethanone (0.87 mole) dissolved in 372 g dimethylsulfide together with 250 g aqueous trimethylsulfonium-methylsulfate (86 wt-%, prepared according to Example A1) were provided at 23° C. 15 g KOH pellets, 85 wt-% (0.265 mole), were added while stirring heavily. This led to an increase of temperature of about 5° C. Then, it was continued stirring for 10 h at 38° C. A sample of the reaction mixture showed full conversion of the ketone (HPLC). After that, 1350 g 20 wt-% NaCl solution was added at 30° C. After separation of the aqueous phase, the dimethylsulfide-solution was concentrated by means of distillation of the solvent at a temperature of up to 98° C. 324 g 2-[4-(4-chlorophenoxy)-2-(trifluoromethyl)phenyl]-2-methyl-oxirane having about 90 wt-% (quant. HPLC) were obtained; yield > 99%.

Characterisation

A sample oft the raw product was dissolved at 40° C. in diisopropylether and cooled down to −5° C. The product was obtained as crystalline compound. Melting point: 60° C.

$^1$H-NMR (400 MHz, CDCl3): δ/ppm=1.63 (s, 3H), 2.92 (d, 1H), 3.02 (d, 1H), 6.95 (d, 2H), 7.13 (m, 1H), 7.22 (s, 1H), 7.34 (d, 2H) 7.64 (d, 1H);

$^{13}$C-NMR (125 MHz, CDCl3): δ/ppm=24.82 (q), 55.41 (t), 57.27 (s), 115.94 (d), 120.63 (d, 2C) 121.48 (d), 123.91 (s), 128.60 (s), 129.36 (s), 130.05 (d, 2C), 131.04 (d), 134.59 (s), 154.50 (s), 156.56 (s)

Example B2

Synthesis of 2-[4-(4-chlorophenoxy)-2-(trifluoromethyl)phenyl]-2-cyclopropyl-oxirane 1-[4-(4-chlorophenoxy)-2-(trifluoromethyl)phenyl]cyclopropyl-methanone (0.80 mole) dissolved in 343 g dimethylsulfide together with 263.4 g aqueous trimethylsulfonium-methylsulfate (86 wt-%, prepared according to Example A1) were provided at 23° C. 212 g KOH pellets, 85 wt-% (3.21 mole), were added while stirring heavily. This led to an increase of temperature of about 5° C. to 7° C. Then, it was continued stirring for 8 h at 38° C. A sample of the reaction mixture showed full conversion of the ketone (HPLC). After that, 1236 g 20 wt-% Ige NaCl solution was added at 30° C. After separation of the aqueous phase, the dimethylsulfide-solution was concentrated by means of distillation of the solvent at a temperature of up to 90° C. 332 g of 82 wt-%-product (quant. HPLC) (2-[4-(4-chlorophenoxy)-2-(trifluoromethyl)phenyl]-2-cyclopropyl-oxirane) were obtained; yield >95%.

Characterisation

A sample oft the raw product was dissolved at 60° C. in isopropanole and cooled down to 10° C. The product was obtained as crystalline compound. Melting point: 45° C.

$^{13}$C-NMR (125 MHz, CDCl3): δ/ppm=1.06 (t), 2.17 (t), 15.87 (d), 53.09 (t), 58.46 (s), 115.47 (d), 121.20 (d, 2C) 121.65 (d), 124.01 (s), 127.59 (s), 128.4 (s), 130.16 (d, 2C), 132.10 (d), 133.52 (s), 154.26 (s), 156.27 (s)

Example B3

Synthesis of 2-[4-(4-chlorophenoxy)-2-(trifluoromethyl)phenyl]-2-isopropyl-oxirane 1-[4-(4-chlorophenoxy)-2-(trifluoromethyl)phenyl]-2-methyl-propan-1-one (0.078 mole) dissolved in 62 g dimethylsulfide together with 22.2 g aqueous trimethylsulfonium-methylsulfate (80 wt-%, prepared according to Example A1) were provided at 27° C. 15.4 g KOH pellets, 85 wt-% (0.23 mole), were added while stirring heavily. This led to an increase of temperature of about 5° C. to 7° C. Then, it was continued stirring for 3.5 h at 38° C. A sample of the reaction mixture showed full conversion of the ketone (HPLC). After that, 45 g water were added at 25° C. After separation of the aqueous phase, the dimethylsulfide-solution was diluted with a little toluol and washed again with 105 g water. Then, the organic phase was concentrated by means of distillation of the solvent at 50° C. and up to a pressure of 2 mbar. 30 g of about 81% (area-% HPLC) 2-[4-(4-chlorophenoxy)-2-(trifluoromethyl)phenyl]-2-isopropyl-oxirane were obtained; yield about 88%.

Characterization:

A sample of the raw product was analyzed by means of NMR spectroscopy.

$^{13}$C-NMR (125 MHz, CDCl3): δ/ppm=17.32 (q), 17.55 (q), 31.57 (d), 52.93 (t), 62.71 (s), 116.28 (d), 120.73 (d, 2C) 121.69 (d), 123.95 (s), 127.41 (s), 129.41 (s), 130.12 (d, 2C), 131.97 (d), 134.12 (s), 154.67 (s), 156.56 (s)

$^{1}$H-NMR (400 MHz, CDCl3): δ/ppm=0.85-0.95 (dd, 6H), 2.22-2.35 (md, 1H), 2.78 (d, 1H), 3.20 (d, 1H), 6.98 (d, 2H), 7.10 (m, 1H), 7.23 (s, 1H), 7.35 (d, 2H) 7.55 (d, 1H)

Example B4

Synthesis of 2-[4-(4-chlorophenoxy)-2-(trifluoromethyl)phenyl]-2-methyl-oxirane

1-[4-(4-chlorophenoxy)-2-(trifluoromethyl)phenyl]ethanone (0.13 mole) dissolved in 55 g dimethylsulfide together with 45 g aqueous trimethylsulfonium-methylsulfate (80 wt-%, 17 wt-% H$_2$O), prepared according to Example A2), were provided at 23° C. 25 g KOH pellets, 85 wt-% (0.38 mole), were added while stirring heavily. This led to an increase of temperature of about 5° C. Then, it was continued stirring for 8 h at 38° C. A sample of the reaction mixture showed full conversion of the ketone (HPLC). After that, 199 g 20 wt-% NaCl solution was added at 30° C. After separation of the aqueous phase, the dimethylsulfide-solution was concentrated by means of distillation of the solvent at a temperature of up to 90° C. 56 g of 77 wt-% (quant. HPLC) 2-[4-(4-chlorophenoxy)-2-(trifluoromethyl)phenyl]-2-methyl-oxirane were obtained; yield >95%.

Example B5

Synthesis of 2-[4-(4-chlorophenoxy)-2-(trifluoromethyl)phenyl]-2-methyl-oxirane

1-[4-(4-chlorophenoxy)-2-(trifluoromethyl)phenyl]ethanone (0.45 mole) dissolved in 280 g toluol together with 129 g aqueous trimethylsulfonium-methylsulfate (86 wt-%), prepared according to Example A1, were provided at 24° C. 89 g KOH pellets, 85 wt-% (0.38 mole) were added while stirring heavily. This led to an increase of temperature of about 4° C. Then, it was continued stirring for 21 h at 38° C. A sample of the reaction mixture showed full conversion of the ketone (HPLC). After that, 500 g 20 wt-% 20 wt-% NaCl solution was added at 30° C. After separation of the aqueous phase, the toluol solution was concentrated by means of distillation of the solvent at a temperature of up to 98° C. and a pressure of 50 mbar. 163 g of about 89 wt-% (quant. HPLC) 2-[4-(4-chlorophenoxy)-2-(trifluoromethyl) phenyl]-2-cyclopropyl-oxirane were obtained; yield >95%.

Example B6

Synthesis of 2-[4-(4-chlorophenoxy)-2-(trifluoromethyl)phenyl]-2-methyl-oxirane

1-[4-(4-chlorophenoxy)-2-(trifluoromethyl)phenyl]ethanone (0.128 mole) dissolved in 55.4 g dimethylsulfide were provided at 22° C. 25.4 g KOH pellets, 85 wt-% (0.385 mole) were added while stirring heavily. Then, 42.1 g aqueous trimethylsulfonium-methylsulfate (85.6 wt-%, prepared according to Example A1) were added. This led to an increase of temperature of about 2 to 3° C. Then, it was continued stirring for 8 h at 38° C. A sample of the reaction mixture showed full conversion of the ketone (HPLC). After that, 199 g 20 wt-% Ige 20 wt-% NaCl solution was added at 30° C. After separation of the aqueous phase, the dimethylsulfide solution was concentrated by means of distillation of the solvent at a temperature of up to 90° C. 49.7 g of about 82 wt-% (quant. HPLC) 2-[4-(4-chlorophenoxy)-2-(trifluoromethyl)phenyl]-2-methyl-oxirane were obtained; yield about 97%.

Example B7

Synthesis of 2-[4-(4-chlorophenoxy)-2-(trifluoromethyl)phenyl]-2-cyclopropyl-oxirane 1-[4-(4-chlorophenoxy)-2-(trifluoromethyl)phenyl]cyclopropyl-methanone (0.122 mole) dissolved in 52 g dimethylsulfide were provided at 22° C. 32.2 g KOH pellets, 85 wt-% (0.488 mole), were added while stirring heavily. Then, 40.1 g aqueous trimethylsulfonium-methylsulfate (85.6 wt-%, prepared according to Example A1) were added. This led to an increase of temperature of about 3 to 5° C. Then, it was continued stirring for 8 h at 38° C. A sample of the reaction mixture showed full conversion of the ketone (HPLC). After that, 187 g 20 wt-% ige 20 wt-% NaCl solution was added at 30° C. After separation of the aqueous phase, the dimethylsulfide solution was concentrated by means of distillation of the solvent at a temperature of up to 90° C. 50.0 g, about 82 wt-% (quant. HPLC) 2-[4-(4-chlorophenoxy)-2-(trifluoromethyl)phenyl]-2-methyl-oxirane were obtained; yield about 91%.

C) Synthesis of Triazoles

Example C1

2-[4-(4-chlorophenoxy)-2-(trifluoromethyl)phenyl]-1-(1,2,4-triazol-1-yl)propan-2-ol (compound I.3)

235.3 g (95.4 wt-%; 0.683 mole) 2-[4-(4-chlorophenoxy)-2-(trifluoromethyl)phenyl]-2-methyl-oxirane were provided in 496 g DMF and heated to 60° C. Then, one after the other, 60.6 g (99 wt-%; 0.869 mole) of triazole and 13.4 g (0.335 mole) NaOH-powder were added under stirring. The reaction mixture was heated to 125° C. and then stirred for 4 h in total at this temperature. A HPLC-sample showed almost complete conversion to the desired product (ratio triazol-1-yl/triazol-4-yl about 10:1). About 80% of the DMF was evaporated at 65° C./4 mbar. To the concentrated reaction mixture, 714 g toluol and 400 g water were added. Then, the aqueous phase was separated at 60° C. The toluol phase was washed again with 200 g water. The aqueous phase was separated and the toluol solution was concentrated at 70° C./50 mbar to a solution containing about 50% of the product. Precipitated solids were re-dissolved by heating to 80° C. The solution was cooled down from 80° C. to 0° C. with a rate of 5° K/h under stirring. The suspension of solids was easily stirrable and was separated by suction filtration and washed 2 times with 2×100 g fresh and cold toluol. The solid compound was dried at 25° C./50 mbar.

Yield: 456 g (98 wt-%; triazol-4-yl-Isomer: not detectable); 82% of the theory.

Melting point: 126 to 127° C.

The thus obtained crystalline material was analyzed by means of DSC and by means of X-ray powder diffractometry (XRPD). The X-ray powder diffractogram is depicted in FIG. 1. The reflections are summarized in table 1.

$^{1}$H-NMR (400 MHz, CDCl$_3$): δ/ppm=1.64 (s, 3H), 4.55 (s, OH), 4.44 (d, 1H), 4.62 (d, 1H), 6.92-7.61 (m, 7H), 7.87 (s, 1H), 8.02 (s, 1H)

$^{13}$C-NMR (125 MHz, CDCl$_3$): δ/ppm=27.8 (q), 59.02 (t), 74.77 (s), 118.21 (d), 120.50 (d), 120.82 (d, 2C), 123.95 (CF3), 128.96 (s), 129.54 (s), 130.09 (d, 2C), 130.42 (d), 137.30 (s), 144.34 (d), 151.46 (d), 154.24 (s), 156.49 (s)

Single crystals of form A of compound I.3 were obtained by evaporation from a solution of the title compound in acetonitrile at ambient temperature. Single crystal X-ray diffraction data were collected as described above and the crystallographic parameters were calculated therefrom. The thus calculated crystallographic parameters are summarized in table 2.

Example C2

1-[4-(4-chlorophenoxy)-2-(trifluoromethyl)phenyl]-1-cyclopropyl-2-(1,2,4-triazol-1-yl)ethanol 12.8 g (98 wt-%; 0.182 mole) triazole and 2.86 g (0.07 mole) NaOH powder were added to 217.5 of a 22.8 wt-% DM F-solution of 2-[4-(4-chlorophenoxy)-2-(trifluoromethyl)phenyl]-2-cyclopropyl-oxirane (0.14 mole) at 25° C. After heating to 125° C. the reaction mixture was stirred at this temperature for 10 h in total. A HPLC-sample showed almost complete conversion to the desired product (ratio triazol-1-yl/triazol-4-yl about 7.3:1). About 90% of the DMF was evaporated at 125° C./60 mbar. To the concentrated reaction mixture, 140 g toluole and 86 g water were added at 40° C. Then, the aqueous phase was separated at 80° C. The toluene solution was concentrated up to 86° C./40 mbar. About 133 g of distillate were obtained. The residue was cooled to 60° C. and 25 g methanol were added. After cooling to 45° C., seed crystals were added and the reaction mixture was held at 45° C. for 30 min. Then, the mixture was cooled to 0° C. within 5 h and stirred for 12 h. The suspension of solids was easily stirrable and was separated by suction filtration and washed 1 time with 21 g methanol of a temperature of 0° C. The solid compound was dried at 55° C. and 15 mbar.

Yield: 42.4 g (94.6 wt-%; about 3 wt-% MeOH; ratio triazole-1-yl/triazole-4-yl about 39:1); 68% of the theory.

Melting point: 86 to 87° C.

$^1$H-NMR (400 MHz, CDCl$_3$): δ/ppm=0.28-0.42 (m, 4H), 1.38-1.43 (m, 1H), 4.2-4.4 (s, breit, OH), 4.49 (d, 1H), 4.76 (d, 1H), 6.92-7.76 (m, 7H), 7.92 (s, 1H), 8.0 (s, 1H)

$^{13}$C-NMR (125 MHz, CDCl$_3$): δ/ppm=−0.12 (t), 1.61 (t), 18.91 (d), 58.78 (t), 75.09 (s), 118.14 (d), 120.34 (d), 120.9 (d, 2C), 123.97 (CF3), 129.20 (s), 129.53 (s), 130.08 (d, 2C), 130.92 (d), 137.06 (s), 144.18 (d), 151.84 (d), 154.24 (s), 156.44 (s)

Example C2a crystallization of 1-[4-(4-chlorophenoxy)-2-(trifluoromethyl)phenyl]-1-cyclopropyl-2-(1,2,4-triazol-1-yl)ethanol 206.5 g of a toluene solution of 1-[4-(4-chlorophenoxy)-2-(trifluoromethyl)phenyl]-1-cyclopropyl-2-(1,2,4-triazol-1-yl)ethanol (41.8 wt-%; 0.204 mol) prepared as described in example C2 were concentrated up to 60° C./10 mbar. The residue was cooled to 50° C. and dissolved in mixture of 50 g ethanole and 9 g water. After cooling to 30° C., seed crystals are added and the reaction mixture was held at 30° C. for 60 min. Then, the mixture was cooled to 0° C. with a rate of 2.5° K/min 5 h and stirred for at 0° C. for 4 days. The suspension of solids was easily stirrable and was separated by suction filtration and washed 1 time with 39 g ethanole of a temperature of 0° C. The solid compound was dried at 60° C./10 mbar.

76.4 g (93.7 wt-%; ratio triazole-1-yl/triazole-4-yl about 44:1) colourless crystals containing ethanole in a molar ratio relative to the product of about 1/3 (detected by $^1$H-NMR spectroscopy) were obtained; 83% crystallization yield.

Melting point: 81.5° C.

Example C3

2-[4-(4-chlorophenoxy)-2-(trifluoromethyl)phenyl]-3-methyl-1-(1,2,4-triazol-1-yl)butan-2-ol (compound I.5)

2-[4-(4-chlorophenoxy)-2-(trifluoromethyl)phenyl]-2-isopropyl-oxirane (92.9 g, 76.9 wt-%, 0.217 mole) were dissolved in 180.6 g DMF. To this solution, 27.4 g (98 wt-%; 0.391 mole) triazole and 4.7 g (0.117 mole) NaOH powder were added at 25° C. After heating to 125° C. the reaction mixture was stirred at this temperature for 22.5 h in total. A HPLC-sample showed still remaining oxirane and a ratio of the triazole products of 10.3:1 (triazole-1-yl/triazole-4-yl). The addition of additional 0.3 eq triazole and stirring for another 2 h at 125° C. did not improve the conversion. About 79% of the DMF were evaporated at up to 60° C./4 mbar. 413 g toluole and 205 g water were added to the concentrated reaction mixture at 80° C. Then, the aqueous phase was separated at 55° C. The toluol solution was concentrated at up to 90° C./40 mbar until a residue of 108 g remained. 111 g methanol were added to the residue at 60° C. The solution obtained was cooled down to −1° C. with a rate of 5° C./h. Seed crystals were added at 45° C. The suspension of solids was easily stirrable and was separated by suction filtration and washed 1 time with 25 g of fresh and cold (0° C.) methanol. The solid compound was dried at 55° C. and 50 mbar.

Yield: 64.8 g (96.9 wt-%; ratio triazole-1-yl/triazole-4-yl about 100:1); 73% of the theory. The crystals contained residual methanol as detected be $^1$H-NMR Melting point: 114 to 115° C.

$^1$H-NMR (400 MHz, CDCl$_3$): δ/ppm=0.87 (d, 3H), 1.2 (d, 3H), 2.38 (m, 1H), 4.3-4.65 (s, breit, OH), 4.58 (d, 1H), 4.75 (d, 1H), 6.85-7.54 (m, 7H), 7.7 (s, 1H), 7.8 (s, 1H)

$^{13}$C-NMR (125 MHz, CDCl$_3$): δ/ppm=16.83 (q), 17.44 (q), 37.00 (d), 57.70 (t), 80.43 (s), 117.98 (d), 120.13 (d), 120.87 (d, 2C), 123.75 (CF3), 129.54 (s), 130.10 (d, 2C), 130.20 (d), 130.82 (s), 136.65 (s), 143.83 (d), 151.69 (d), 154.20 (s), 156.06 (s)

Example C4

2-[4-(4-chlorophenoxy)-2-(trifluoromethyl)phenyl]-3-methyl-1-(1,2,4-triazol-1-yl)butan-2-ol (compound I.5)

Figure 2:
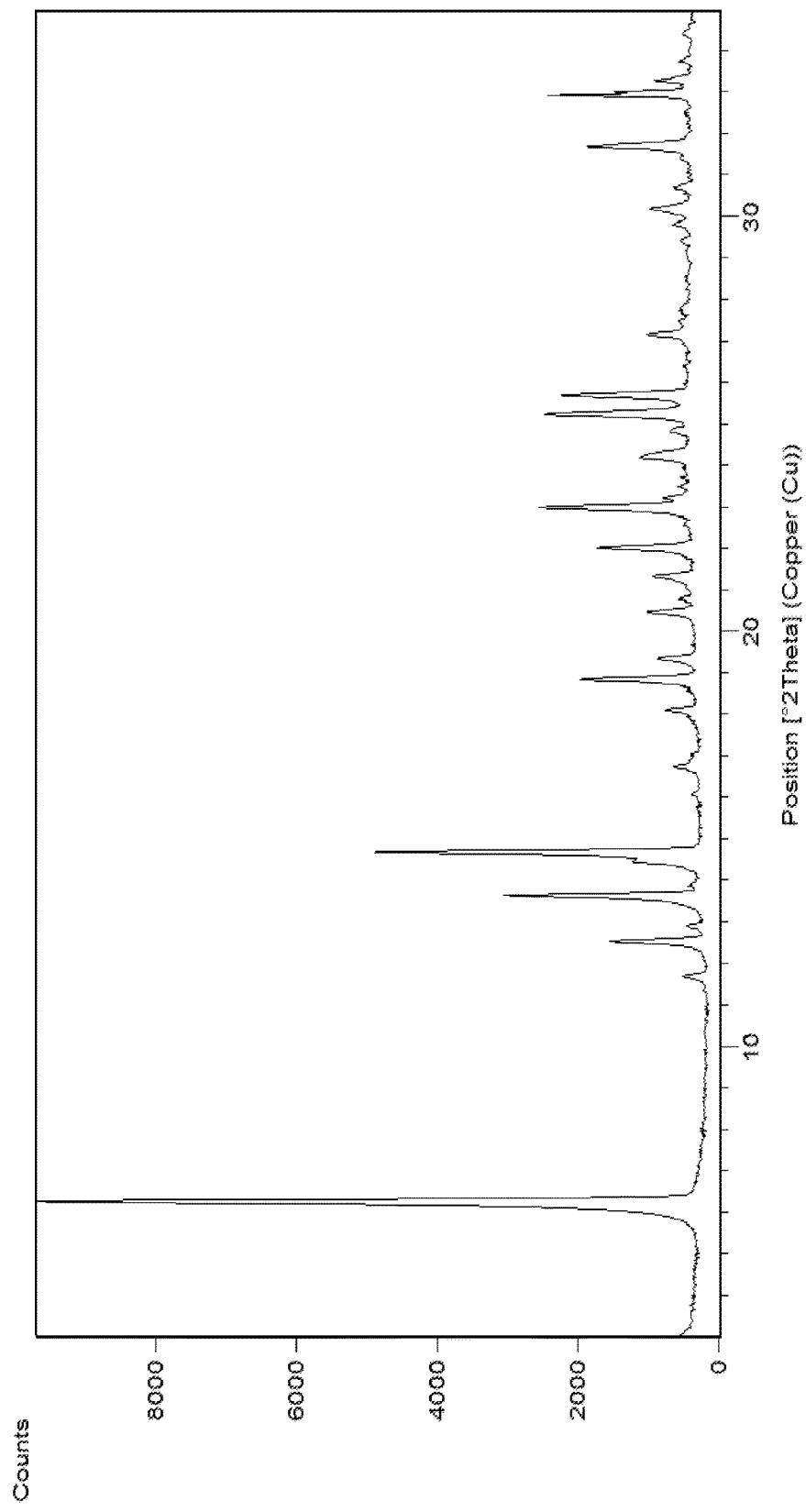
FIG. 2 shows an X-ray powder diffraction diagram of form A of compound I.5.

Preparation of compound I.5 was performed as described for experiment C.3, except that no seed crystals were added at 45° C. during cooling of the solution of compound I.5 in methanol. The thus obtained crystalline material was analyzed by means of DSC and by means of X-ray powder diffractometry (XRPD). The X-ray powder diffractogram is depicted in FIG. 2. The reflections are summarized in table 3.

Single crystals of form A of compound I.5 were obtained by dissolving thus obtained compound I.5 in 3-propanol and allowing heptane to diffuse into this solution at ambient temperature. Single crystal X-ray diffraction data were collected as described above and the crystallographic parameters were calculated therefrom. The thus calculated crystallographic parameters are summarized in table 4.

D) Comparison Examples for the Amount of Base Used:

The base and the triazole in the amounts detailed in the table D below were added to a 20-25% solution of the respective oxirane II in DMF. At 125° C., the product of formula I was obtained. After evaporation of the major amount of DMF, the residue was partioned between toluole and water. The yield was determined after azeotropic drying and concentration by means of quantitative HPLC from the toluol solution.

TABLE D

| example | 1 eq oxirane II | eq triazole | eq base | temp./duration | yield of 1-triazolyl |
|---|---|---|---|---|---|
| D1 | $R^1$ = cylopropyl<br>$(R^3)_n$ = 2-$CF_3$<br>$(R^4)_m$ = 4-Cl | 1.3 | NaOH/0.5 | 125° C./10 h | 82% |
| D2 | $R^1$ = $CH_3$<br>$(R^3)_n$ = 2-$CF_3$<br>$(R^4)_m$ = 4-Cl | 1.3 | NaOH/1.3 | 125° C./6 h | 86% |
| D3 | $R^1$ = cylopropyl<br>$(R^3)_n$ = 2-$CF_3$<br>$(R^4)_m$ = 4-Cl | 1.3 | NaOH/1.3 | 125° C./12 h | 75% |
| D4 | $R^1$ = $CH_3$<br>$(R^3)_n$ = 2-$CF_3$<br>$(R^4)_m$ = 4-Cl | 1.3 | KOH/0.3 | 125° C./5.5 h | 93% |
| D5 | $R^1$ = $CH_3$<br>$(R^3)_n$ = 2-$CF_3$<br>$(R^4)_m$ = 4-Cl | 1.3 | NaOH/0.3 | 125° C./5 h | 91% |
| D6 | $R^1$ = $CH_3$<br>$(R^3)_n$ = 2-$CF_3$<br>$(R^4)_m$ = 4-Cl | 1.3 | KOH/1.3 | 125° C./6 h | 89% |
| D7 | $R^1$ = cylopropyl<br>$(R^3)_n$ = 2-$CF_3$<br>$(R^4)_m$ = 4-Cl | 1.3 | KOH/1.3 | 125° C./16 h | 56% |
| D8 | $R^1$ = cylopropyl<br>$(R^3)_n$ = 2-$CF_3$<br>$(R^4)_m$ = 4-Cl | 1.3 | KOH/0.3 | 125° C./12 h | 76% |

E1) Comparative Example

To 1-[4-(4-chlorophenoxy)-2-(trifluoromethyl)phenyl]cyclopropyl-methanone (0.13 mol) dissolved in 55 g dimethylsulfide together with 42 g aqueous trimethylsulfonium-methylsulfate (86 wt-%, prepared according top Example A1) at 22° C., 15.7 g NaOH pellets (98 wt-%) (0.385 mol) were added under vigorous stirring. This led to an increase in temperature of about 5 to 6° C. Then, stirring was continued for 20 h at 38° C. A sample of the reaction solution showed incomplete conversion of the keton (detection by means of HPLC). Then, 199 g 20 wt-% NaCl solution were added at 30° C. After separation of the aqueous phase, the dimethyl sulfide solution was concentrated by means of distillation of the solvent at a temperature of up to 90° C. 59.7 g (about 47 wt-% product, determined with quantitative HPLC) 2-[4-(4-chlorophenoxy)-2-(trifluoromethyl)phenyl]-2-methyl-oxirane were obtained; Yield: 66%

E2) Comparative Example

Use of 50% Ig Aqueous KOH Leads to Incomplete Conversion of Reagents

To 1-[4-(4-chlorophenoxy)-2-(trifluoromethyl)phenyl]cyclopropyl-methanone (0.13 mol), dissolved in 55 g dimethylsulfide together with 42 g aqueous trimethylsulfonium-methylsulfate (86 wt-%, prepared according to Example A1) at 22° C., 15.743 g 50% aqueous KOH (0.385 mol) were added under vigorous stirring. This led to an increase in temperature of about 5 to 6° C. Then, stirring was continued for 32 h at 38° C. A sample of the reaction solution showed incomplete conversion of the keton (detection by means of HPLC). Then, 199 g 20 wt-% NaCl solution were added at 30° C. After separation of the aqueous phase, the dimethyl sulfide solution was concentrated by means of distillation of the solvent at a temperature of up to 90° C. 53.5 g (about 34.5 wt-% product, determined with quantitative HPLC) of 2-[4-(4-chlorophenoxy)-2-(trifluoromethyl)phenyl]-2-methyl-oxirane were obtained. Yield: 44%.

The invention claimed is:

1. A crystalline form of 2-[4-(4-chlorophenoxy)-2-(trifluoromethyl)phenyl]-1-(1,2,4-triazol-1-yl)propane-2-ol which, in an X-ray powder diffractogram at 25° C. using Cu—$K_\alpha$ radiation, shows at least six of the fifteen following reflections, given as 2θ values: 9.16±0.20, 13.95±0.20, 15.35±0.20, 16.04±0.20, 16.51±0.20, 17.17±0.20, 18.26±0.20, 18.89±0.20, 20.59±0.20, 21.11±0.20, 21.49±0.20, 22.33±0.20, 22.60±0.20, 23.26±0.20, 26.46±0.20.

2. An agrochemical composition containing the crystalline form as claimed in claim 1 and an auxiliary.

3. A method for controlling harmful fungi, which method comprises applying the crystalline form of claim 1 to the fungi or plants, soil, seeds or non-living materials.

* * * * *